(12) United States Patent
Motayed et al.

(10) Patent No.: US 10,139,382 B2
(45) Date of Patent: Nov. 27, 2018

(54) DEVICE HAVING AN ARRAY OF SENSORS ON A SINGLE CHIP

(71) Applicants: UNIVERSITY OF MARYLAND, COLLEGE PARK, College Park, MD (US); THE UNITED STATES OF AMERICA, AS REPRESENTED BY THE SECRETARY OF COMMERCE, Washington, DC (US); GEORGE MASON UNIVERSITY, Fairfax, VA (US); THE GEORGE WASHINGTON UNIVERSITY, Washington, DC (US)

(72) Inventors: Abhishek Motayed, Rockville, MD (US); Geetha Aluri, Clifton Park, NY (US); Albert V. Davydov, North Potomac, MD (US); Mulpuri V. Rao, Fairfax Station, VA (US); Vladimir P. Oleshko, Gaithersburg, MD (US); Ritu Bajpai, Santa Clara, CA (US); Mona E. Zaghloul, Bethesda, MD (US)

(73) Assignees: UNIVERSITY OF MARYLAND, COLLEGE PARK, College Park, MD (US); THE UNITED STATES OF AMERICA, AS REPRESENTED BY THE SECRETARY OF COMMERICE, Washington, DC (US); GEORGE MASON UNIVERSITY, Fairfax, VA (US); THE GEORGE WASHINGTON UNIVERSITY, Washington, DC (US)

( * ) Notice: Subject to any disclaimer, the term of this patent is extended or adjusted under 35 U.S.C. 154(b) by 0 days.

(21) Appl. No.: 15/891,709

(22) Filed: Feb. 8, 2018

(65) Prior Publication Data

US 2018/0172656 A1 Jun. 21, 2018

Related U.S. Application Data

(63) Continuation of application No. 15/297,693, filed on Oct. 19, 2016, now Pat. No. 9,983,183, which is a (Continued)

(51) Int. Cl.
*G01N 27/00* (2006.01)
*G01N 33/00* (2006.01)
*G01N 27/12* (2006.01)

(52) U.S. Cl.
CPC ....... *G01N 33/0057* (2013.01); *G01N 27/127* (2013.01); *G01N 33/004* (2013.01);
(Continued)

(58) Field of Classification Search
CPC ............. G01N 33/0057; G01N 27/127; G01N 33/0031; G01N 33/005; G01N 33/0044;
(Continued)

(56) References Cited

PUBLICATIONS

Lim et al, Room temperature hydrogen detection using Pd-coated GaN nanowires. Appl. Phys. Lett. 93:072109 (2008) (Year: 2008).*
(Continued)

*Primary Examiner* — Dennis White
(74) *Attorney, Agent, or Firm* — Patent Portfolio Builders PLLC

(57) ABSTRACT

A nanostructure sensing device comprises a semiconductor nanostructure having an outer surface, and at least one of metal or metal-oxide nanoparticle clusters functionalizing the outer surface of the nanostructure and forming a photoconductive nanostructure/nanocluster hybrid sensor enabling light-assisted sensing of a target analyte.

25 Claims, 47 Drawing Sheets

Related U.S. Application Data continuation-in-part of application No. 13/861,962, filed on Apr. 12, 2013, now Pat. No. 9,476,862.

(60) Provisional application No. 61/775,305, filed on Mar. 8, 2013, provisional application No. 61/730,865, filed on Nov. 28, 2012, provisional application No. 61/625,511, filed on Apr. 17, 2012, provisional application No. 61/623,957, filed on Apr. 13, 2012.

(52) U.S. Cl.
CPC ....... *G01N 33/005* (2013.01); *G01N 33/0031* (2013.01); *G01N 33/0037* (2013.01); *G01N 33/0042* (2013.01); *G01N 33/0044* (2013.01); *G01N 33/0047* (2013.01); *G01N 33/0049* (2013.01); *G01N 33/0054* (2013.01); *Y02A 50/245* (2018.01); *Y02A 50/246* (2018.01)

(58) Field of Classification Search
CPC ........... G01N 33/0042; G01N 33/0049; G01N 33/0037; G01N 33/0047; G01N 33/0054; G01N 33/004; Y02A 50/246; Y02A 50/245

See application file for complete search history.

(56) References Cited

PUBLICATIONS

Brattain JB WH (1952) "Surface properties of germanium," Bell. Syst. Tech. Journal 32:1 (Year: 1952).*
Navrotsky A et al. (1967) "Enthalpy of Transformation of a High-Pressure Polymorph of Titanium Dioxide to the Rutile Modification," Science 158:388 (Year: 1967).*
Jamieson J C and Olinger B (1969) "Pressure-temperature studies of anatase, brookite, rutile, and TiO2(11); A discussion," Am. Min 54:1477-1480 (Year: 1969).*
Norton P R and Richards P J (1974) "The heat of adsorption of hydrogen on platinum," Surface Science 44:129-140 (Year: 1974).*
Sexton B A etal. (1982) "Decomposition pathways of C1-C4 alcohols adsorbed on platinum (111)," Surface Science 121:181-198 (Year: 1982).*
Morrison S R (1987) "Selectivity in Semiconductor Gas Sensors." Sens, and Actuators 12:425-440 (Year: 1987).*
Meyer G J et al. (1988) "Evidence for adduct formation at the semiconductor-gas interference. Photoluminsecent properties of cadmium selenide in the presence of amines," J. Am. Chem. Soc. 110:4914-4918 (Year: 1988).*
Kim K S and Barteau M A (1989) "Reaction of Methanol onTiCh," Surface Science 223:13-32 (Year: 1989).*
Anpo M et al. (1989) "In situ photoluminescence of titania as a probe of photocatalytic reactions," The Journal of Physical Chemistry 93(21):7300-7302 (Year: 1989).*
Tanaka K et al. (1991) "Effect of crystallinity of TiO2 on its photocatalytic action," Chem. Phys. Lett. 187:73-76 (Year: 1991).*
Mao Y et al. (1991) "Identification of organic acids and other intermediates in oxidative degradation of chlorinated ethanes on titania surfaces en route to mineralization: a combined photocatalytic and radiationchemical study," J. Phys. Chem. 95:10080-10089 (Year: 1991).*
Azad AM et al. (1992) "Solid-State Sensors: A Review," J. Electrochem. Soc. 139(12):3690-3704 (Year: 1992).*
Janata J (1992) "Chemical Sensors." Anal. Chem. 64(12):196-219 (Year: 1992).*
Heimer T A et al. (1993) "Molecular level photovoltaics: the electrooptical properties of metal cyanide complexes anchored to titanium dioxide," J. Phys. Chem. 97:11987-11994 (Year: 1993).*
Butler E C and Davis A P (1993) "Photocatalytic oxidation in aqueous titanium dioxide suspensions-the influence of dissolved transition metals," J. Photochem. Photobiol. A 70:273-283 (Year: 1993).*
Tang H et al. (1994) "Electrical and optical properties of TiO2 anatase thin films," J. Appl. Phys. 75:2042-2047 (Year: 1994).*
Gopel, W. (1994) "New materials and transducers for chemical sensors," Sensors and Actuators B: Chemical 18(1-3):1-21 (Year: 1994).*
Linsbigler A L et al. (1995) "Photocatalysis on TiO2 Surfaces: Principles, Mechanisms, and Selected Results," Chem. Rev. 95:735-758 (Year: 1995).*
Hoffman M R et al. (1995) "Environmental Applications of Semiconductor Photocatalysis," Chem. Rev. 95:69-96 (Year: 1995).*
Conner W C et al. (1995) "Spillover in heterogeneous catalysis," Chem. Rev. 95:759-788 (Year: 1995).*
Meixner H and Lampe U (1996) "Metal oxide sensors," Sens, and Actuators B 33:198-202 (Year: 1996).*
Luo Y and Ollis D F (1996) "Heterogeneous photocatalytic oxidation of trichloroethylene and toluene mixtures in air: Kinetic promotion and inhibition, time-dependent catalyst activity," J. Catal. 163:1-11 (Year: 1996).*
Ioannides T and Verykios X E (1996) "Charge Transfer in Metal Catalysts Supported on Doped TiCh: A Theoritical Approach Based on Metal-Semiconductor Contact Theory," Journal of Catalysis 161:560-569 (Year: 1996).*
Mills A and Hunte S L (1997) "An overview of of semiconductor photocatalysis," J. Photochem. Photobiol. A 108:1-35 (Year: 1997).*
Zhang H Z and Banfield J. F (1998) "Thermodynamic analysis of phase stability of nanocrystalline titania," J. Mater. Chem. 8:2073-2076 (Year: 1998).*
Nosaka Y et al. (1998) "Factors governing the initial process of TiO2 photocatalysis studied by means of in situ electron spin resonance measurements." J. Phys. Chem. B 102:10279-10283 (Year: 1998).*
Li M et al. (1999) "Oxygen-induced restructuring of rutile TiO(I 10): formation mechanism, atomic models, and influence on surface chemistry," Faraday Discuss. 114:245-258 (Year: 1999).*
Zywietzetal. (1999) "The adsorption of oxygen at GaN surfaces," Appl. Phys. Lett. 74:1695-1697 (Year: 1999).*
Henderson M A et al. (1999) "The chemistry of methanol on the TiO2(I 10) surface: the influence of vacancies andcoadsorbed species" Faraday Discuss. 114:313-329 (Year: 1999).*
Shimizu Y and Egashira M (1999) "Basic Aspects and Challenges of Semiconductor Gas Sensors," Mater. Res. Soc. Bull. 24:18-24 (Year: 1999).*
Anpo M et al. (1999) "Generation of superoxide ions at oxide surfaces," Top. Catal. 8:189-198 (Year: 1999).*
Henderson M A et al. (1999) "Interaction of Molecular Oxygen with the Vacuum-Annealed TiO2(110) Surface: Molecular and Dissociative Channels," J. Phys. Chem. B 103:5328-5337 (Year: 1999).*
Zhang H Z and Banfield J. F (2000) "Understanding polymorphic phase transformation behavior during growth of nanocrystalline aggregates: insights from TiO2." J. Phys. Chem. B 104:3481-3487 (Year: 2000).*
Garzella C et al. (2000) "TiO2 thin films by a novel sol-gel processing for gas sensor applications," Sens, and Actuators B: Chemical 68:189-196 (Year: 2000).*
Kong J etal. (2000) "Nanotube Molecular Wires as Chemical Sensors." Science 287:622-625 (Year: 2000).*
Perkins C L and Henderson M A (2001) "Photodesorption and Trapping of Molecular Oxygen at the TiO2(110)-Water Ice Interface." J. Phys. Chem. B. 105:3856-3863 (Year: 2001).*
Cui Y et al. (2001) "Nanowire Nanosensors for Highly Sensitive and Selective Detection of Biological and Chemical Species," Science 293:1289-1292 (Year: 2001).*
Wilson D M et al. (2001) "Chemical Sensors for Portable, Handheld Field Instruments," IEEE Sensors Journal 1:256-274 (Year: 2001).*
Yamakata A et al. (2002) "Electron- and hole-capture reactions on Pt/TiO2 photocatalyst exposed to methanol vapor studied with time-resolved infrared absorption spectroscopy," J. Phys. Chem. B 106:9122-9125 (Year: 2002).*
Du X et al. (2002) "A New Highly Selective H2 Sensor Based on TiO2/Pt0-Pt Dual-Layer Films," Chem. Mater. 14:3953-3957 (Year: 2002).*

(56) References Cited

PUBLICATIONS

Kamat P V (2002) "Photophysical, photochemical and photocatalytic aspects of metal nanoparticles," The Journal of Physical Chemistry B 106(32):7729-7744 (Year: 2002).*
Comini E et al. (2002) "Stable and highly sensitive gas sensors based on semiconducting oxide nanobelts," Appl. Phys. Lett. 81:1869 (3 pages) (Year: 2002).*
Zhdanov V P (2002) "Nm-sized metal particles on a semiconductor surface, Schottky model, etc " Surface Science 512:L331-L334 (Year: 2002).*
Saeys M et al. (2002) "Density Functional Study of Benzene Adsorption on Pt111," J. Phys. Chem. B 10:7489-7498 (Year: 2002).*
Yinon, J. (2002) "Field detection and monitoring of explosives," TrAC Trends in Analytical Chemistry 21(4): 292-301 (Year: 2002).*
Herman G S et al. (2003) "Experimental Investigation of the Interaction of Water and Methanol with Anatase-TiO2(101)," J. Phys. Chem. B 107:2788-2795 (Year: 2003).*
de Lara-Castells M P And Krause J L (2003) "Theoretical study of the UV-induced desorption of molecular oxygen from the reduced TiCh (110) surface," J. Chem. Phys. 118:5098 (Year: 2003).*
Li C et al. (2003) "In2O3 nanowires as chemical sensors," Appl. Phys. Lett. 8:1613-1615 (Year: 2003).*
Motayed A et al. (2003) "Electrical, thermal, and microstructural characteristics of Ti/Al/Ti/Au multilayer ohmic contacts to n-type GaN," J. Appl. Phys. 93(2): 1087-1094 (Year: 2003).*
Zhang D et al. (2004) "Detection of NO2 down to ppb levels using individual and multiple In2O3 nanowire devices," Nano. Lett. 4:1919-1924 (Year: 2004).*
Carp O et al. (2004) "Photoinduced reactivity of titanium dioxide." Prog. Solid St. Chem. 32:33-177 (Year: 2004).*
Moore, D.S. (2004) "Instrumentation for trace detection of high explosives," Review of Scientific Instruments 75(8):2499-2512 (Year: 2004).*
Parnneter JE (2004) "The challenge of standoff explosives detection," in 38th Annual 2004 International Carnahan Conference on Security Technology. 355-358 (Year: 2004).*
Eranna G et al. (2004) "Oxide Materials for Development of Integrated Gas Sensors—A Comprehensive Review / Integrated Gas Sensors—A Comprehensive Review," Critical Reviews in Solid State and Material Sciences 29:111-188 (Year: 2004).*
Wan Q et al. (2004) "Fabrication and ethanol sensing characteristics of ZnO nanowire gas sensors," Appl. Phys. Lett. 84:3654-3656 (Year: 2004).*
Wang H T et al. (2005) "Hydrogen-selective sensing at room temperature with ZnO nanorods," Appl. Phys. Lett. 86:243503 (Year: 2005).*
Liu J et al. (2005) "Vanadium Pentoxide Nanobelts: Highly Selective and Stable Ethanol Sensor Materials," Advanced Materials 17:764-767 (Year: 2005).*
Raible I et al. (2005) "V2O5 nanofibers: novel gas sensors with extremely high sensitivity and selectivity to amines," Sens, and Actuators B 106:730-735 (Year: 2005).*
Ruiz A M et al. (2005) "Effects of various metal additives on the gas sensing performances of TiO2 nanocrystals obtained from hydrothermal treatments," Sensors and Actuators B: Chemical 108:34-40 (Year: 2005).*
Sippel-Oakley J et al. (2005) "Carbon nanotube films for room temperature hydrogen sensing," Nanotechnology 16:2218-2221 (Year: 2005).*
Wang C et al. (2005) "Detection of H2S down to ppb levels at room temperature using sensors based on ZnO nanorods " Sens, and Actuators B 113:320-323 (Year: 2005).*
Wang G C et al. (2005) "Characterization of methoxy adsorption on some transition metals: A first principles density functional theory study." J. Chem. Phys. 122:044707 (8 pages) (Year: 2005).*
Motayed A et al. (2006) "Realization of reliable GaN nanowire transistors utilizing dielectrophoretic alignment technique," J. Appl. Phy. 100:114310 (Year: 2006).*
Chen Y J et al. (2006) "Linear ethanol sensing of SnO2 nanorods with extremely high sensitivity," Applied Physics Letters 88: 083105 (3 pages) (Year: 2006).*
Bikondoa 0 et al. (2006) "Direct visualization of defect-mediated dissociation of water on TiCLQIO)," Nat. Mater. 5:189-192 (Year: 2006).*
Dobrokhotov V et al. (2006) "Principles and mechanisms of gas sensing by GaN nanowires functionalized with gold nanoparticles." J. Appl. Phys 99:104302 (Year: 2006).*
Thompson T L and Yates J T Jr. (2006) "Control of a surface photochemical process by fractal electron transport across the surface : 0(2) photodesorption from TiO(2)(110)," J. Phys. Chem. B 110:7431-7435 (Year: 2006).*
Joshi R K and Krnis F E (2006) "Influence of Ag particle size on ethanol sensing of SnOi /\Ag nanoparticle films: A method to develop parts per billion level gas sensors " Appl. Phvs. Lett. 89:153116 (Year: 2006).*
Xue XY et al. (2006) "Synthesis and ethanol sensing properties of indium-doped tin oxide nanowires," Applied Physics Letters 88: 201907 (Year: 2006).*
Yang Y Z et al. (2006) "Photo-Catalytic Production of Hydrogen Form Ethanol over MyTiO2 Catalysts (M = Pd, Pt orRh)," Applied Catalysis B: Environmental 67:217-222 (Year: 2006).*
Chen Y et al. (2006) "The enhanced ethanol sensing properties of multi-walled cartoon nanotubes/SnOicore/shell nanostructures," Nanotechnology 17:3012-3017 (Year: 2006).*
Bertness K A et al. (2007) "Nucleation conditions for catalyst-free GaN nanowires," Journal of Crystal Growth 300:94-99 (Year: 2007).*
Lao C S et al. (2007) "Giant Enhancement in UV Response of ZnO Nanobelts by Polymer Surface-Functionalization," J. Am Chem. Soc. 129:12096-12097 (Year: 2007).*
McAlpine M C et al. (2007) "Highly ordered nanowire arrays on plastic substrates for ultrasensitive flexible chemical sensors," Nat Mater 6:379-384 (Year: 2007).*
Hiehata K et al. (2007) "Local work function analysis of Pt/TiO2 photocatalyst by a Kelvin probe force microscope," Nanotechnology 18:084007 (6 pages) (Year: 2007).*
Huang X J and Choi Y K (2007) "Chemical sensors based on nanostructured materials," Sens. Actuators B, Chem. 122(2):659-671 (Year: 2007).*
Lee F K et at. (2007) "Role of water adsorption in photoinduced superhydrophilicity on TiCfe thin films," Appl. Phys. Lett. 90:181928 (Year: 2007).*
Sun Y and Wang HH (2007) "High-Performance, Flexible Hydrogen Sensors That Use Carbon Nanotubes Decorated with Palladium Nanoparticles," Advanced Materials 19:2818-2823 (Year: 2007).*
Sberveglieri G et al. (2007) "Synthesis and characterization of semiconducting nanowires for gas sensing," Sensors and Actuators B: Chemical 121:208-213 (Year: 2007).*
Wu R J et al. (2008) "Application of m-CNTs/NaCICL/Ppy to a fast response, room working temperature ethanol sensor," Sensors and Actuators B: Chemical 134:213-218 (Year: 2008).*
Bertness K A et al. (2008) "Mechanism for spontaneous growth of GaN nanowires with molecular beam epitaxy" J. Cryst. Growth310(13):3154-3158 (Year: 2008).*
Lim W et al. (2008) "Room temperature hydrogen detection using Pd-coated GaN nanowires," Appl.Phys. Lett. 93:072109 (Year: 2008).*
Morikawa T et al. (2008) "Visible-light-induced photocatalytic oxidation of carboxylic acids and aldehydes over N-doped TiO2 loaded with Fe, Cu or Pt," Applied Catalysis B: Environmental 83: 56-62 (Year: 2008).*
de Lacy Costello B P J et al (2008) "Highly sensitive room temperature sensors based on the UV-LED activation of zinc oxide nanoparticles," Sens. Actuators B, Chem. 134(2):945-952 (Year: 2008).*
Balazsi C et al. (2008) "Novel hexagonal W03 nanopowder with metal decorated carbon nanotubes as N02 gas sensor," Sensors and Actuators B: Chemical 133:151-155 (Year: 2008).*
Fujishima A et al. (2008) "TiO2 photocatalysis and related surface phenomena" Surf. Sci. Rep. 63:515-582 (Year: 2008).*

(56) References Cited

PUBLICATIONS

Wahab H S et al. (2008) "Computational investigation of water and oxygen adsorption on the anatase Ti02 (100) surface," J. Mol. Chem. Struct. :THEOCHEM 868:101-108 (Year: 2008).*

Zalkind S et al. (2008) "Interaction of benzene with TiO2surfaces: Relevance to contamination of extreme ultraviolet lithography mirror capping layers," J. Vac. Sci. Technol. B 26:2241-2246 (Year: 2008).*

Duy N V et al. (2008) "Mixed SnCVTiCh Included with Carbon Nanotubes for Gas-Sensing Application," J. Physica E 41:258-263 (Year: 2008).*

Chang S-J et al. (2008) "Highly sensitive ZnO nanowire CO sensors with the adsorption of Au nanoparticles," Nanotechnology 19: 175502 (Year: 2008).*

Gong J et al. (2008) "Micromachined sol-gel carbon nanotube/Sn02 nanocomposite hydrogen sensor," Sensors and Actuators B: Chemical 130:829-835 (Year: 2008).*

Senesac L and Thundat TG, (2008) "Nanosensors for trace explosive detection," Materials Today II(3):28-36 (Year: 2008).*

Kuang Q et al. (2008) "Enhancing the photon- and gas-sensing properties of a single Sn02 nanowire based nanodevice by nanoparticle surface functionalization." J. Phvs. Chem. C 112:11539-11544 (Year: 2008).*

Shen Y et al. (2009) "Hydrogen sensors made of undoped and Pt-doped Sn02 nanowires," Journal of Alloys and Compounds 488: L21-L25 (Year: 2009).*

Wu W-Y et al. (2009) "Electrospun ZnO Nanowires as Gas Sensors for Ethanol Detection," Nanoscale Research Letters 4:513-517 (Year: 2009).*

Prades J D et al. (2009) "Equivalence between thermal and room temperature UV light-modulated responses of gas sensors based on individual Sn02 nanowires," Sens. Actuators B, Chem. 140(2):337-341 (Year: 2009).*

Brahim S et at. (2009) "Carbon nanotube-based ethanol sensors." Nanotechnology 20:235502 (Year: 2009).*

Mansfield LM et al. (2009) "GaN nanowire carrier concentration calculated from light and dark resistance measurements," Journal of Electronic Materials 38:495-504 (Year: 2009).*

Yates Jr J T (2009) "Photochemistry on Ti02: mechanisms behind the surface chemistry," Surf. Sci. 603:1605-1612 (Year: 2009).*

Skucha K et al. (2010) "Palladium/silicon nanowire Schottky barrier-based hydrogen sensors," Sensors and Actuators B: Chemical 145:232-238 (Year: 2010).*

Ahn H et al. (2010) "Vertically Aligned Nanorod Sensor on Flexible Substrate for Ethanol Gas Monitoring," Electrochem. Solid-State Lett. 13:J125-J128 (Year: 2010).*

Sanford N A et al. (2010) "Steady-state and transient photoconductivity in c-axis GaN nano wires grown by nitrogen-plasma-assisted molecular beam epitaxy " J. Appl. Phy. 107:034318 (Year: 2010).*

Mubeen S et al. (2010) "Sensitive detection of H2S using gold nanoparticle decorated single-walled carbon nanotubes," Anal. Chem. 82:250-257 (Year: 2010).*

Engel Y et al. (2010) "Supersensitive Detection of Explosives by Silicon Nanowiie Arrays," Angewandte Chemie International Edition 49(38):6830-6835 (Year: 2010).*

Leghrib R et al. (2010) "Gas sensors based on multiwall carbon nanotubes decorated with tin oxide nanoclusters," Sens, and Actuators B: Chemical 145:411416 (Year: 2010).*

Ramgir N S et al. (2010) "Nanowire-based sensors." Small 6:1705-1722 (Year: 2010).*

Zhang Y et al. (2010) "Decoration of ZnO nanowires with Pt nanoparticles and their improved gas sensing and photocatalytic performance," Nanotechnology 21:285501 (Year: 2010).*

Offermans P et al. (2010) "Gas detection with vertical InAs nanowire arrays," Nano Lett. 10:2412-2415 (Year: 2010).*

Lupan O et al. (2010) "Selective hydrogen gas nanosensor using individual ZnO nanowire with fast response at room temperature." Sensors and Actuators B: Chemical 144:56-66 (Year: 2010).*

Wang D L et al. (2011) "Room-Temperature Chemiresistive Effect of Ti02-B Nanowires to Nitroaromatic and Nitroamine Explosives, " Sensors Journal. IEEE 11(6): 1352-1358 (Year: 2011).*

Royer S and Duprez D (2011) "Catalytic Oxidation of Caibon Monoxide over Transition Metal Oxides," ChemCatChem 3:24-65 (Year: 2011).*

Aluri G S et al. (2011) "Highly selective GaN-nanowire/Ti02-nanocluster hybrid sensors for detection of benzene and related environment pollutants." Nanotechnology 22(29):295503 (Year: 2011).*

Islam M M et al. (2011) "Hydrogen adsorption and diffusion on the anatase TiOi (101) surface: a first-principles investigation." J. Phvs. Chem. C 115:6809-6814 (Year: 2011).*

Field C R et al. (2011) "Vapor detection performance of vertically aligned, ordered arrays of silicon nanowires with a porous electrode" Anal. Chem. 83(12):4724-8 (Year: 2011).*

Bajpai R et al. (2012) "UV-assisted alcohol sensing using Sn02 functionalized GaN nanowire devices," Sens. Actuators B. Chem. (article in press):499-507 (Year: 2012).*

Aluri G S et al. (2012) "Methanol, ethanol and hydrogen sensing using metal oxide and metal (Ti02-Pt) composite nanoclusters on GaN nanowires: a new route towards tailoring the selectivity of nanowire/nanocluster chemical sensors " Nanotechnology 22: 175501 (Year: 2012).*

Ahn H et al. (2010) *"Vertically Aligned Nanorod Sensor on Flexible Substrate for Ethanol Gas Monitoring,"* Electrochem. Solid-State Lett. 13:J125-J128.

Aluri G S et al. (2011) *"Highly selective GaN-nanowire/TiO2-nanocluster hybrid sensors for detection of benzene and related environment pollutants,"* Nanotechnology 22(29):295503 (11 pages).

Aluri G S et al. (2012) *"Methanol, ethanol and hydrogen sensing using metal oxide and metal (TiO2—Pt) composite nanoclusters on GaN nanowires: a new route towards tailoring the selectivity of nanowire/nanocluster chemical sensors,"* Nanotechnology 22:175501(12 pages).

Anpo M et al. (1989) *"In situ photoluminescence of titania as a probe of photocatalytic reactions,"* The Journal of Physical Chemistry 93(21):7300-7302.

Anpo M et al. (1999) *"Generation of superoxide ions at oxide surfaces,"* Top. Catal. 8:189-198.

Azad A M et al. (1992) *"Solid-State Sensors: A Review,"* J. Electrochem. Soc. 139(12):3690-3704.

Bajpai R et al. (2012) *"UV-assisted alcohol sensing using SnO2 functionalized GaN nanowire devices,"* Sens. Actuators B, Chem. (article in press):499-507.

Balázsi C et al. (2008) *"Novel hexagonal WO3 nanopowder with metal decorated carbon nanotubes as NO2 gas sensor,"* Sensors and Actuators B: Chemical 133:151-155.

Bertness K A et al. (2007) *"Nucleation conditions for catalyst free GaN nanowires,"* Journal of Crystal Growth 300:94-99.

Bertness K A et al. (2008) *"Mechanism for spontaneous growth of GaN nanowires with molecular beam epitaxy,"* J. Cryst. Growth 310(13):3154-3158.

Bikondoa O et al. (2006) *"Direct visualization of defect-mediated dissociation of water on $TiO_2$ (110),"* Nat. Mater. 5:189-192.

Brahim S et al. (2009) *"Carbon nanotube-based ethanol sensors,"* Nanotechnology 20:235502.

Brattain J B W H (1952) "Surface properties of germanium," Bell. Syst. Tech. Journal 32:1.

Butler E C and Davis A P (1993) *"Photocatalytic oxidation in aqueous titanium dioxide suspensions- the influence of dissolved transition metals,"* J. Photochem. Photobiol. A 70:273-283.

Calatayud M et al. (2003) *"Adsorption on perfect and reduced surfaces of metal oxides,"* Catalysis Today 85:125-143.

Carp O et al. (2004) *"Photoinduced reactivity of titanium dioxide,"* Prog. Solid St. Chem. 32:33-177.

Chang S-J et al. (2008) *"Highly sensitive ZnO nanowire CO sensors with the adsorption of Au nanoparticles,"* Nanotechnology 19:175502.

Chen Y et al. (2006) *"The enhanced ethanol sensing properties of multi-walled carbon nanotubes/$SnO_2$ core/shell nanostructures,"* Nanotechnology 17:3012-3017.

(56) References Cited

PUBLICATIONS

Chen Y J et al. (2006) "*Linear ethanol sensing of SnO2 nanorods with extremely high sensitivity,*" Applied Physics Letters 88:083105 (3 pages).

Comini E et al. (2002) "*Stable and highly sensitive gas sensors based on semiconducting oxide nanobelts,*" Appl. Phys. Lett. 81:1869 (3 pages).

Conner W C et al. (1995) "*Spillover in heterogeneous catalysis,*" Chem. Rev. 95:759-788.

Cui Y et al. (2001) "*Nanowire Nanosensors for Highly Sensitive and Selective Detection of Biological and Chemical Species,*" Science 293:1289-1292.

de Lacy Costello B P J et al (2008) "*Highly sensitive room temperature sensors based on the UV-LED activation of zinc oxide nanoparticles,*" Sens. Actuators B, Chem. 134(2):945-952.

de Lara-Castells M P And Krause J L (2003) "*Theoretical study of the UV-induced desorption of molecular oxygen from the reduced $TiO_2$ (110) surface,*" J. Chem. Phys. 118:5098.

Dobrokhotov V et al. (2006) "*Principles and mechanisms of gas sensing by GaN nanowires functionalized with gold nanoparticles,*" J. Appl. Phys 99:104302.

Du X et al. (2002) "*A New Highly Selective H2 Sensor Based on TiO2/PtO-Pt Dual-Layer Films,*" Chem. Mater. 14:3953-3957.

Duy N V et al. (2008) "*Mixed $SnO_2/TiO_2$ Included with Carbon Nanotubes for Gas-Sensing Application,*" J. Physica E 41:258-263.

Engel Y et al. (2010) "*Supersensitive Detection of Explosives by Silicon Nanowire Arrays,*" Angewandte Chemie International Edition 49(38):6830-6835.

Eranna G et al. (2004) "*Oxide Materials for Development of Integrated Gas Sensors—A Comprehensive Review/Integrated Gas Sensors—A Comprehensive Review,*" Critical Reviews in Solid State and Material Sciences 29:111-188.

Field C R et al. (2011) "*Vapor detection performance of vertically aligned, ordered arrays of silicon nanowires with a porous electrode,*" Anal. Chem. 83(12):4724-8.

Fujishima A et al. (2008) "*$TiO_2$ photocatalysis and related surface phenomena,*" Surf. Sci. Rep. 63:515-582.

Garzella C et al. (2000) "*$TiO_2$ thin films by a novel sol—gel processing for gas sensor applications,*" Sens. and Actuators B: Chemical 68:189-196.

Gong J et al. (2008) "*Micromachined sol—gel carbon nanotube/SnO2 nanocomposite hydrogen sensor,*" Sensors and Actuators B: Chemical 130:829-835.

Göpel, W. (1994) "*New materials and transducers for chemical sensors,*" Sensors and Actuators B: Chemical 18(1-3):1-21.

Heimer T A et al. (1993) "*Molecular level photovoltaics: the electrooptical properties of metal cyanide complexes anchored to titanium dioxide,*" J. Phys. Chem. 97:11987-11994.

Henderson M A et al. (1999) "*Interaction of Molecular Oxygen with the Vacuum-Annealed TiO2(110) Surface: Molecular and Dissociative Channels,*" J. Phys. Chem. B 103:5328-5337.

Henderson M A et al. (1999) "*The chemistry of methanol on the $TiO_2$ (110) surface: the influence of vacancies and coadsorbed species,*" Faraday Discuss. 114:313-329.

Herman G S et al. (2003) "*Experimental Investigation of the Interaction of Water and Methanol with Anatase-TiO2(101),*" J. Phys. Chem. B 107:2788-2795.

Hiehata K et al. (2007) "Local work function analysis of $Pt/TiO_2$ photocatalyst by a Kelvin probe force microscope,*" Nanotechnology 18:084007 (6 pages).

Hoffman M R et al. (1995) "*Environmental Applications of Semiconductor Photocatalysis,*" Chem. Rev. 95:69-96.

Huang X J and Choi Y K (2007) "*Chemical sensors based on nanostructured materials,*" Sens. Actuators B, Chem. 122(2):659-671.

Ioannides T and Verykios X E (1996) "*Charge Transfer in Metal Catalysts Supported on Doped $TiO_2$: A Theoritical Approach Based on Metal-Semiconductor Contact Theory,*" Journal of Catalysis 161:560-569.

Islam M M et al. (2011) "Hydrogen adsorption and diffusion on the anatase $TiO_2$ (*101*) surface: a first-principles investigation," J. Phys. Chem. C 115:6809-6814.

Jamieson J C and Olinger B (1969) "*Pressure-temperature studies of anatase, brookite, rutile, and $TiO_2$ (II); A discussion,*" Am. Min. 54:1477-1480.

Janata J (1992) "*Chemical Sensors,*" Anal. Chem. 64(12):196-219.

Joshi R K and Kruis F E (2006) "*Influence of Ag particle size on ethanol sensing of $SnO_{1.8}$:Ag nanoparticle films: A method to develop parts per billion level gas sensors,*" Appl. Phys. Lett. 89:153116.

Kamat P V (2002) "*Photophysical, photochemical and photocatalytic aspects of metal nanoparticles,*" The Journal of Physical Chemistry B 106(32):7729-7744.

Kim K S and Barteau M A (1989) "Reaction of Methanol on $TiO_2$," Surface Science 223:13-32.

Kong J et al. (2000) "*Nanotube Molecular Wires as Chemical Sensors,*" Science 287:622-625.

Kuang Q et al. (2008) "Enhancing the photon- and gas-sensing properties of a single SnO2 nanowire based nanodevice by nanoparticle surface functionalization," J. Phys. Chem. C 112:11539-11544.

Lao C S et al. (2007) "*Giant Enhancement in UV Response of ZnO Nanobelts by Polymer Surface-Functionalization,*" J. Am. Chem. Soc. 129:12096-12097.

Lee F K et al. (2007) "*Role of water adsorption in photoinduced superhydrophilicity on $TiO_2$ thin films,*" Appl. Phys. Lett. 90:181928.

Leghrib R et al. (2010) "*Gas sensors based on multiwall carbon nanotubes decorated with tin oxide nanoclusters,*" Sens. and Actuators B: Chemical 145:411-416.

Li C et al. (2003) "$In_2O_3$ nanowires as chemical sensors," Appl. Phys. Lett. 8:1613-1615.

Li M et al. (1999) "*Oxygen-induced restructuring of rutile $TiO_2$ (110): formation mechanism, atomic models, and influence on surface chemistry,*" Faraday Discuss. 114:245-258.

Lim W et al. (2008) "*Room temperature hydrogen detection using Pd-coated GaN nanowires,*" Appl. Phys. Lett. 93:072109.

Linsbigler A L et al. (1995) "*Photocatalysis on TiO2 Surfaces: Principles, Mechanisms, and Selected Results,*" Chem. Rev. 95:735-758.

Liu J et al. (2005) "*Vanadium Pentoxide Nanobelts: Highly Selective and Stable Ethanol Sensor Materials,*" Advanced Materials 17:764-767.

Luo Y and Ollis D F (1996) "*Heterogeneous photocatalytic oxidation of trichloroethylene and toluene mixtures in air: Kinetic promotion and inhibition, time-dependent catalyst activity,*" J. Catal. 163:1-11.

Lupan O et al. (2010) "*Selective hydrogen gas nanosensor using individual ZnO nanowire with fast response at room temperature,*" Sensors and Actuators B: Chemical 144:56-66.

Mansfield LM et al. (2009) "*GaN nanowire carrier concentration calculated from light and dark resistance measurements,*" Journal of Electronic Materials 38:495-504.

Mao Y et al. (1991) "*Identification of organic acids and other intermediates in oxidative degradation of chlorinated ethanes on titania surfaces en route to mineralization: a combined photocatalytic and radiation chemical study,*" J. Phys. Chem. 95:10080-10089.

McAlpine M C et al. (2007) "*Highly ordered nanowire arrays on plastic substrates for ultrasensitive flexible chemical sensors,*" Nat Mater 6:379-384.

Meixner H and Lampe U (1996) "*Metal oxide sensors,*" Sens. and Actuators B 33:198-202.

Meyer G J et al. (1988) "*Evidence for adduct formation at the semiconductor-gas interference. Photoluminsecent properties of cadmium selenide in the presence of amines,*" J. Am. Chem. Soc. 110:4914-4918.

Mills A and Hunte S L (1997) "*An overview of of semiconductor photocatalysis,*" J. Photochem. Photobiol. A 108:1-35.

Moore, D.S. (2004) "*Instrumentation for trace detection of high explosives,*" Review of Scientific Instruments 75(8):2499-2512.

Morikawa T et al. (2008) "*Visible-light-induced photocatalytic oxidation of carboxylic acids and aldehydes over N-doped $TiO_2$ loaded with Fe, Cu or Pt,*" Applied Catalysis B: Environmental 83:56-62.

(56) References Cited

PUBLICATIONS

Morrison S R (1987) "Selectivity in Semiconductor Gas Sensors," Sens. and Actuators 12:425-440.

Motayed A et al. (2003) "Electrical, thermal, and microstructural characteristics of Ti/Al/Ti/Au multilayer ohmic contacts to n-type GaN," J. Appl. Phys. 93(2):1087-1094.

Motayed A et al. (2006) "Realization of reliable GaN nanowire transistors utilizing dielectrophoretic alignment technique," J. Appl. Phy. 100:114310.

Mubeen S et al. (2010) "Sensitive detection of H2S using gold nanoparticle decorated single-walled carbon nanotubes," Anal. Chem. 82:250-257.

Navrotsky A et al. (1967) "Enthalpy of Transformation of a High-Pressure Polymorph of Titanium Dioxide to the Rutile Modification," Science 158:388.

Nicoletti S et al. (2003) "Use of Different Sensing Materials and Deposition Techniques for Thin-Film Sensors to Increase Sensitivity and Selectivity," IEEE Sensors Journal 3:454-459.

Norton P R and Richards P J (1974) "The heat of adsorption of hydrogen on platinum," Surface Science 44:129-140.

Nosaka Y et al. (1998) "Factors governing the initial process of TiO2 photocatalysis studied by means of in situ electron spin resonance measurements," J. Phys. Chem. B 102:10279-10283.

Offermans P et al. (2010) "Gas detection with vertical InAs nanowire arrays," Nano Lett. 10:2412-2415.

Parmeter J E (2004) "The challenge of standoff explosives detection," in 38th Annual 2004 International Carnahan Conference on Security Technology, 355-358.

Perkins C L and Henderson M A (2001) "Photodesorption and Trapping of Molecular Oxygen at the $TiO_2$ (110)—Water Ice Interface," J. Phys. Chem. B. 105:3856-3863.

Prades J D et al. (2009) "Equivalence between thermal and room temperature UV light-modulated responses of gas sensors based on individual SnO2 nanowires," Sens. Actuators B, Chem. 140(2):337-341.

Raible I et al. (2005) "$V_2O_5$ nanofibers: novel gas sensors with extremely high sensitivity and selectivity to amines," Sens. and Actuators B 106:730-735.

Ramgir N S et al. (2010) "Nanowire-based sensors," Small 6:1705-1722.

Royer S and Duprez D (2011) "Catalytic Oxidation of Carbon Monoxide over Transition Metal Oxides," ChemCatChem 3:24-65.

Ruiz A M et al. (2005) "Effects of various metal additives on the gas sensing performances of $TiO_2$ nanocrystals obtained from hydrothermal treatments," Sensors and Actuators B: Chemical 108:34-40.

Saeys M et al. (2002) "Density Functional Study of Benzene Adsorption on Pt111," J. Phys. Chem. B 10:7489-7498.

Sanford N A et al. (2010) "Steady-state and transient photoconductivity in c-axis GaN nanowires grown by nitrogen-plasma-assisted molecular beam epitaxy," J. Appl. Phy. 107:034318.

Sberveglieri G et al. (2007) "Synthesis and characterization of semiconducting nanowires for gas sensing," Sensors and Actuators B: Chemical 121:208-213.

Senesac L and Thundat TG, (2008) "Nanosensors for trace explosive detection," Materials Today 11(3):28-36.

Sexton B A et al. (1982) "Decomposition pathway of $C_1$ C4 alcohols adsorbed on platinum (111)," Surface Science 121:181-198.

Shen Y et al. (2009) "Hydrogen sensors made of undoped and Pt-doped $SnO_2$ nanowires," Journal of Alloys and Compounds 488:L21-L25.

Shimizu Y and Egashira M (1999) "Basic Aspects and Challenges of Semiconductor Gas Sensors," Mater. Res. Soc. Bull. 24:18-24.

Sippel-Oakley J et al. (2005) "Carbon nanotube films for room temperature hydrogen sensing," Nanotechnology 16:2218-2221.

Skucha K et al. (2010) "Palladium/silicon nanowire Schottky barrier-based hydrogen sensors," Sensors and Actuators B: Chemical 145:232-238.

Sun Y and Wang HH (2007) "High-Performance, Flexible Hydrogen Sensors That Use Carbon Nanotubes Decorated with Palladium Nanoparticles," Advanced Materials 19:2818-2823.

Tanaka K et al. (1991) "Effect of crystallinity of TiO2 on its photocatalytic action," Chem. Phys. Lett. 187:73-76.

Tang H et al. (1994) "Electrical and optical properties of $TiO_2$ anatase thin films," J. Appl. Phys. 75:2042-2047.

Thompson T L and Yates J T Jr. (2006) "Control of a surface photochemical process by fractal electron transport across the surface: O(2) photodesorption from TiO(2)(110)," J. Phys. Chem. B 110:7431-7435.

Wahab H S et al. (2008) "Computational investigation of water and oxygen adsorption on the anatase $TiO_2$ (100) surface," J. Mol. Chem. Struct. :THEOCHEM 868:101-108.

Wan Q et al. (2004) "Fabrication and ethanol sensing characteristics of ZnO nanowire gas sensors," Appl. Phys. Lett. 84:3654-3656.

Wang C et al. (2005) "Detection of $H_2S$ down to ppb levels at room temperature using sensors based on ZnO nanorods," Sens. and Actuators B 113:320-323.

Wang D L et al. (2011) "Room-Temperature Chemiresistive Effect of TiO2-B Nanowires to Nitroaromatic and Nitroamine Explosives," Sensors Journal, IEEE 11(6):1352 —1358.

Wang G C et al. (2005) "Characterization of methoxy adsorption on some transition metals: A first principles density functional theory study," J. Chem. Phys. 122:044707 (8 pages).

Wang H T et al. (2005) "Hydrogen-selective sensing at room temperature with ZnO nanorods," Appl. Phys. Lett. 86:243503.

Wilson D M et al. (2001) "Chemical Sensors for Portable, Handheld Field Instruments," IEEE Sensors Journal 1:256-274.

Wu R J et al. (2008) "Application of m-CNTs/NaClO4/Ppy to a fast response, room working temperature ethanol sensor," Sensors and Actuators B: Chemical 134:213-218.

Wu W-Y et al. (2009) "Electrospun ZnO Nanowires as Gas Sensors for Ethanol Detection," Nanoscale Research Letters 4:513-517.

Xue XY et al. (2006) "Synthesis and ethanol sensing properties of indium-doped tin oxide nanowires," Applied Physics Letters 88:201907.

Yamakata A et al. (2002) "Electron- and hole-capture reactions on Pt/TiO2 photocatalyst exposed to methanol vapor studied with time-resolved infrared absorption spectroscopy," J. Phys. Chem. B 106:9122-9125.

Yang Y Z et al. (2006) "Photo-Catalytic Production of Hydrogen Form Ethanol over M/TiO2 Catalysts (M = Pd, Pt or Rh)," Applied Catalysis B: Environmental 67:217-222.

Yates Jr J T (2009) "Photochemistry on TiO2: mechanisms behind the surface chemistry," Surf. Sci. 603:1605-1612.

Yinon, J. (2002) "Field detection and monitoring of explosives," TrAC Trends in Analytical Chemistry 21(4): 292-301.

Zalkind S et al. (2008) "Interaction of benzene with $TiO_2$ surfaces: Relevance to contamination of extreme ultraviolet lithography mirror capping layers," J. Vac. Sci. Technol. B 26:2241-2246.

Zhang D et al. (2004) "Detection of $NO_2$ down to ppb levels using individual and multiple $In_2O_3$ nanowire devices," Nano. Lett. 4:1919-1924.

Zhang H Z and Banfield J. F (1998) "Thermodynamic analysis of phase stability of nanocrystalline titania," J. Mater. Chem. 8:2073-2076.

Zhang H Z and Banfield J. F (2000) "Understanding polymorphic phase transformation behavior during growth of nanocrystalline aggregates: insights from TiO2," J. Phys. Chem. B 104:3481-3487.

Zhang Y et al. (2010) "Decoration of ZnO nanowires with Pt nanoparticles and their improved gas sensing and photocatalytic performance," Nanotechnology 21:285501.

Zhdanov V P (2002) "Nm-sized metal particles on a semiconductor surface, Schottky model, etc." Surface Science 512:L331-L334.

Zywietz et al. (1999) "The adsorption of oxygen at GaN surfaces," Appl. Phys. Lett. 74:1695-1697.

\* cited by examiner

Figure 1
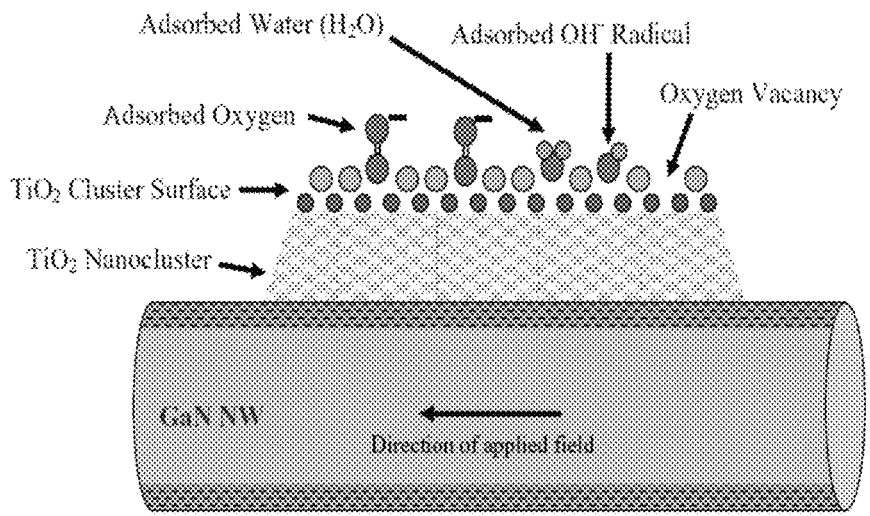
(a)
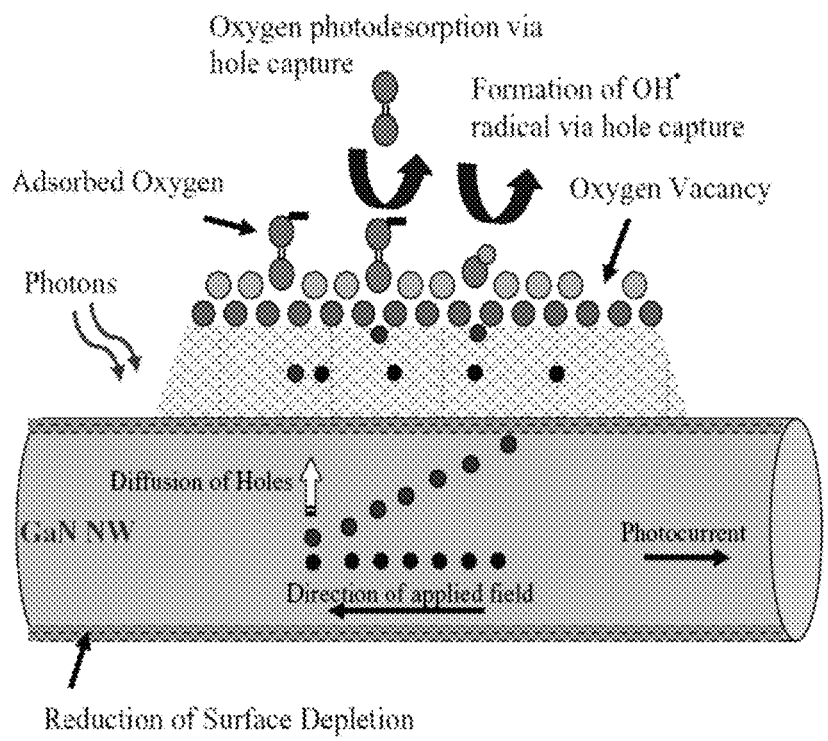
(b)

Figure 22
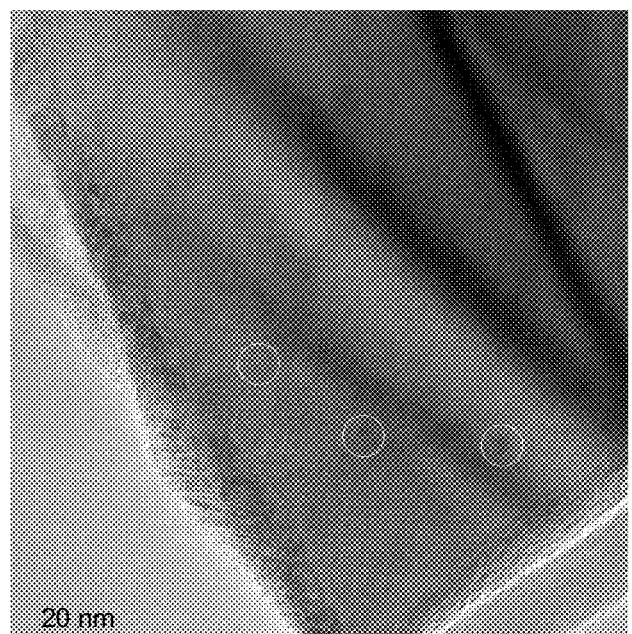
(a)
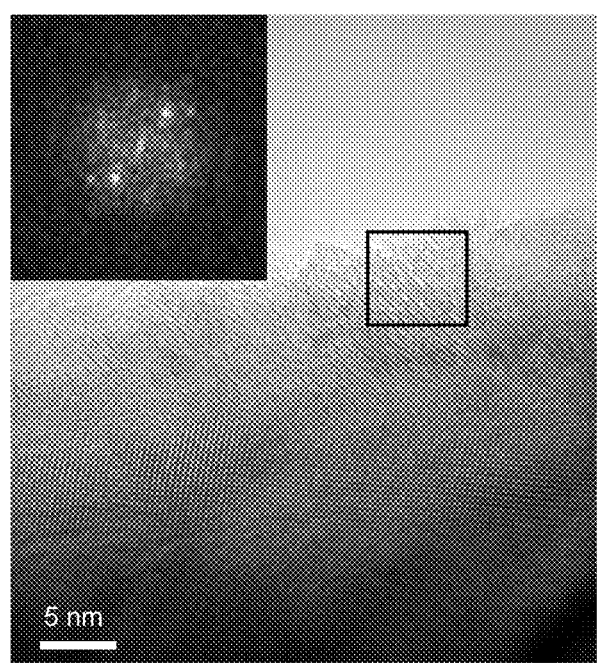
(b)

Figure 30
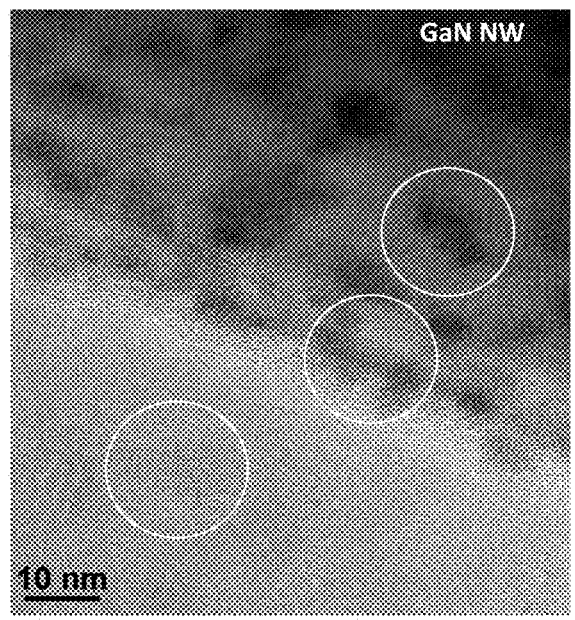
(a)
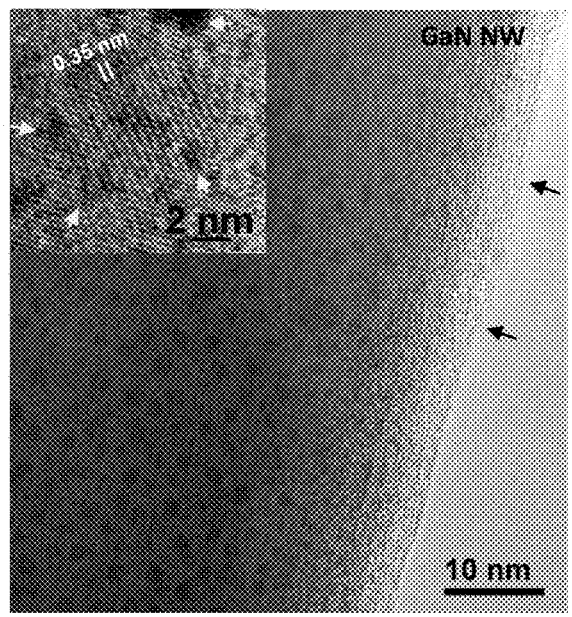
(b)

Figure 31
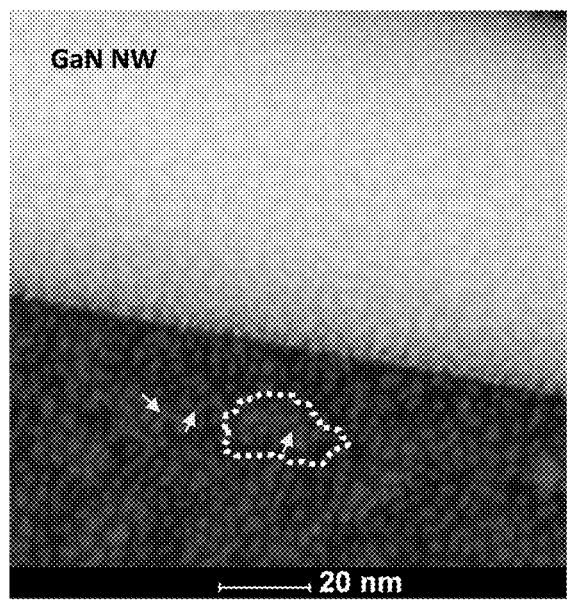
(a)
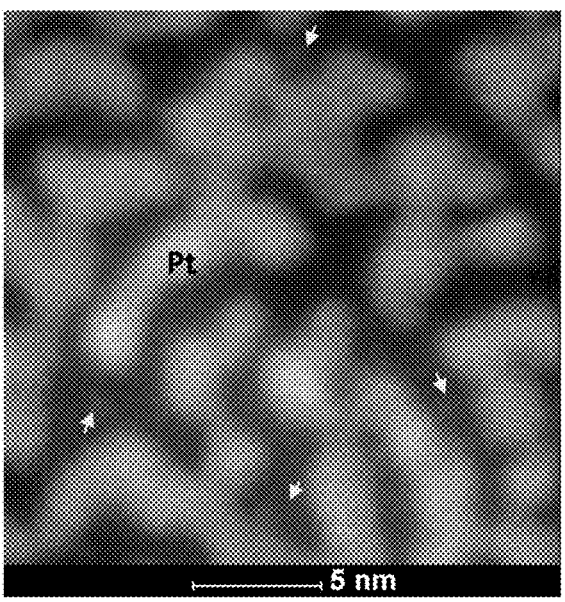
(b)

Figure 35
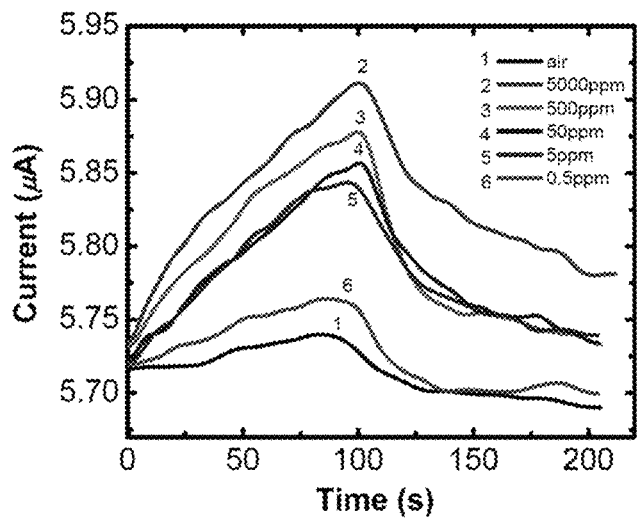
(a)
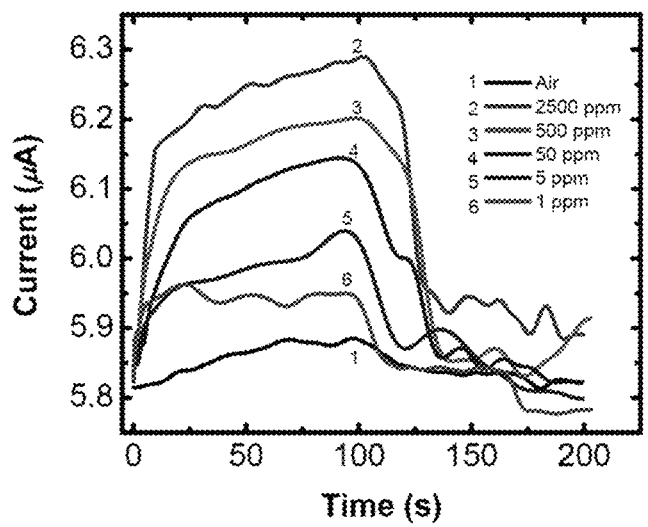
(b)

Figure 36
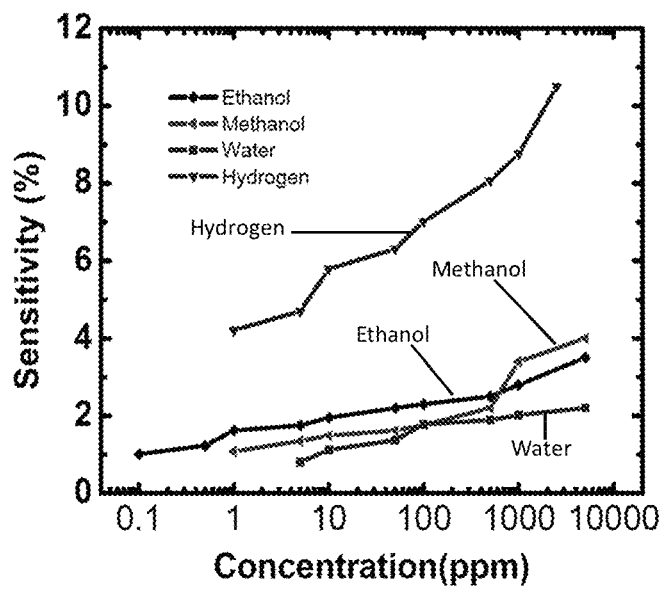
(a)
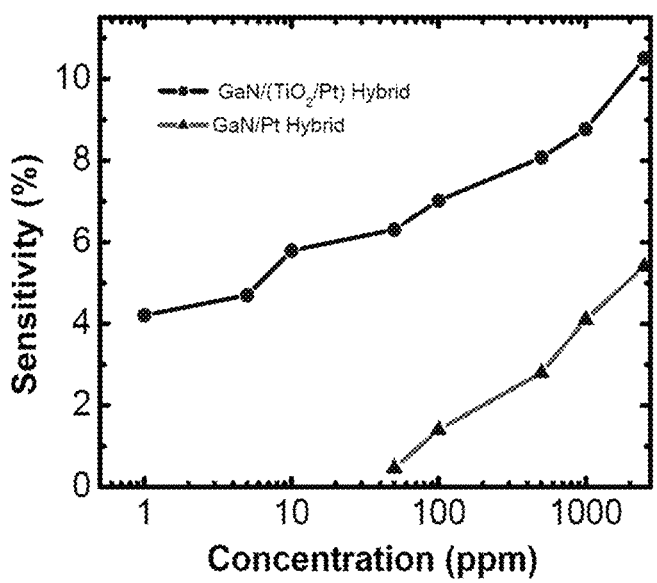
(b)

Figure 37

Deep UV Lithography

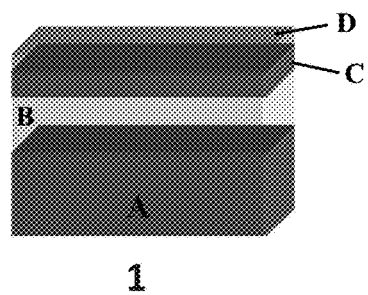

1

Negative Resist Profile

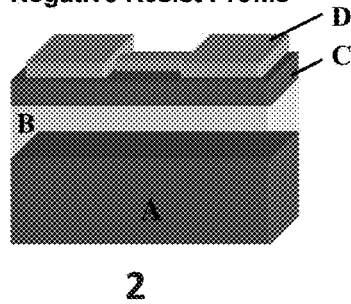

2

Pattern Transfer to Oxide Using Oxide Etch Using RIE

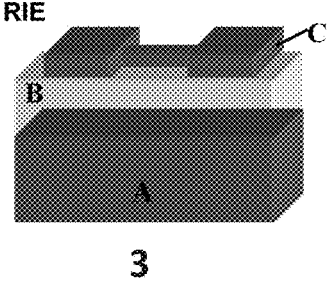

3

Pattern Transfer to Semiconductor Epilayer Using ICP

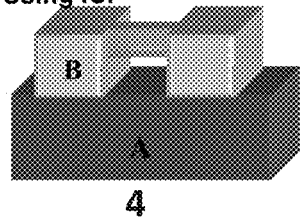

4

Removal of Plasma Damage Using Wet Etching

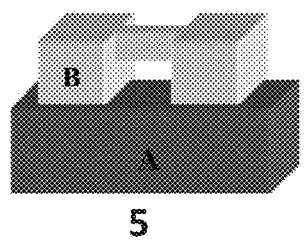

5

Ohmic Contact Deposition

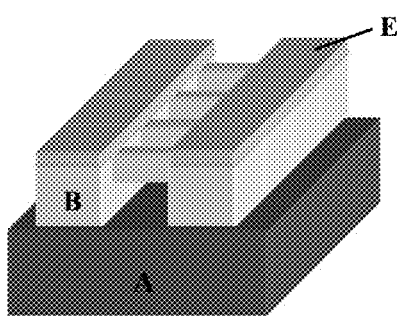

6

Mutlicomponent Nanocluster Deposition

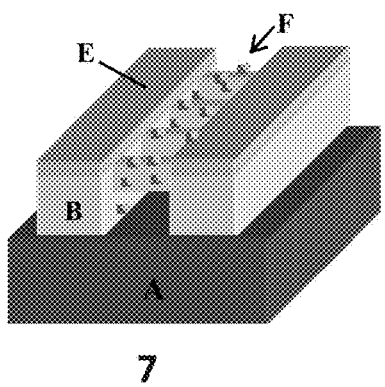

7

A - Si/Sapphire substrate
B - Direct-gap semiconductor (e.g. GaN) epilayer (1–1.5 microns thick)
C - Plasma-enhanced chemical deposition silicon dioxide
D - Ni mask for dry etch (suitable for nitrides composite with PECVD silicon dioxide)
E - Contact Electrode Stack
F - Nanoclusters (Oxide and metals)

Figure 38
(a)
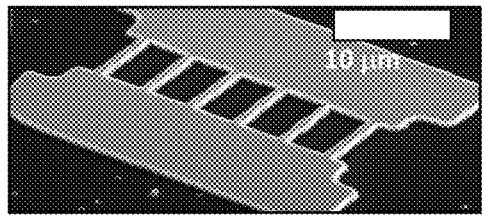
(b)
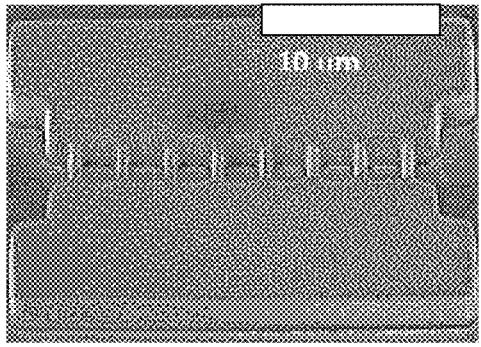
Figure 39
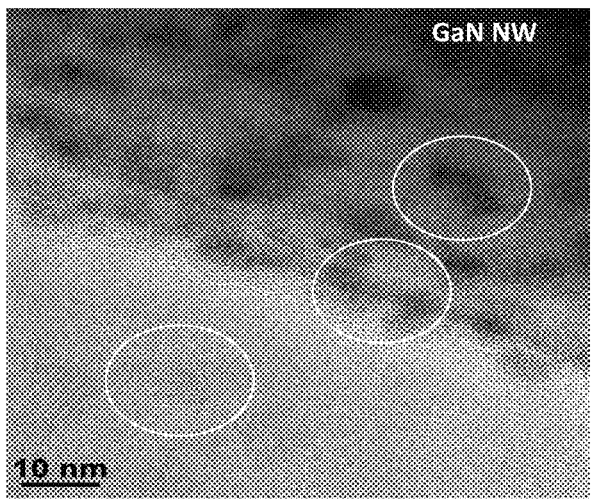

Figure 41
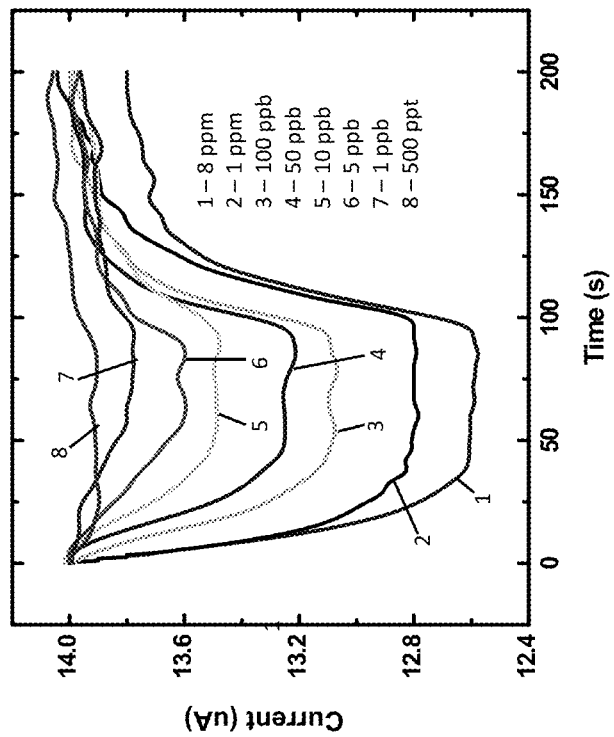
(b)
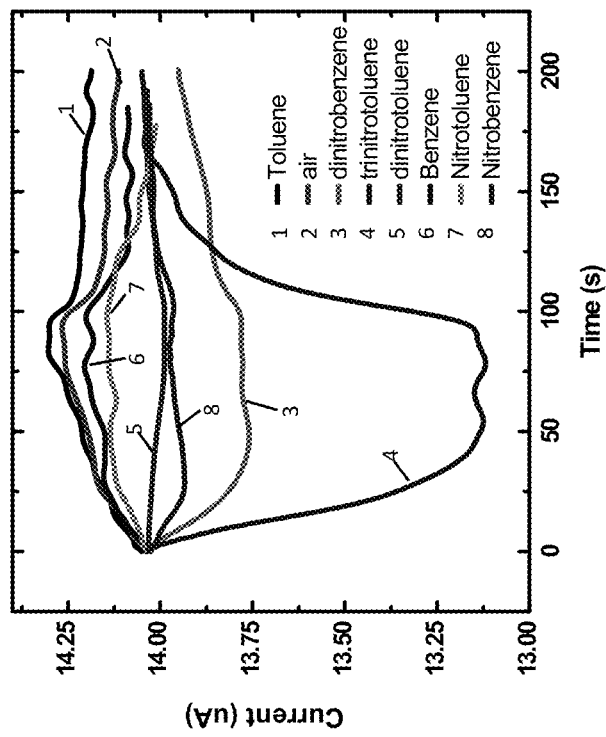
(a)

Figure 45
a) Breathing air in dark
b) Breathing air under UV
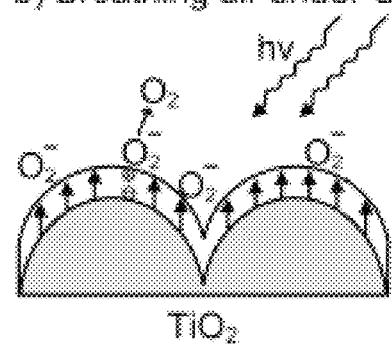
c) NO₂ under UV
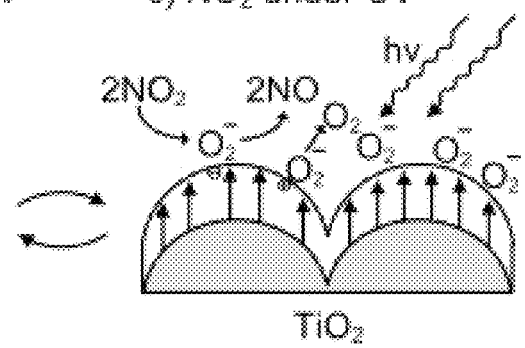
Figure 46
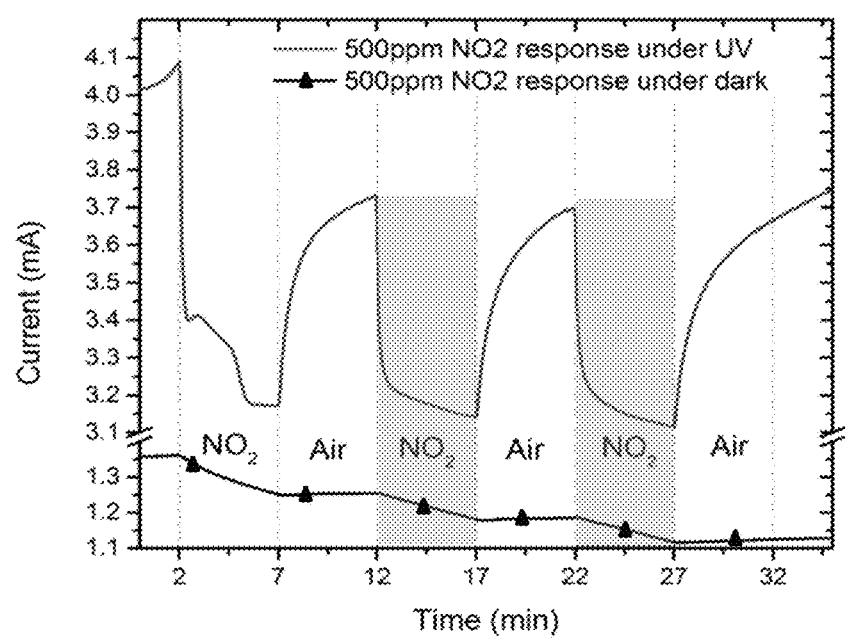

500 parts per million NO$_2$ in Air (22 °C, RH 0 – 5%)

10 parts per million SO$_2$ in Air (22 °C, 5000 parts per million CO$_2$ in Air (22

DEVICE HAVING AN ARRAY OF SENSORS ON A SINGLE CHIP

CROSS-REFERENCE TO RELATED APPLICATIONS

This application is a Continuation of U.S. patent application Ser. No. 15/297,693 (filed Oct. 19, 2016), which is a Continuation-in-part of U.S. patent application Ser. No. 13/861,962 (filed Apr. 12, 2013), now U.S. Pat. No. 9,476,862, which is based on U.S. Provisional Patent Application Ser. No. 61/623,957 (filed Apr. 13, 2012), Application Ser. No. 61/625,511 (filed Apr. 17, 2012), Application Ser. No. 61/730,865 (filed Nov. 28, 2012), and Application Ser. No. 61/775,305 (filed Mar. 8, 2013), which applications are all incorporated herein by reference in their entireties and to which priority is claimed.

STATEMENT REGARDING FEDERALLY SPONSORED RESEARCH OR DEVELOPMENT

This work was supported by the National Science Foundation (NSF) under ECCS-0901712 grant, by the Defense Threat Reduction Agency (DTRA) under HDTRA11010107, and by the National Institute of Standards and Technology (NIST) under SB134110SE0579 and SB1341 I 1SE0814. The US government has certain rights in this invention.

FIELD OF THE INVENTION

The present invention relates to a sensing device including a semiconductor nanostructure and at least one of metal or metal-oxide nanoparticles functionalizing the nanostructure and forming a hybrid sensor that enables light-assisted sensing of a target analyte.

BACKGROUND OF THE INVENTION

Detection of chemical species in air, such as industrial pollutants, poisonous gases, chemical fumes, and volatile organic compounds (VOCs), is vital for the health and safety of communities around the world (see Watson J and Ihokura K (1999) *Special issue on Gas-Sensing Materials*, Mater. Res. Soc. Bull. 24:14). The development of reliable, portable gas sensors that can detect harmful gases in real-time with high sensitivity and selectivity is therefore extremely important (Wilson D M et al. (2001) "*Chemical Sensors for Portable, Handheld Field Instruments*," IEEE Sensors Journal 1:256-274; Eranna G et al. (2004) "*Oxide Materials for Development of Integrated Gas Sensors—A Comprehensive Review/Integrated Gas Sensors—A Comprehensive Review*," Critical Reviews in Solid State and Material Sciences 29:111-188).

Due to their small size, ease of deployment, and low-power operation, solid-state thin film sensors are favored over analytical techniques such as optical and mass spectroscopy, and gas chromatography for real-time environmental monitoring (Wilson D M et al. (2001), supra, IEEE Sensor Journal 1:256-274; Shimizu Y and Egashira M (1999) "*Basic aspects and Challenges of Semiconductor Gas Sensors*," Mater. Res. Soc. Bull. 24:18; Sze S M (1994) Semiconductor Sensors 1$^{st}$ ed, Willey; New York). Selectivity, which is a sensor's ability to discriminate between the components of a gas mixture and provide detection signal for the component of interest, is an important consideration for the sensor's real-life applicability. Conventional metal-oxide based thin film sensors, despite decades of research and development (Brattain J B W H (1952) "*Surface properties of germanium*," Bell. Syst. Tech. Journal 32:1; Azad A M et al. (1992) "*Solid-State Sensors: A Review*," J. Electrochem. Soc. 139(12):3690-3704), still lack selectivity for different species and typically require high working temperatures (Meixner H and Lampe U (1996) "*Metal oxide sensors*," Sens. and Actuators B 33:198-202; Nicoletti S et al. (2003) "*Use of Different Sensing Materials and Deposition Techniques for Thin-Film Sensors to Increase Sensitivity and Selectivity*," IEEE Sensors Journal 3:454-459; Demarne V and Sanjines R (1992) Gas Sensors-Principles, Operation and Developments ed. G. Sberveglieri, Kluwer Academic, Netherlands). As such, the usability of such conventional sensors is severely limited and poses long-term reliability problems.

For a chemical sensor, the active surface area is an important factor for determining its detection limits or sensitivity. It is known that the electrical properties of nanowires (NWs) change significantly in response to their environments due to their high surface to volume ratio (Cui Y et al. (2001), supra, Science 293:1289-1292; Zhang D et al. (2004) "*Detection of $NO_2$ down to ppb levels using individual and multiple $In_2O_3$ nanowire devices*," Nano. Lett. 4:1919-1924; Kong J et al. (2000) "*Nanotube Molecular Wires as Chemical Sensors*," Science 287:622-625; Comini E et al. (2002) "*Stable and highly sensitive gas sensors based on semiconducting oxide nanobelts*," Appl. Phys. Lett. 81:1869). NWs are therefore well suited for direct measurement of changes in their electrical properties (e.g. conductance/resistance, impedance) when exposed to various analytes. Substantial research has demonstrated the enhanced sensitivity, reactivity, and catalytic efficiency of the nanoscale structures (Cui Y et al. (2001), supra, Science 293:1289; Li C et al. (2003) "*$In_2O_3$ nanowires as chemical sensors*," Appl. Phys. Lett. 8:1613; Wan Q et al. (2004) "*Fabrication and ethanol sensing characteristics of ZnO nanowire gas sensors*," Appl. Phys. Lett. 84:3654; Wang C et al. (2005) "*Detection of $H_2S$ down to ppb levels at room temperature using sensors based on ZnO nanorods*," Sens. and Actuators B 113:320-323; Wang H T et al. (2005) "*Hydrogen-selective sensing at room temperature with ZnO nanorods*," Appl. Phys. Lett. 86:243503; Raible I et al. (2005) "*$V_2O_5$ nanofibers: novel gas sensors with extremely high sensitivity and selectivity to amines*," Sens. and Actuators B 106:730-735; McAlpine M C et al. (2007) "*Highly ordered nanowire arrays on plastic substrates for ultrasensitive flexible chemical sensors*," Nat Mater 6:379-384).

There have been attempts to demonstrate sensors based on nanotube/nanowire decorated with nanoparticles of metal and metal-oxides. For example, Leghrib et al. reported gas sensors based on multiwall carbon nanotubes (CNTs) decorated with tin-oxide ($SnO_2$) nanoclusters for detection of NO and CO (see Leghrib R et al. (2010) "*Gas sensors based on multiwall carbon nanotubes decorated with tin oxide nanoclusters*," Sens. and Actuators B: Chemical 145:411-416). Using mixed $SnO_2/TiO_2$ included with CNTs, Duy et al. demonstrated ethanol sensing at a temperature of 250° C. (Duy N V et al. (2008) "*Mixed $SnO_2/TiO_2$ Included with Carbon Nanotubes for Gas-Sensing Application*," J. Physica E 41:258-263). Balázsi et al. fabricated hybrid composites of hexagonal $WO_3$ powder with metal decorated CNTs for sensing $NO_2$ (Balázsi C et al. (2008) "*Novel hexagonal $WO_3$ nanopowder with metal decorated carbon nanotubes as NO2 gas sensor*," Sensors and Actuators B: Chemical 133:151-155). Kuang et al. demonstrated an increase in the sensitivity of $SnO_2$ nanowire sensors to $H_2S$, CO, and $CH_4$ by surface functionalization with ZnO or NiO nanoparticles (Kuang Q et al. (2008) "*Enhancing the photon-and gas-sensing properties of a single $SnO_2$ nanowire based nanodevice by nanoparticle surface functionalization*," J. Phys. Chem. C 112:11539-11544). ZnO NWs decorated with Pt nanoparticles were utilized by Zhang et al., showing that the response of Pt nanoparticles decorated ZnO NWs to ethanol is three times higher than that of bare ZnO NWs (Zhang Y et al. (2010) "*Decoration of ZnO nanowires with Pt nanoparticles and their improved gas sensing and photocatalytic performance*," Nanotechnology 21:285501). Chang et al. showed that by adsorption of Au nanoparticles on ZnO NWs, the sensor sensitivity to CO gas could be enhanced significantly (Chang S-J et al. (2008) "*Highly sensitive ZnO nanowire CO sensors with the adsorption of Au nanoparticles*," Nanotechnology 19:175502). Dobrokhotov et al. constructed a chemical sensor from mats of GaN NWs decorated with Au nanoparticles and tested their sensitivity to $N_2$ and $CH_4$ (Dobrokhotov V et al. (2006) "*Principles and mechanisms of gas sensing by GaN nanowires functionalized with gold nanoparticles*," J. Appl. Phys 99:104302). GaN NWs coated with Pd nanoparticles were employed for the detection of $H_2$ in $N_2$ at 300K by Lim et al. (Lim W et al. (2008) "*Room temperature hydrogen detection using Pd-coated GaN nanowires*," Appl. Phys. Lett. 93:072109).

Although such results demonstrate the potentials of the nanowire-nanocluster based hybrid sensors, fundamental challenges and deficiencies in such prior attempts remain. Most of the results provide for mats of nanowires. Although such mats may increase sensitivity, the complex nature of inter-wire conduction makes interpreting the results difficult. Also, room-temperature operation of such previous sensors has not been demonstrated, and the selectivity is shown for only a very limited number of chemicals. Conventional sensor devices require high operating temperatures (250° C.) and large response times (more than 5 minutes). Indeed, such temperature-assisted sensors typically provide for an integrated heater for the device. Further, the reported sensitivities of such conventional devices were quite low even with long response times. Further, such conventional devices typically do not provide for air as the carrier gas. However, the ability of a sensor to detect chemicals in air is what ultimately determines its usability in real-life.

Thus, such demonstrations have resulted in poor selectivity of known chemical sensors, and therefore have not resulted in commercially viable gas sensors. For real-world applications, selectivity between different classes of compounds (such as between aromatic compounds and alcohols) is highly desirable. For example, the threat of terrorism and the need for homeland security call for advanced technologies to detect concealed explosives safely and efficiently. Detecting traces of explosives is challenging, however, because of the low vapor pressures of most explosives (Moore, D S (2004) "*Instrumentation for trace detection of high explosives*," Review of Scientific Instruments 75(8): 2499-2512; Yinon J (2002) "*Field detection and monitoring of explosives*," TrAC Trends in Analytical Chemistry 21(4): 292-301; Senesac L. and Thundat T G (2008) "*Nanosensors for trace explosive detection*," Materials Today 11(3):28-36. Moreover, the difficulty of explosive detection is aggravated by the noisy environment which masks the signal from the explosive, the potential for high false alarms, and the need to determine a threat quickly. As such, trained canine teams remain the most reliable means of detecting explosive vapors to date; however, dogs are expensive to train and tire easily.

An ideal chemical sensor would be able to distinguish between the individual analytes belonging to a particular class of compounds, e.g. detection of the presence of benzene or toluene in the presence of other aromatic compounds, detection of a particular explosive compound, detection of a particular alcohol, etc. This is extremely challenging as most semiconductor-based sensors use metal-oxides (such as $SnO_2$, $In_2O_3$, ZnO) as the active elements, which are limited due to the non-selective nature of the surface adsorption sites. The surface/adsorbate interactions of conventional sensor structures are limited and non-specific. Thus, conventional sensor devices lack the same selectivity as their bulk-counterpart devices.

Accordingly, there is a need for a nanostructure sensor device that solves one or more of the deficiencies of conventional devices.

SUMMARY OF THE INVENTION

The present invention is directed to highly selective and sensitive sensor devices including semiconductor nanostructures decorated with metal and/or metal-oxide nanoclusters or particles. The disclosed sensors provide numerous advantages over conventional sensors including: 1) light-induced room-temperature sensing as opposed to thermally induced sensing, providing for reliable operation at low-power, longer lifetime, and fast response/recovery time; 2) excellent selectivity of sensing of selected compounds (e.g., sensors able to distinguish toluene from other aromatic compounds); 3) wide sensing range (50 ppb-1%); 4) fast response and recovery; and 5) reliable and repeatable operation.

According to implementations of the present invention, hybrid chemiresistive architectures utilizing nanoengineered wide-bandgap semiconductor backbone functionalized with multicomponent photocatalytic nanoclusters of metal-oxides and/or metals are provided. Such implementations, e.g. providing for chip scale hybrid sensor architecture backbones, are particularly suitable for mass production employing industry standard fabrication techniques, such as for commercial applications. The sensors operate at room-temperature via photoenabled sensing, and utilize standard microfabrication techniques. Thus, economical, multianalyte single-chip sensors are achieved.

According to embodiments of the present invention, the disclosed semiconductor nanostructures exhibit relatively inactive surface properties (i.e., with little or no chemiresistive sensitivity to different classes of organic vapors). The nanostructures are functionalized with analyte-dependent active metal-oxides and/or metals. Photoconductive metal-oxide-semiconductors may be utilized as a functionalizing material due to their active surface properties and light-assisted sensing operation. Unlike most metal-oxide-based sensors that operate at high temperatures, the photoconductive hybrid sensor devices of the present invention enable rapid light-assisted sensing at temperatures well below 100° C., and in particular at temperatures between about 10° C. and 100° C., including at room temperature (e.g., between about 18° C. and about 24° C.). Thus, the disclosed sensors operate at temperatures well below that required by conventional oxide sensors (e.g., requiring sensing temperatures higher than 100° C.), thereby providing rapid sensing capabilities at room temperature assisted by UV light illumination.

According to one embodiment, a multi-analyte sensor comprises a substrate having an upper surface, a semiconductor nanostructure having an outer surface and disposed on the upper surface of the substrate, first metal-oxide nanoparticles functionalizing the outer surface of the semiconductor nanostructure and enabling detection of a target analyte in the presence of light, the first metal-oxide nanoparticles have a first adsorption profile, and second metal nanoparticles functionalizing the outer surface of the semiconductor structure. The second metal nanoparticles have a second adsorption profile. The target analyte preferentially adsorbs on the first metal-oxide, and an interfering analyte preferentially adsorbs on the second metal nanoparticles. The sensor exhibits a change in output upon detection of the target analyte, the output selected from the group consisting of current, voltage and resistance.

The disclosed sensors enable detection of the target analyte within various carrier gases, including air, nitrogen or argon. The semiconductor nanostructure may comprise gallium nitride (GaN), indium nitride (InN), aluminum gallium nitride (ALGaN), zinc oxide (ZnO), Indium arsenide (InAs). The metal-oxide nanoparticles may comprise one or more nanoparticles selected from the group consisting of titanium dioxide ($TiO_2$) nanoparticles, tin oxide ($SnO_2$) nanoparticles, zinc oxide (ZnO) nanoparticles, nickel oxide (NiO) nanoparticles, copper oxide ($Cu_xO_x$) nanoparticles, cobalt oxide ($Co_xO_x$) nanoparticles, iron oxide ($Fe_xO_x$) nanoparticles, zinc magnesium oxide ($Zn_{1-x}Mg_xO$) nanoparticles, magnesium oxide (MgO) nanoparticles, vanadium oxide ($V_xO_x$) nanoparticles, lanthanum oxide ($La_2O_3$) nanoparticles, zirconium oxide ($ZrO_2$) nanoparticles, aluminum oxide ($Al_2O_3$) nanoparticles, strontium oxide (SrO) nanoparticles, lanthanum oxide ($La_2O_3$) nanoparticles, cerium oxide ($Ce_xO_x$) nanoparticles, praseodymium oxide ($Pr_xO_x$) nanoparticles, promethium oxide ($Pm_2O_3$) nanoparticles, samarium oxide ($Sm_2O_3$) nanoparticles, europium oxide ($Eu_2O_3$) nanoparticles, gadolinium oxide ($Gd_2O_3$) nanoparticles, terbium oxide ($Tb_xO_x$) nanoparticles, dysprosium oxide ($Dy_2O_3$) nanoparticles, holmium oxide ($Ho_2O_3$) nanoparticles, erbium oxide ($Er_2O_3$) nanoparticles, thulium oxide ($Tm_2O_3$) nanoparticles, ytterbium oxide ($Yb_2O_3$) nanoparticles, and lutetium oxide ($Lu_2O_3$) nanoparticles.

The metal nanoparticles may comprise one or more nanoparticles selected from the group consisting of lithium nanoparticles, sodium nanoparticles, potassium nanoparticles, rubidium nanoparticles, cesium nanoparticles, francium nanoparticles, beryllium nanoparticles, magnesium nanoparticles, calcium nanoparticles, strontium nanoparticles, barium nanoparticles, radium nanoparticles, aluminum nanoparticles, gallium nanoparticles, indium nanoparticles, tin nanoparticles, thallium nanoparticles, lead nanoparticles, bismuth nanoparticles, scandium nanoparticles, titanium nanoparticles, vanadium nanoparticles, chromium nanoparticles, manganese nanoparticles, iron nanoparticles, cobalt nanoparticles, nickel nanoparticles, copper nanoparticles, zinc nanoparticles, yttrium nanoparticles, zirconium nanoparticles, niobium nanoparticles, molybdenum nanoparticles, technetium nanoparticles, ruthenium nanoparticles, rhodium nanoparticles, palladium nanoparticles, silver nanoparticles, cadmium nanoparticles, lanthanum nanoparticles, hafnium nanoparticles, tantalum nanoparticles, tungsten nanoparticles, rhenium nanoparticles, osmium nanoparticles, iridium nanoparticles, platinum nanoparticles, gold nanoparticles, mercury nanoparticles, and combinations or alloys thereof.

In disclosed embodiments, the sensors are capable of detecting a target analyte within a wide temperature range and/or within a wide humidity range. In addition, the disclosed sensors are capable of detecting a target analyte at a temperature of less than about 100° C. In some implementations, the sensors are capable of detecting a target analyte at room temperature (e.g., between about 18° C. and about 24° C.). In some implementations, the target analyte comprises a gas (e.g., $NO_2$, $H_2$, $CH_4$, $CO_2$, CO, $NH_3$, $O_2$, $SO_x$, $H_2S$, $Cl_2$, HCl and/or HCN). In some implementations, the target analyte is an alcohol vapor (e.g., methanol, ethanol, n-propanol, isopropanol, n-butanol, and isobutanol). In other embodiments, the target analyte is a volatile organic compound (VOC) (e.g., benzene, toluene, ethylbenzene, xylene, chlorobenzene, formaldehyde benzene, formaldehyde, methanol, ethanol, isopropanol, hexane, acetone, tetrachloroethylene (TCE), MTBE, methylene chloride, d-limonene, methylene chloride, an alkane (e.g., propane, butane), a ketone, a silane, a siloxane, and mixtures such as diesel/gasoline vapor). In other embodiments, the target analyte comprises a chemical warfare agent (CWA) (e.g., tabun (GA), sarin (GB), soman (GD), cyclosarin (GF), sulfur mustard (HD), nitrogen mustard (HN)), or another simulant chemical (e.g., Dimethyl methylphosphonate (DMMP), Triethyl phosphonate (TEP)).

The disclosed sensors are capable of detecting the target analyte at a concentration of less than about 1%. In some implementations, the concentration of the target analyte detected is between about 1 parts per million and about 50 parts per billion. In addition, the disclosed sensors are capable of detecting humidity from between about 0% to about 100% relative humidity (RH). In disclosed embodiments, the sensing device has a response and recovery time of less than about 180 seconds, preferably less than about 75 seconds.

The present invention is also directed to a nanostructure sensing device comprising a semiconductor nanostructure having an outer surface, and at least one of metal or metal-oxide nanoparticle clusters functionalizing the outer surface of the nanostructure. The dimensions and overall length of the sensing device may vary (e.g., from nanometer to centimeter scale). In some embodiments, the sensing device comprises a chip-scale package having dimensions of less than about 10 mm by 10 mm, e.g., about 4 mm by 4 mm or smaller. Thus, the sensor devices of the present invention are suitable for wearables and/or compact applications, and also reliable and robust and thus suitable for industrial applications and/or extreme conditions. The architecture may provide for a single sensing device or multiple sensing devices, e.g. connected in series or parallel. The resulting structure forms a photoconductive nanostructure/nanocluster hybrid sensor enabling light-assisted sensing of a target analyte.

In disclosed embodiments, the sensing device exhibits a change in current, resistivity and/or voltage upon exposure to a target analyte in the presence of UV light and/or visible light, with the magnitude of such change dependent on the configuration of the device. The architecture may provide for a single sensor, dual sensors or multiple sensors on a single chip (e.g., comprising nano-, micro-, or millimeter size wide-band gap oxide semiconductors) which are functionalized with metal oxide and/or metal nanoparticles and/or with their alloys. The architecture is thus capable of simultaneously detecting one, two, or multiple (e.g., 8 or more) analytes independently. The target analyte(s) interacts with the functionalized material in the presence of various carrier gases (e.g., air, oxygen, nitrogen, argon) that results in a change in current, resistance and/or voltage in the semiconductor backbone. For comparison, a chip consisting of a non-functionalized, passivated element mimicking the design architecture of the sensor element which is buried under an oxide acts as a baseline, and does not respond to any of the target analytes.

The semiconductor backbone may comprise etched/patterned ultra-thin nano-clustered metal oxide, e.g. comprised of zinc oxide (ZnO), titanium dioxide ($TiO_2$), tin oxide ($SnO_2$), nickel oxide (NiO), copper oxide, cobalt oxide, iron oxide, zinc magnesium oxide, magnesium oxide, vanadium oxide, lanthanum oxide, and/or zirconium oxide. The second metal oxide functionalization consists of another metal oxide, e.g. comprised of zinc oxide (ZnO), titanium dioxide ($TiO_2$), tin oxide ($SnO_2$), nickel oxide (NiO), copper oxide, cobalt oxide, iron oxide, zinc magnesium oxide, magnesium oxide, vanadium oxide, lanthanum oxide, and/or zirconium oxide.

Third metal nanoparticles may also be provided, e.g. comprised of lithium, sodium, potassium, rubidium, cesium, francium, beryllium, magnesium, calcium, strontium, barium, radium, aluminum, gallium, indium, tin, thallium, lead, bismuth, scandium, titanium, vanadium, chromium, manganese, iron, cobalt, nickel, copper, zinc, yttrium, zirconium, niobium, molybdenum, technetium, ruthenium, rhodium, palladium, silver, cadmium, lanthanum, hafnium, tantalum, tungsten, rhenium, osmium, iridium, platinum, gold, mercury, and combinations and alloys thereof.

In some implementations, the nanoparticle clusters are multicomponent clusters comprising first metal-oxide nanoparticles and second metal nanoparticles. The nanostructure has a first bandgap, and the nanoparticle clusters have a second bandgap equal to or less than said first bandgap. In disclosed embodiments, the devices exhibit increased conductivity upon exposure to the target analyte in the presence of radiation, including UV light and/or visible light.

BRIEF DESCRIPTION OF THE DRAWINGS

The patent or application file contains at least one drawing/photograph executed in color. Copies of this patent or patent application publication with color drawing(s) will be provided by the Office upon request and payment of the necessary fee.

FIG. 1, plates (a) and (b), are schematic representations of a GaN (Nanowire)-$TiO_2$ (Nanocluster) hybrid sensor according to the present invention. FIG. 1, plate (a) shows the sensor in the dark showing surface depletion of the GaN nanowire, and FIG. 1, plate (b) shows the sensor under UV excitation with photodesorption of $O_2$ due to hole capture.

FIG. 2, plate (b) illustrates the response of a hybrid device (diameter 500 nm) to different concentrations of water in air.

FIG. 5, plate (b) illustrates the cyclic response of the GaN/($TiO_2$—Pt) hybrid device when exposed to 2500 μmol/mol (ppm) of hydrogen in nitrogen. The bias voltage for all the devices was 5 V.

FIG. 6, plate (b) shows ZnO nanoparticles on the facets of GaN NW. FIG. 6, plate (c) illustrates graphically current-voltage (I-V) characteristics of the device before and after rapid thermal anneal (RTA). FIG. 6, plate (d) is an x-ray diffraction (XRD) Ω-2θ scan of a 300-nm-thick ZnO film.

FIG. 9, plate (b) illustrates schematically an exemplary thin-film device including a semiconductor backbone functionalized with $TiO_2$ on a sapphire substrate. The smoothness of the substrate and film after thermal processing is shown in FIG. 9, plates (c) and (d).

FIG. 22 illustrates typical morphologies of a 20 nm thick $TiO_2$ film sputtered on n-GaN nanowires and annealed at 700° C. for 30 s. FIG. 22, plate (a) is a TEM image showing non-uniformly distributed 2 nm to 10 nm diameter individual $TiO_2$ particles, with some of the particles marked by white circles. FIG. 22, plate (b) is a high-resolution transmission electron microscopy (HRTEM) image of an edge of the GaN nanowire with the sputtered $TiO_2$ film. The FFT pattern from the boxed area is shown in exploded view in the upper left inset, indicating 0.35 nm lattice fringes which are consistent with a (101) reflecting plane of anatase.

FIG. 23, plate (b) is an ADF-STEM image of a $TiO_2$-containing aggregate on the edge of a GaN nanowire. FIG. 23, plate (c) is an X-ray spectrum of an individual 5 nm $TiO_2$ particle shown by circled portion 'A' in plate (a). FIG. 23, plate (d) is an EEL spectra recorded on position 1 (tip of the aggregate) and position 2 (edge of the GaN nanowire), as identified in plate (b), respectively.

FIG. 25, plate (b) illustrates the dynamic photocurrent of a $TiO_2$ coated (8 nm deposit) GaN NW. The diameters of both nanowires were about 200 nm. The applied bias is 5 V in both cases.

FIG. 27, plate (b) illustrates the response of a different sensor (inset shows nanowire with diameter 300 nm) to 200 ppb toluene, benzene, ethylbenzene, and xylene with UV excitation. The total flow in to the chamber was kept constant at 20 sccm. The response to air is also shown. The scale bars are 5 µm.

FIG. 28, plate (a) shows the characteristics of the device shown in FIG. 27, plate (a) for 100 to 10000 ppm concentration range of toluene; FIG. 28, plate (b) shows the characteristics of the device shown in FIG. 27, plate (b) for 50 ppb to 1 ppm concentration range of toluene.

FIG. 30 is an HRTEM image of a GaN NW with $TiO_2$ sputtered on them, with plate (a) showing the GaN NW before Pt and plate (b) showing after Pt deposition. Circled areas in plate (a) indicate partially aggregated polycrystalline $TiO_2$ particles on the NW surface and on the supporting carbon film. Arrows in plate (b) in the inset at the upper left mark Pt clusters decorating a 6 nm diameter particle of titanium. The $TiO_2$ particle exhibits 0.35 nm fringes corresponding to (101) lattice spacing of anatase polymorph. 2 nm to 5 nm thick amorphized surface film are indicated by black arrows.

FIG. 31 illustrate an HAADF-STEM of a GaN NW coated with $TiO_2$ and Pt, with plate (a) showing 1 nm to 5 nm bright Pt nanoparticles (shown by arrows) decorating surfaces of a polycrystalline $TiO_2$ island-like film and of a GaN nanowire. Medium grey aggregated $TiO_2$ particles (outlined by dashed line in plate (a)) are barely visible on a thin carbon support near the edge of the nanowire. Plate (b) is a high magnification image of the supporting film near the edge of the nanowire exhibiting 0.23 nm to 0.25 nm (111) and 0.20 nm to 0.22 nm (200) fcc lattice fringes belonging to Pt nanocrystallites, with arrows indicating amorphous-like Pt clusters of 1 nm and less in diameter.

FIG. 32, plate (a) shows GaN/($TiO_2$—Pt) hybrids; FIG. 32, plate (b) shows GaN/Pt hybrids. The inset image in plate (b) shows the plan-view SEM image of a typical GaN NWNC hybrid sensor. The scale bar in the inset is 4 µm.

FIG. 35, plate (a) illustrates graphically the photo-response of GaN/($TiO_2$—Pt) hybrid device to different concentrations of methanol in air. FIG. 35, plate (b) shows photo-response of the same device to different concentrations of hydrogen in nitrogen. The air-gas mixture was turned on at 0 s and turned off at 100 s.

FIG. 36, plate (a) is a sensitivity plot of the GaN/($TiO_2$—Pt) hybrid device to ethanol, methanol, and water in air and to hydrogen in nitrogen ambient. FIG. 36, plate (b) shows graphically a comparison of the sensitivity of GaN/(TiO$_2$—Pt) and GaN/Pt devices to different concentrations of hydrogen in nitrogen.

FIG. 37 illustrates schematically an exemplary fabrication flow chart for semiconductor-nanocluster based gas sensors according to the present invention.

FIG. 38, plate (a) is an image of large area etched nanostructures of GaN on silicon and sapphire substrate formed according to disclosed processes such as shown in FIG. 37. FIG. 38, plate (b) shows an image of a nanostructure of GaN on silicon and sapphire using ICP etching and post-etching surface treatment. This nanostructure forms the backbone of the disclosed sensors in disclosed embodiments.

FIG. 39 is an RTEM image of a GaN NW with TiO$_2$ sputtered on them. Circled portions indicate partially aggregated polycrystalline TiO$_2$ particles on the NW surface and on the supporting carbon film.

FIG. 41, plate (a) illustrates graphically response of a single, nanowire-nanocluster hybrid sensor to 100 ppb of benzene, toluene, nitrobenzene, nitrotoluene, dinitrobenzene, dinitrotoluene and trinitrotoluene in the presence of UV excitation. FIG. 41, plate (b) shows the response of the device to different concentrations of trinitrotoluene.

FIG. 44, plate (a), illustrates the dynamic responses of a TiO$_2$ based sensor exposed to 250 ppm NO$_2$ mixed with breathing air under UV illumination and dark at room temperature. Plate (b) illustrates the response under UV at mixture of 100 ppm, 250 ppm, and 500 ppm with breathing air. The inset in plate (b) shows the measured responses under UV as a function of NO$_2$ concentrations with uncertainty. Sensitivity S is presented by $(I_g - I_\alpha) \times 100/I_\alpha$, wherein $I_g$ is the device current in the presence of an analyte in breathing air and/is the current in pure breathing air, both measured 300 s after the flow is turned on.

FIG. 45 illustrates schematically an NO$_2$ gas sensing mechanism of the TiO$_2$ sensor under UV illumination: plate (a) shows the mechanism in a dark environment with breathing air in; plate (b) shows the mechanism under UV illumination in breathing air; and plate (c) shows the mechanism under UV illumination with mixture of NO$_2$ and breathing air (all at room temperature).

FIG. 46 illustrates graphically the dynamic response of the TiO$_2$ based sensor exposed to 500 ppm NO$_2$ under UV illumination and under dark at room temperature.

DETAILED DESCRIPTION OF THE INVENTION

Figure 2:
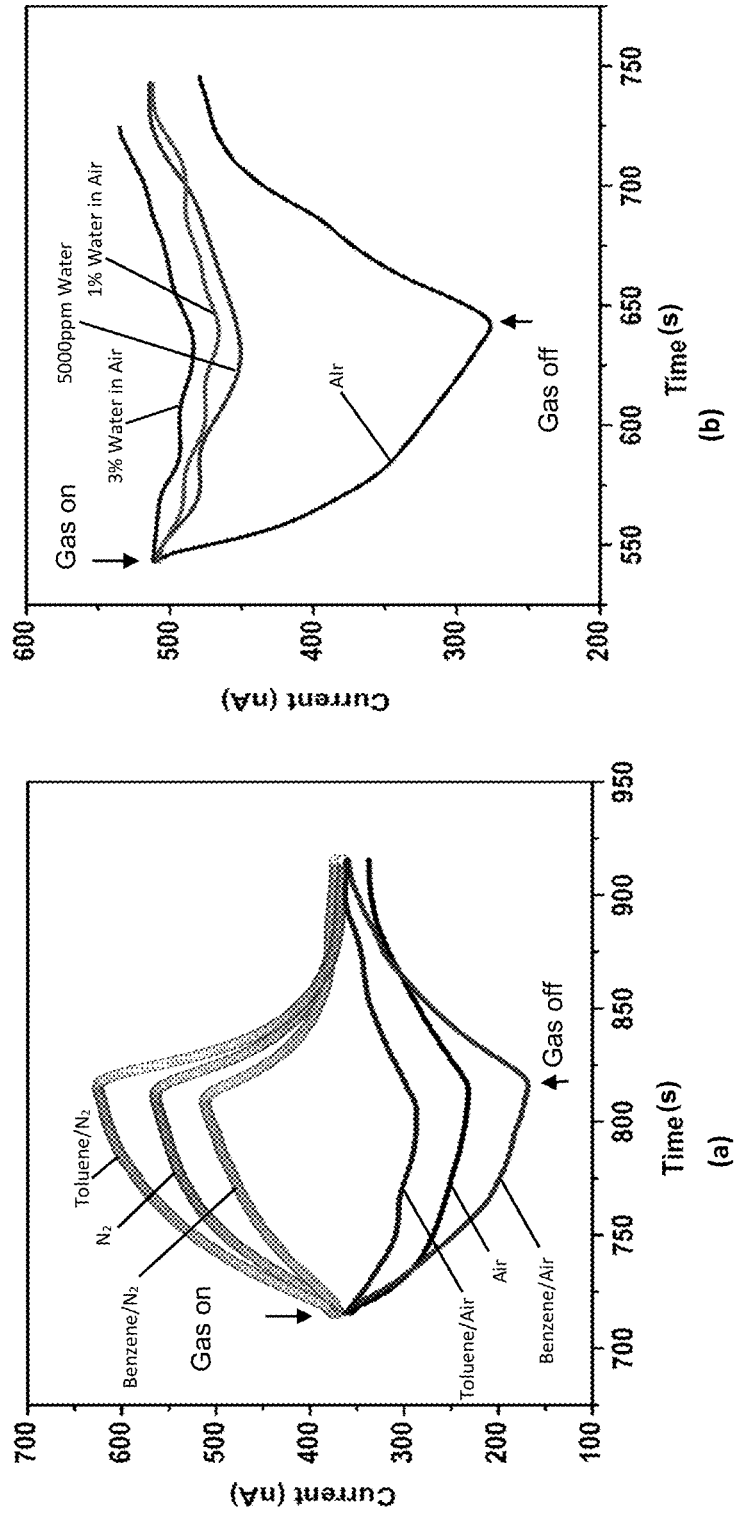
FIG. 2, plate (a), illustrates graphically the photoresponse of a hybrid device (diameter 300 nm) to 1000 ppm of benzene and toluene mixed in air and nitrogen.

The present invention is directed to sensor devices including a semiconductor nanostructure, such as a micro or nanodevice, or nanowire (NW), having a surface functionalized or decorated with metal or metal-oxide nanoparticles or nanoclusters. When metal/metal-oxide nanoparticles selected according to the disclosed methods are placed on the surface of a nanostructure, significant changes result in the physical properties of the system. The nanoparticles increase the adsorption of chemical species by introducing additional adsorption sites, thereby increasing the sensitivity of the resulting system.

The metal or metal-oxide nanoparticles may be selected to act as catalysts designed to lower the activation energy of a specific reaction, which produces active radicals by dissociating the adsorbed species. These radicals can then spillover to a semiconductor structure (see Sermon P A and Bond G C (1973) "*Hydrogen Spillover*," Catal. Rev. 8(2):211-239; Conner W C et al. (1986) "*Spillover of sorbed species*," Adv. Catal. 34:1), where they are more effective in charge carrier transfer. Further, the selected nanoparticles modulate the current through the nanowire through formation of nano-sized depletion regions, which is in turn a function of the adsorption on the nanoparticles. Nanoparticles or nanoclusters suitable for the present invention include virtually any metal-oxide and/or metal. Thus, it should be understood that the present invention is not limited to the particular exemplary metal-oxides and/or metals disclosed in the various embodiments and examples herein.

According to one embodiment, nanowire-nanocluster hybrid chemical sensors were realized by functionalizing n-type (Si doped) gallium nitride (GaN) NWs with $TiO_2$ nanoclusters. The sensors selectively sense benzene and related aromatic environmental pollutants, such as toluene, ethylbenzene, and xylene (sometimes referred to as BTEX). GaN is a wide-bandgap semiconductor (3.4 eV), with unique properties (Morkoç H (1999) *Nitride Semiconductors and Devices*, Springer series in Materials Science, Vol. 32, Springer, Berlin). Its chemical inertness and capability of operating in extreme environments (high-temperatures, presence of radiation, extreme pH levels) is thus suitable for the disclosed sensor design. $TiO_2$ is a photocatalytic semiconductor with a bandgap energy of 3.2 eV (anatase phase). Photocatalytic oxidation of various organic contaminants over titanium dioxide ($TiO_2$) has been previously studied (see Mills A and Hunte S L (1997) "*An overview of semiconductor photocatalysis*," J. Photochem. Photobiol. A 108: 1-35; Luo Y and Ollis D F (1996) "*Heterogeneous photocatalytic oxidation of trichloroethylene and toluene mixtures in air: Kinetic promotion and inhibition, time-dependent catalyst activity*," J. Catal. 163:1-11). The $TiO_2$ nanoclusters were thus selected to act as nanocatalysts to increase the sensitivity, lower the detection time, and enable the selectivity of the structures to be tailored to organic analytes.

The hybrid sensor devices may be developed by fabricating two-terminal devices using individual GaN NWs followed by the deposition of $TiO_2$ nanoclusters using radio frequency (RF) magnetron sputtering. The sensor fabrication process employed standard micro-fabrication techniques. X-ray diffraction (XRD) and high-resolution analytical transmission electron microscopy using energy-dispersive X-ray and electron energy-loss spectroscopies confirmed the presence of anatase phase in $TiO_2$ clusters after post-deposition anneal at 700° C.

A change of current was observed for these hybrid sensors when exposed to the vapors of aromatic compounds (e.g., benzene, toluene, ethylbenzene, xylene, and chlorobenzene mixed with air) under UV excitation, while they had minimal or no response to non-aromatic organic compounds such as methanol, ethanol, isopropanol, chloroform, acetone, and 1,3-hexadiene. The sensitivity range for the noted aromatic compounds, except chlorobenzene, were from about 1% down to about 50 parts per billion (ppb) at room-temperature. By combining the enhanced catalytic properties of the $TiO_2$ nanoclusters with the sensitive transduction capability of the nanowires, an ultra-sensitive and selective chemical sensing architecture is achieved.

As discussed in further detail in Example 1 below, GaN—$TiO_2$ (nanowire-nanocluster) hybrid sensors demonstrated a response to specific volatile organic compounds mixed with air at ambient temperature and humidity. In the presence of UV light (e.g., having a wavelength in the range of about 10 nm to about 400 nm), these hybrid sensor devices exhibited change in the photocurrent when exposed to benzene, toluene, ethylbenzene, xylene, and chlorobenzene mixed in air. However, gases like methanol, ethanol, isopropanol, chloroform, acetone, and 1,3-hexadiene exhibited little or no change in the electrical characteristics of the devices, thus demonstrating the selective response of these sensors to the aromatic compounds. Benzene, toluene, ethylbenzene, and xylene were detected by the disclosed sensors at a concentration level as low as 50 ppb in air. In addition, the disclosed sensor devices are highly stable and able to sense aromatic compounds in air reliably for a wide range of concentrations (e.g., 50 ppb to 1%).

In addition, the disclosed sensors demonstrated highly sensitive and selective detection of traces of nitro-aromatic explosive compounds. As discussed in further detail in Example 5 below, GaN/$TiO_2$ nanowire-nanocluster hybrid sensors detected different aromatic and nitroaromatic compounds at room temperature. For example, the GaN/$TiO_2$ hybrids were able to detect trinitrotoluene (TNT) concentrations as low as 500 pmol/mol (ppt) in air and dinitrobenzene concentrations as low as 10 nmol/mol (ppb) in air in approximately 30 seconds. The noted sensitivity range of the devices for TNT was from 8 ppm down to as low as 500 ppt. The detection limit of dinitrotoluene, nitrobenzene, nitrotoluene, toluene and benzene in air is about 100 ppb with a response time of ≅75 seconds. Devices according to the present invention exhibited sensitive and selective response to TNT when compared to interfering compounds like toluene. Thus, the disclosed sensors are suitable for use as highly sensitive, selective, low-power and smart explosive detectors, which are relatively inexpensive to manufacture in larger quantities.

Based on structural analysis, an exemplary mechanism that qualitatively explains the hybrid sensor's response to different analytes is shown in FIG. 1. With regard to the photocatalytic processes on the $TiO_2$ surface, the oxygen vacancy defects ($Ti^{3+}$ sites) on the surface of $TiO_2$ are the active sites responsible for adsorption of species like oxygen, water, and organic molecules (see Yates Jr J T (2009) "*Photochemistry on $TiO_2$: mechanisms behind the surface chemistry*," Surf. Sci. 603:1605-1612). Interestingly, a relatively defect free $TiO_2$ surface, generated by annealing in high-oxygen flux, is chemically inactive (Li M et al. (1999) "*Oxygen-induced restructuring of rutile $TiO_2$(110): formation mechanism, atomic models, and influence on surface chemistry*," Faraday Discuss. 114:245). Experimental studies and simulations reveal that molecular oxygen is chemisorbed on the surface vacancies ($Ti^{3+}$ sites), acquiring a negative charge as shown in FIG. 1, plate (a) (Anpo M et al. (1999) "*Generation of superoxide ions at oxide surfaces*," Top. Catal. 8:189-198; de Lara-Castells M P and Krause J L (2003) "*Theoretical study of the UV-induced desorption of molecular oxygen from the reduced $TiO_2$ (110) surface*," J. Chem. Phys. 118:5098). This is due to the presence of the localized electron density at or near exposed $Ti^{3+}$ atoms on the $TiO_2$ surface (Henderson M A et al. (1999) "*Interaction of Molecular Oxygen with the Vacuum-Annealed $TiO_2$(110) Surface: Molecular and Dissociative Channels*," J. Phys. Chem. B 103:5328-5337). Water may also be present on the $TiO_2$ cluster surface via molecular or dissociative adsorption, producing $OH^-$ species on the defect sites (Lee F K et al. (2007) "*Role of water adsorption in photoinduced superhydrophilicity on $TiO_2$ thin films*," Appl. Phys. Lett. 90:181928; Bikondoa 0 et al. (2006) "*Direct visualization of defect-mediated dissociation of water on $TiO_2$ (110)*," Nat. Mater. 5:189-192).

Although most of the theoretical and experimental studies on oxygen and water adsorption are done for the (110) surface of rutile phase, there are studies that suggest that similar adsorption behavior is also expected for the anatase surface (Wahab H S et al. (2008) "*Computational investigation of water and oxygen adsorption on the anatase $TiO_2$ (100) surface*," J. Mol. Chem. Struct. 868:101-108). The GaN NW has a surface depletion region as shown in FIG. 1, plate (a), which determines its dark conductivity (Sanford N A et al. (2010) "*Steady-state and transient photoconductivity in c-axis GaN nanowires grown by nitrogen-plasma-assisted molecular beam epitaxy*," J. Appl. Phy. 107:034318).

In the presence of UV excitation with an energy above the bandgap energy of anatase $TiO_2$ (3.2 eV) and GaN (3.4 eV), electron-hole pairs are generated both in the GaN NW and in the $TiO_2$ cluster, as shown in FIG. 1, plate (b). Photogenerated holes in the nanowire tend to diffuse towards the surface due to the surface band bending. This effect of separation of photogenerated charge carriers results in a longer lifetime of photogenerated electrons, which in turn enhances the photoresponse of the nanowire devices. On the $TiO_2$ cluster surface, however, the photogenerated charge carriers lead to a different phenomenon. In n-type semiconductor oxides such as $TiO_2$, the surface adsorption produces upward band-bending, which drives the photogenerated holes towards the surface. The chemisorbed oxygen molecule ($O_2^-$) and hydroxide ions ($OH^-$) can readily capture a hole and desorb as shown in FIG. 1, plate (b) (Perkins C L and Henderson M A (2001) "*Photodesorption and Trapping of Molecular Oxygen at the $TiO_2$(110)—Water Ice Interface*," J. Phys. Chem. B. 105:3856-3863; Thompson T L and Yates J T Jr. (2006) "*Control of a surface photochemical process by fractal electron transport across the surface: O(2) photodesorption from TiO(2)(110),*" J. Phys. Chem. B 110:7431-7435). The decrease of photocurrent through these hybrid sensors when exposed to 20 sscm of air may be due to the increase in oxygen concentration at the surface of $TiO_2$ clusters, leading to an increase in trapping of photogenerated holes at the surface. This process results in increased lifetime of photogenerated electrons. As these nanowires are n-type, excess negative charge on the surface of the wire (on the $TiO_2$ clusters) reduces the nanowire current, thus providing a local-gating effect due to net negative charge accumulation in the $TiO_2$ clusters. Thus, the photoinduced oxygen desorption and subsequent capture of holes by organic adsorbate molecules on the surface of $TiO_2$ clusters produces the local-gating effect, which is responsible for the sensing action of the disclosed sensor devices. The adsorbed hydroxyl ions may also trap a hole forming OH. species. Other effects such as diffusion of carriers between the clusters and the nanowire may also have a role in the sensing properties of the sensors.

Although some embodiments are described in term of excitation in the presence of UV light, it should be understood that excitation by radiation of other wavelengths may be more suitable for devices having other types of metal-oxide and/or metal nanoparticles. For example, excitation in the presence of visible light (i.e., having a wavelength of between about 380 nm and about 740 nm) is suitable for some embodiments.

The process noted above and shown in FIG. 1 also explains sensor response when exposed to $N_2$ flow, as shown in FIG. 2, plate (a). In the presence of 20 sccm of $N_2$ flow, the photocurrent in the sensors increases significantly in comparison with 20 sccm of air flow. In an $N_2$ environment, oxygen is desorbed from the surface vacancy sites by capturing photogenerated holes, but does not get re-adsorbed, resulting in significant reduction of hole capture. As such, the photogenerated electron-hole pairs recombine effectively in the cluster. Thus, the photocurrent through the nanowire/nanocluster hybrid sensor, which is otherwise increased due to the local-gating effect by the $TiO_2$ clusters, is absent in an $N_2$ environment.

In the presence of water in air, the photocurrent through these sensors recovers towards the level without air flow, as seen in FIG. 2, plate (b), indicating a reduction of the hole trapping due to adsorption of water on the $TiO_2$ surface. Water may be adsorbed as a molecule on the defect sites replacing $O_2$ (see Herman G S et al. (2003) "*Experimental Investigation of the Interaction of Water and Methanol with Anatase-$TiO_2$(101),*" J. Phys. Chem. B 107:2788-2795). With increasing water concentration, more defects are filled with water. If the adsorbed water dissociates and produces $OH^-$ species, then it is possible that it will act as hole traps and decrease the photocurrent the same way the photodesorption of oxygen does. A competition between the molecular water adsorption (reducing hole capture) and dissociative water adsorption (increasing hole capture) is possible, with the dominant process ultimately determining the photocurrent level in the nanowires in the presence of water.

The presence of aromatic compounds such as benzene, ethylbenzene, chlorobenzene, and xylene in air reduced the photocurrent (e.g. see FIG. 2, plate (a)). Organic molecules are known hole-trapping adsorbates (see Yamakata A et al. (2002) "*Electron-and hole-capture reactions on Pt/$TiO_2$ photocatalyst exposed to methanol vapor studied with time-resolved infrared absorption spectroscopy*," J. Phys. Chem. B 106:9122-9125). Most aromatic compounds show high affinity for electrophilic aromatic substitution. The exact mechanism of photooxidation of adsorbed organic compounds on $TiO_2$ is complex. However, it is believed that oxidation occurs by either indirect oxidation via the surface-bound hydroxyl radical (i.e., a trapped hole at the $TiO_2$ surface) or directly via the valence-band hole before it is trapped either within the particle or at the particle surface (see Nosaka Y et al. (1998) "*Factors governing the initial process of $TiO_2$ photocatalysis studied by means of in situ electron spin resonance measurements*," J. Phys. Chem. B 102:10279-10283; Mao Y et al. (1991) "*Identification of organic acids and other intermediates in oxidative degradation of chlorinated ethanes on titania surfaces en route to mineralization: a combined photocatalytic and radiation chemical study*," J. Phys. Chem. 95:10080-10089). In the presence of air (with residual water) hydroxyl mediated hole transfer to adsorbates such as benzene, xylene is dominant, whereas in the $N_2$ environment direct transfer of valence band holes to aromatic adsorbates could be possible.

Irrespective of the hole transfer mechanism, the presence of additional hole traps reduces the sensor photocurrent, as observed in the presence of benzene mixed with $N_2$ and air as shown in FIG. 2, plate (a). The model disclosed herein qualitatively explains the observed trends for compounds tested, such as benzene, ethylbenzene, chlorobenzene, and xylene. However, toluene exhibits a different trend, which may be due to other second order effects other than or in addition to the hole trapping mechanism.

The disclosed mechanism is further validated when comparing ionization energies of various compounds tested with the responses generated when the sensors are exposed to them (see Table I). The effectiveness of the process of hole transfer to the adsorbed organic molecules relates to the compound's ability to donate an electron (i.e. the lower the ionization energy of a compound, the easier for it to donate an electron or capture a hole). The observed sensitivity trend for benzene (lowest sensitivity), ethylbenzene, and xylene (highest sensitivity) correlates with their ionization energies as shown in Table I, with benzene being the highest and xylene the lowest among the three.

TABLE I

Physical Properties of Various Compounds Tested

| Organic Compound | Sensitivity | Ionization Potential (eV) |
| --- | --- | --- |
| Chloroform | No | 11.37 |
| Ethanol | No | 10.62 |

TABLE I-continued

Physical Properties of Various Compounds Tested

| Organic Compound | Sensitivity | Ionization Potential (eV) |
| --- | --- | --- |
| Isopropanol | No | 10.16 |
| Cyclohexane | Yes | 9.98 |
| Acetone | No | 9.69 |
| Benzene | Yes (Min) | 9.25 |
| Chlorobenzene | Yes | 9.07 |
| Toluene | Yes | 8.82 |
| Ethylbenzene | Yes | 8.77 |
| Xylene | Yes (Max) | 8.52 |
| 1,3-Hexadiene | No | 8.50 |

As shown in Table I, the sensitivity trend is consistent for aromatics, given 1,3-Hexadiene produced no response in the sensors. Although most functional groups with either a non-bonded lone pair or p-conjugation show oxidative reactivity towards $TiO_2$ (Hoffman M R et al. (1995) "*Environmental Applications of Semiconductor Photocatalysis*," Chem. Rev. 95:69-96), aromatic compounds are more easily photocatalyzed than aliphatic ones under the same conditions (Carp 0 et al. (2004) "*Photoinduced reactivity of titanium dioxide*," Prog. Solid St. Chem. 32:33-177).

Thus, the metal-oxide nanoclusters ($TiO_2$) on GaN NWs or nanostructures demonstrate the disclosed architecture for highly selective gas sensing. The exemplary sensors are capable of selectively sensing benzene and related aromatic compounds at nmol/mol (ppb) level in air at room-temperature under UV excitation.

According to another embodiment, the specific selectivity of the disclosed nanowire (or nanostructure)/nanocluster hybrid sensors may be tailored using a multi-component nanocluster design. For example, catalytic metals (e.g., platinum (Pt), palladium (Pd), and/or any other transition metals) are deposited onto the surface of oxide photocatalysts in order to enhance their catalytic activity. Metal clusters on a metal-oxide catalyst alter the behavior of the metal-oxide catalyst by any one, or a combination of, the following mechanisms: 1) changing the surface adsorption behavior as metals often have very different heat of adsorption values compared to the metal-oxides; 2) enabling catalytic decomposition of certain analytes on the metal surface, which otherwise would not be possible on the oxide surface; 3) transporting active species to the metal-oxide support by the spill-over effect from the metal cluster; 4) generating a higher degree of interface states, thus increasing reactive surface area reaction area; 5) changing the local electron properties of the metal clusters, such as workfunction, due to adsorption of gases; and 6) effectively separating photogenerated carriers in the underlying metal-oxide. The effect of transition metal loading such as iron (Fe), copper (Cu), Pt, Pd, and rhodium (Rh) onto $TiO_2$ has been evaluated for photocatalytic decomposition of various chemicals in both gas-solid and liquid-solid regimes.

In one implementation, the selectivity of the titanium dioxide ($TiO_2$) nanocluster-coated gallium nitride (GaN) nanostructure sensor device is altered by addition of platinum (Pt) nanoclusters. In another implementation, the sensor device includes Pt nanocluster-coated GaN nanostructure. The hybrid sensor devices may be developed by fabricating two-terminal devices using individual GaN NWs or nanostructures followed by the deposition of $TiO_2$ and/or Pt nanoclusters (NCs) using a sputtering technique, as described above.

The sensing characteristics of GaN/($TiO_2$—Pt) nanowire-nanocluster (NWNC) hybrids and GaN/(Pt) NWNC hybrids is altered as compared to GaN/$TiO_2$ sensors. The GaN/$TiO_2$ NWNC hybrids show remarkable selectivity to benzene and related aromatic compounds with no measurable response for other analytes, as discussed above. However, the addition of Pt NCs to GaN/$TiO_2$ sensors dramatically alters the sensing behavior, making them sensitive only to methanol, ethanol, and hydrogen, but not to other chemicals tested, as discussed in further detail in Example 2 below.

The GaN/($TiO_2$—Pt) hybrid sensors were able to detect ethanol and methanol concentrations of 100 nmol/mol (ppb) in air in approximately 100 seconds, and hydrogen concentrations from 1 µmol/mol (ppm) to 1% in nitrogen in less than 60 seconds. However, GaN/Pt hybrid sensors showed limited sensitivity only towards hydrogen and not towards any alcohols. All the hybrid sensors are operable at room temperature and are photomodulated (i.e., responding to analytes only in the presence of light, e.g., ultra violet (UV) light). The selectivity achieved is significant from the standpoint of numerous applications requiring room-temperature sensing, such as hydrogen sensing and sensitive alcohol monitoring. For example, the dynamic response of an exemplary $TiO_2$ based sensor exposed to methanol at room temperature and at a concentration of 500 ppm is illustrated in FIG. 5I, plate (a). The disclosed sensors therefore demonstrate tremendous potential for tailoring the selectivity of the hybrid nanosensors for a multitude of environmental and industrial sensing applications.

A qualitative understanding of the selective sensing mechanism of the disclosed sensors may be developed by considering how different molecules adsorb on the nanocluster surfaces, and determining the roles of intermediate reactions in the sensitivity of the sensors. While some of the embodiments, examples and explanation describe the invention in terms of NWs, it should be understood that other nanostructures or microstructures may be utilized. Accordingly, the present invention is not limited to sensors including NWs.

The Photocurrent in GaN/($TiO_2$—Pt) Hybrid Sensors in the Presence of Air, Nitrogen, and Water:

The oxygen vacancy defects ($Ti^{3+}$ sites) on the surface of $TiO_2$ are the "active sites" for the adsorption of species like oxygen, water, and organic molecules (Yates Jr J T (2009) "*Photochemistry on $TiO_2$: mechanisms behind the surface chemistry*," Surf. Sci. 603:1605-1612; Bikondoa 0 et al. (2006) "*Direct visualization of defect-mediated dissociation of water on $TiO_2$(110)*," Nat. Mater. 5:189-192). It has been observed that oxygen adsorption on photocatalyst powders such as $TiO_2$ and ZnO quenches the photoluminescence (PL) intensity, while adsorption of water produces an enhancement of the PL. Electron-trapping adsorbates, such as oxygen, increase the band-bending of $TiO_2$, which facilitates the separation of photogenerated electron hole pairs in the oxide. Subsequently, the PL intensity is decreased as the photogenerated charge carries cannot recombine efficiently. Conversely, in the case of water, the band bending is reduced, resulting in an increase in the PL intensity. In explaining the observed behavior of the hybrid sensors, the depletion effect induced by the $TiO_2$ clusters on GaN NW is considered. Considering an inverse relationship, i.e., increase in depletion of the $TiO_2$ cluster leads to a decrease in the depletion width in the GaN NW and vice versa, some of the observed sensing behavior is explained.

Figure 3:
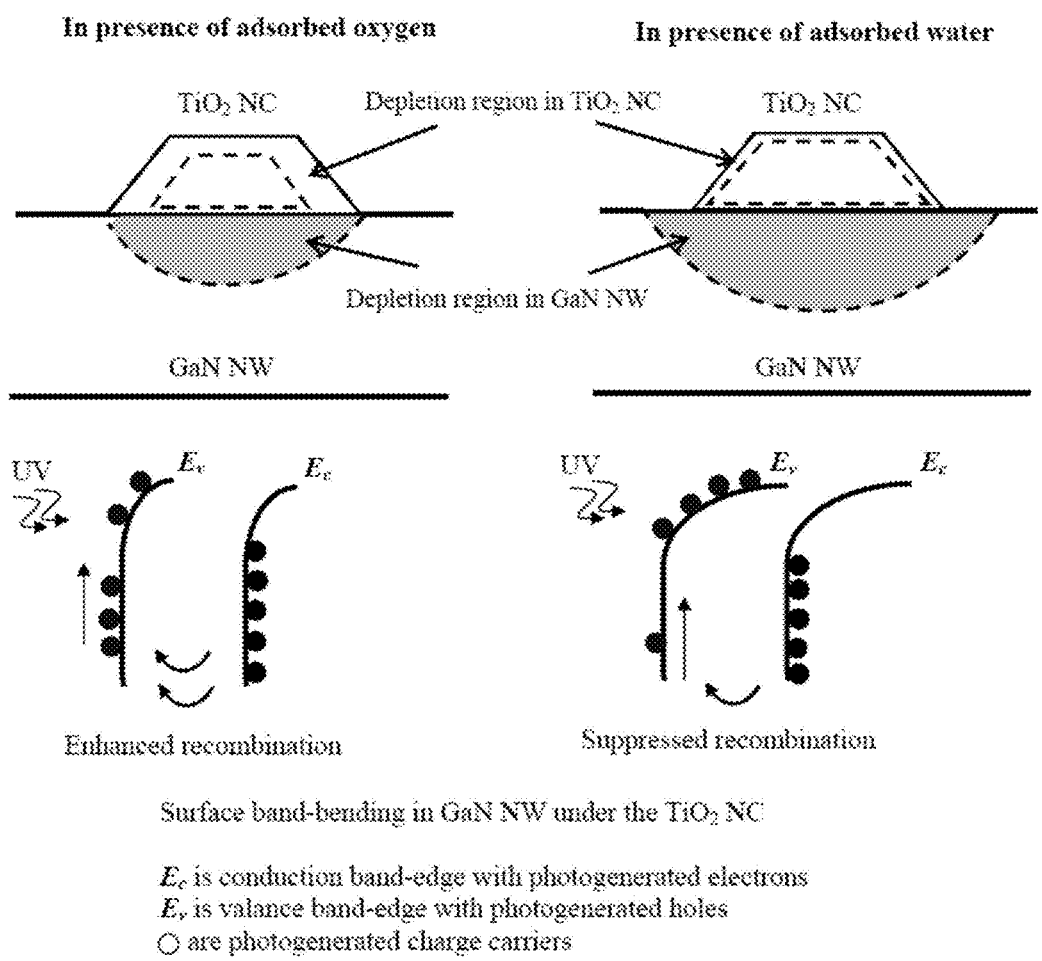
FIG. 3 is a schematic representation of depletion in the $TiO_2$ NC in the presence of oxygen and water, and its effect on the photogenerated charge carrier separation in GaN NW. Circles in valence band indicate holes and circles in conduction band indicate electrons.

As shown in FIG. 3, when oxygen is adsorbed on the $TiO_2$ NC surface, the depletion width in the NC increases, leading to a decrease in the depletion width in the NW. Adsorption of water, nitrogen, and alcohol produce the reverse effect: they decrease the depletion width of the $TiO_2$ NC, leading to an increase in the band-bending on the GaN NW. Increased band-bending in the GaN NW results in an effective separation of charge carriers, leading to an increase in photocurrent through the NW. This qualitatively explains the increase in the photocurrent when the hybrid sensor is exposed to water mixed with air or with pure nitrogen (see FIG. 4). However, the increase in the photocurrent when exposed to 20 sccm of air flow is not fully explained. Under air flow, more oxygen should adsorb on the NCs, causing an increase in the depletion width of the cluster. This should have resulted in a decrease in the photocurrent based on our assumption; however, an increase in the photocurrent is exhibited (FIG. 4) when 20 sccm of air is passed through the chamber.

In the absence of UV light, the absorption or desorption of chemicals from the cluster surfaces cannot modulate the dark current through the nanowire. In the dark, the surface depletion layer of the GaN NW is thicker compared to under UV excitation (see Mansfield L M et al. (2009) "*GaN nanowire carrier concentration calculated from light and dark resistance measurements*," Journal of Electronic Materials 38:495-504). The minority carrier (hole) concentration is also significantly lower. Thus the NCs are ineffective in modulating the dark current through the NW.

Mechanism of Sensing of Alcohols and Hydrogen by GaN/(TiO$_2$—Pt) NWNC Sensors

Adsorption of alcohols (RCH$_2$—OH) on the TiO$_2$ surface leads to their oxidation (Kim K S and Barteau M A (1989) "*Reaction of Methanol on TiO$_2$*," Surface Science 223:13-32). Although there are various mechanisms of oxidation of adsorbed alcohols on TiO$_2$ surface, focus is on the oxidation of alcohols by photogenerated holes. The process is described by the following reactions:

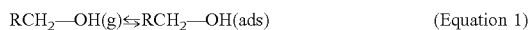

$$RCH_2\text{—}OH(g) \leftrightarrows RCH_2\text{—}OH(ads) \quad \text{(Equation 1)}$$

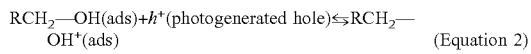

$$RCH_2\text{—}OH(ads) + h^+(\text{photogenerated hole}) \leftrightarrows RCH_2\text{—}OH^+(ads) \quad \text{(Equation 2)}$$

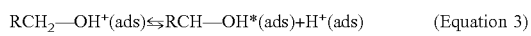

$$RCH_2\text{—}OH^+(ads) \leftrightarrows RCH\text{—}OH^*(ads) + H^+(ads) \quad \text{(Equation 3)}$$

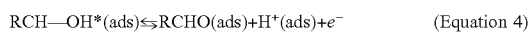

$$RCH\text{—}OH^*(ads) \leftrightarrows RCHO(ads) + H^+(ads) + e^- \quad \text{(Equation 4)}$$

where (ads) and (g) represent adsorbed and gas phase species, respectively. For Equation 4 to proceed in the forward directions, the H$^+$ species should be removed effectively. It is possible that from TiO$_2$ NCs the H$^+$ species can spill-over on to Pt clusters nearby, where they can be reduced to form H$_2$:

$$2H^{+(ads)} + 2e^- \leftrightarrows H_2(g) \quad \text{(Equation 5)}$$

Figure 4:
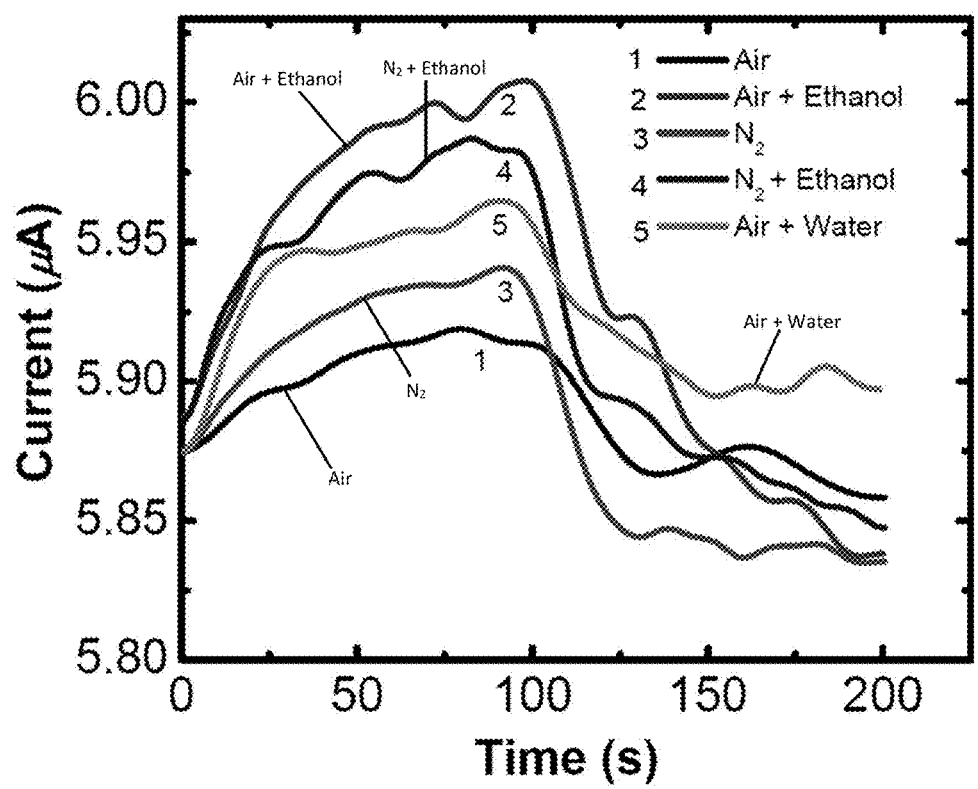
FIG. 4 illustrates graphically the photo-response of the GaN/($TiO_2$—Pt) device to 1000 μmol/mol of ethanol in air and nitrogen, and to 1000 μmol/mol of water in air. The devices did not respond to water in nitrogen. The air-gas mixture was turned on at 0 s and turned off at 100 s.

As H$^+$ reduction and hydrogen-hydrogen recombination is weak on the bare TiO$_2$ surface (Fujishima A et al. (2008) "*TiO$_2$ photocatalysis and related surface phenomena*," Surf. Sci. Rep. 63:515-582), the rate of alcohol oxidation to aldehyde might be affected by the H$^+$ reduction and hydrogen-hydrogen recombination on the Pt NCs. Adsorption of alcohols and their subsequent oxidation due to trapping of photogenerated holes leads to a decrease in the band bending of TiO$_2$ NCs. As shown in FIG. 3, this leads to an increase in the NW photocurrent, which is observed for the GaN/(TiO$_2$—Pt) sensors when exposed to methanol and ethanol (FIG. 4). It is likely that the production of H.sub.2 on Pt is the key for sensing alcohols by GaN/(TiO$_2$—Pt) sensors. Additionally, H$_2$ on Pt surface can dissociate and diffuse to the Pt/TiO$_2$ interface. Atomic hydrogen is shown to produce an interface dipole layer, which reduces the effective workfunction of Pt (Du X et al. (2002) "*A New Highly Selective H$_2$ Sensor Based on TiO$_2$/PtO-Pt Dual-Layer Films*," Chem. Mater. 14:3953-3957). Effective reduction of Pt workfunction also reduces the depletion width in TiO$_2$, which according to the model in FIG. 4, also leads to an increase in the photocurrent when these sensors are exposed to alcohols. In the presence of hydrogen in nitrogen, the workfunction change of Pt NCs due to hydrogen adsorption is the likely cause for the sensing behavior of these sensor hybrids.

Selectivity of GaN/(TiO$_2$—Pt), GaN/Pt, and GaN/TiO$_2$NWNC Hybrid Sensors

A significant finding of the present invention is the change in the selectivity of GaN/TiO$_2$ hybrid sensors due to the addition of Pt NCs. The observed selectivity behavior of the three hybrids can be qualitatively explained if the heat of adsorption of the analytes on TiO$_2$ and Pt surfaces is considered as shown in Table II and their ionization energies presented in Table III.

TABLE II

Heat of Adsorption for Methanol, Benzene, and Hydrogen on Pt and TiO$_2$ (Anatase*)

| Surface | Hydrogen (kJ/mol) | Methanol (kJ/mol) | Benzene (kJ/mol) |
|---|---|---|---|
| TiO$_2$ | Negligible | 92 | 64 |
| Pt | 100 | 48 | 117 |

*The heat of absorption values for TiO2 rutile surfaces are comparable

TABLE III

Ionization Energy of the Analytes (CRC Handbook of Chemistry and Physics, 84th ed.; CRC Press: Boca Raton, FL., 2003):

| Organic Compound | Ionization Energy (eV) |
|---|---|
| Methanol | 10.85 |
| Hydrogen | 13.5 |
| Benzene | 9.25 |

Referring to Table II, benzene has a higher heat of adsorption on Pt than on TiO$_2$. Therefore, benzene will preferentially adsorb on Pt in the TiO$_2$—Pt cluster. Now, in the absence of Pt, when the benzene is adsorbed on TiO$_2$ it can interact with the photogenerated charge carriers resulting in the sensing behavior of GaN/TiO$_2$ devices. However, if benzene is adsorbed on Pt (such as in the case of TiO$_2$—Pt and Pt nanoclusters on GaN) then benzene molecules cannot interact with photogenerated charge carriers in TiO$_2$, and therefore are ineffective in producing any current modulation in the nanowire. Thus, benzene is detected by GaN/TiO$_2$ sensor devices, but not by GaN/(TiO$_2$—Pt) and GaN/Pt sensor devices.

Further, methanol is detected by GaN/(TiO$_2$—Pt) sensors only, and not by GaN/TiO$_2$ and GaN/Pt sensors. From Table III, methanol (unlike benzene) effectively adsorbs on TiO$_2$, whether Pt is present or absent (as the heat of adsorption of methanol is higher on TiO$_2$ than Pt). It is believed that methanol on TiO$_2$ in the absence of Pt does not participate in photogenerated carrier trapping as efficiently as benzene and other aromatic compounds on the TiO$_2$ nanoclusters. Referring to Table III, the ionization energy of methanol, hydrogen, and benzene is shown. The effectiveness of the process of hole transfer to the adsorbed organic molecules is related to the compound's ability to donate an electron (i.e. the lower the ionization energy of a compound, the easier for it to donate an electron or capture a hole). However, in the presence of Pt nanoclusters nearby, methanol adsorption on TiO$_2$ ultimately leads to formation of H$^+$ through photooxidation of methanol, and eventually $H_2$, which is the key molecule for sensing of methanol by ($TiO_2$—Pt) NCs on GaN NW. A similar mechanism applies for ethanol sensing by the GaN/($TiO_2$—Pt) hybrids.

Hydrogen is detected by GaN/($TiO_2$—Pt) and GaN/Pt hybrids, and not by GaN/$TiO_2$ NWNC sensors, and GaN/($TiO_2$—Pt) sensors have a higher response to hydrogen than to alcohols. From Table II, hydrogen has negligible heat of adsorption on $TiO_2$, thus GaN/$TiO_2$ devices are not sensitive to hydrogen. However, in the presence of Pt NCs on $TiO_2$, hydrogen can adsorb on the Pt NCs. Once adsorbed, hydrogen can modify the workfunction of Pt, resulting in a change in the photocurrent through the nanowire. However, this is not the only mechanism, as that would imply that GaN/Pt hybrids should be equally sensitive to $H_2$. It is believed that when hydrogen is adsorbed on the $TiO_2$—Pt NC, it also reduces the $TiO_2$ surface. Thus, in the presence of only Pt on GaN, workfunction modification of Pt solely produces change in the photocurrent in the NW. However, in the presence of Pt and $TiO_2$ NCs, hydrogen adsorption leads to the modulation of the photocurrent in GaN NW, through modulation of Pt workfunction together with the change in the depletion layer of the $TiO_2$ NCs, resulting in a larger change of the photocurrent, thus higher sensitivity.

Figure 5:
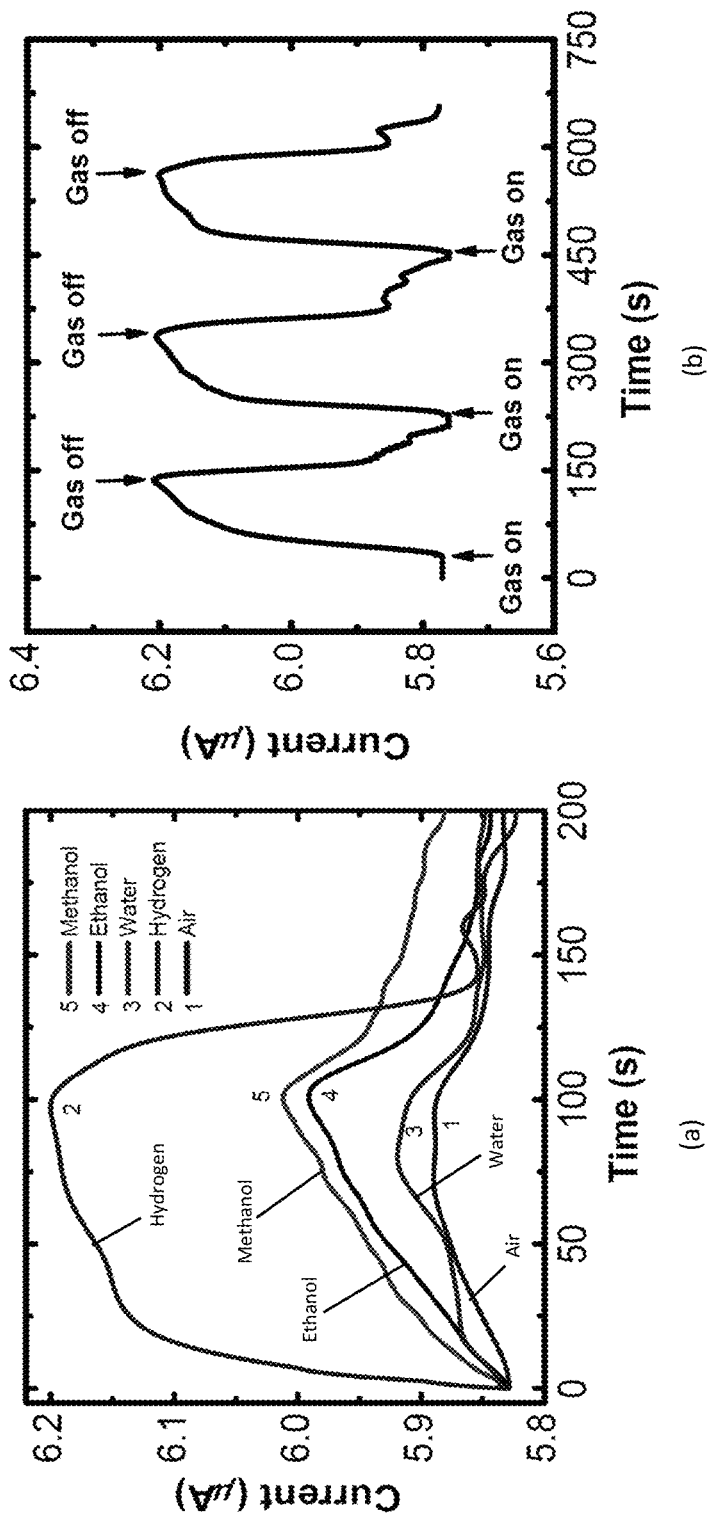
FIG. 5, plate (a) illustrates graphically UV photo-response of the GaN/($TiO_2$—Pt) hybrid device to 1000 μmol/mol (ppm) of methanol, ethanol, and water in air, and hydrogen in nitrogen. The air-gas mixture was turned on at 0 s and turned off at 100 s.

The faster and larger response of GaN/($TiO_2$—Pt) towards $H_2$ compared to the alcohols (as shown in FIG. 5) is due to the fact that in the case of alcohols, hydrogen is produced after photo-oxidation of the adsorbed alcohols, which is a two-step process with lower yield. In the case of $H_2$ in nitrogen, there is a direct availability of $H_2$ molecules.

GaN/($TiO_2$—Pt) sensors are not sensitive to high carbon-containing (C>2) alcohols such as propanol and butanol. In this regard, it has been shown that the hydrogen production from the photocatalytic oxidation of alcohols on $TiO_2$/Pt surface is related to the polarity of the alcohols (i.e., the higher the polarity of the alcohol the greater the yield of photocatalytic hydrogen production) (see Yang Y Z et al. (2006) "*Photo-Catalytic Production of Hydrogen Form Ethanol over M/TiO$_2$ Catalysts (M=Pd, Pt or Rh)*," Applied Catalysis B: Environmental 67:217-222). The polarity (Y) is defined as $Y=(\varepsilon_s-1)/(\varepsilon s+2)$, where $\varepsilon_s$ is the relative permittivity of the solvent. Table IV lists the polarity of various alcohols tested.

TABLE IV

Solvent Polarity of Various Alcohols

| Solvent | Polarity |
|---|---|
| Methanol | 0.91 |
| Ethanol | 0.89 |
| n-Propanol | 0.86 |
| i-Propanol | 0.85 |
| Butanol | 0.84 |

The relative difficulty of producing hydrogen from higher carbon-containing alcohols (C>2) is believed to be the cause of the GaN/($TiO_2$—Pt) sensor's inability to detect alcohols with C greater than 2. The sensor's greater response to methanol than ethanol (at least for concentrations above 500 μmol/mol) is also consistent with the polarities of the alcohols.

Figure 52:
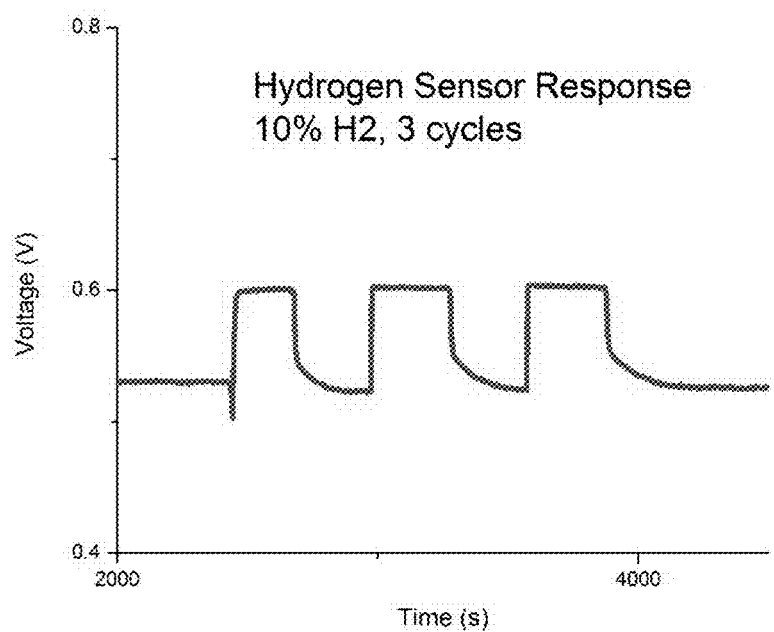
FIG. 52 illustrates graphically the dynamic responses of a ZnO—Pd—Ag based sensor exposed to H$_2$ at room temperature.

The GaN/($TiO_2$—Pt) hybrid sensors are operable at room-temperature sensing of hydrogen, and thus are suitable for various applications (e.g., industrial production facilities, oil refineries, hydrogen monitoring in hydrogen-powered vehicles, alcohol monitoring systems for industrial and law-enforcement purposes, etc.). The disclosed mechanisms and methods may be implemented for achieving other multicomponent NWNC based sensors. For example, the dynamic response of a ZnO—Pd—Ag based sensor exposed to $H_2$ at room temperature is illustrated in FIG. 52. Through combinations of metal and metal-oxides available, a library of sensors may be produced, each with precisely tuned selectivity, on a single chip for detecting a wide variety of analytes in many different environments.

Figure 51:
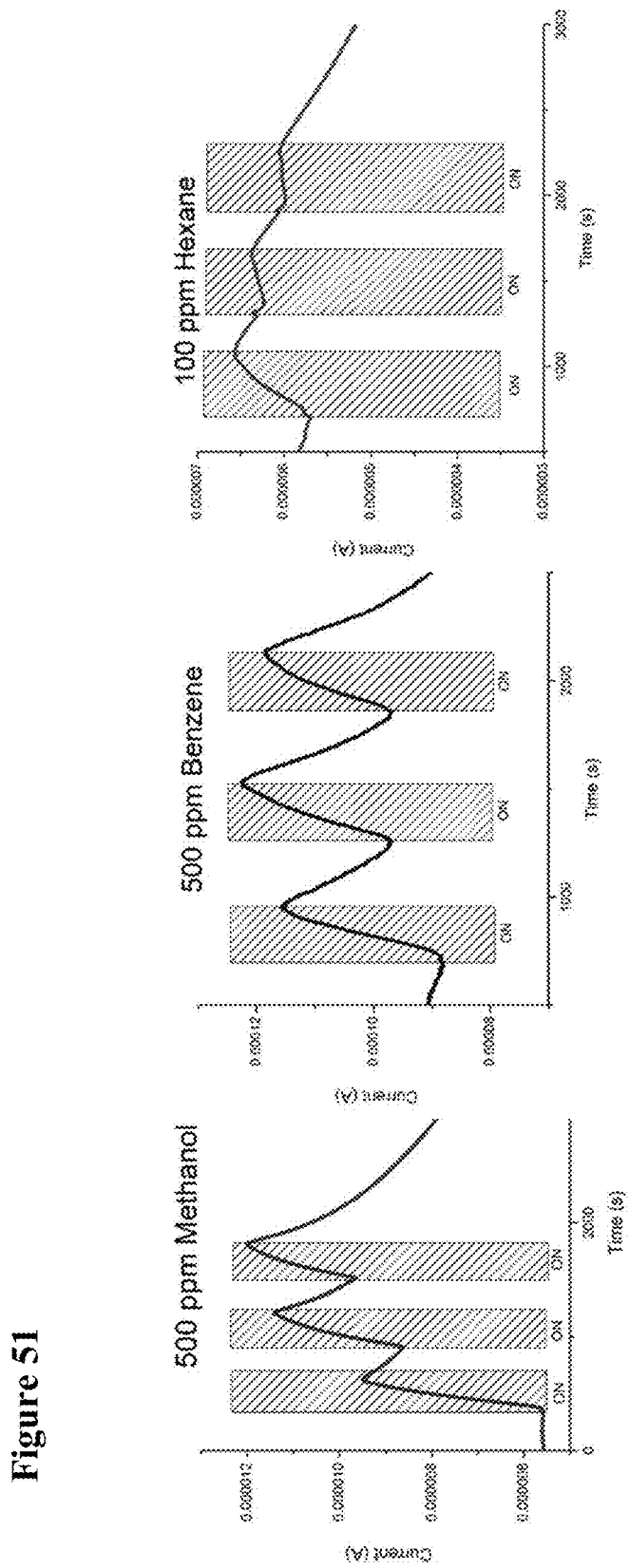
FIG. 51, plate (a) illustrates the dynamic response of a TiO$_2$ based sensor exposed to methanol at room temperature and at a concentration of 500 ppm. Plate (b) illustrates the dynamic response of a ZnO based sensor exposed to benzene at room temperature and a concentration of 500 ppm. Plate (c) illustrates the dynamic response of the ZnO based sensor exposed to hexane at room temperature and a concentration of 100 ppm.

Thus, an inactive semiconductor nanostructure (e.g., NW) surface may be functionalized with selected analyte-specific active metal-oxide nanoparticles. For example, another embodiment of the present invention provides for alcohol sensors using gallium nitride (GaN) nanowires (NWs) functionalized with zinc oxide (ZnO) nanoparticles. The dynamic response of exemplary ZnO based sensors exposed to benzene (concentration 500 ppm) and hexane (concentration 100 ppm) at room temperature is shown in FIG. 51, plates (b) and (c). The disclosed sensors operate at room temperature, are fully recoverable, and demonstrate a response and recovery time on the order of 100 seconds or less. The sensing is assisted by ultraviolet (UV) light within the 215-400 nm band and with the intensity of 375 nW/cm$^2$ measured at 365 nm.

Figure 6:
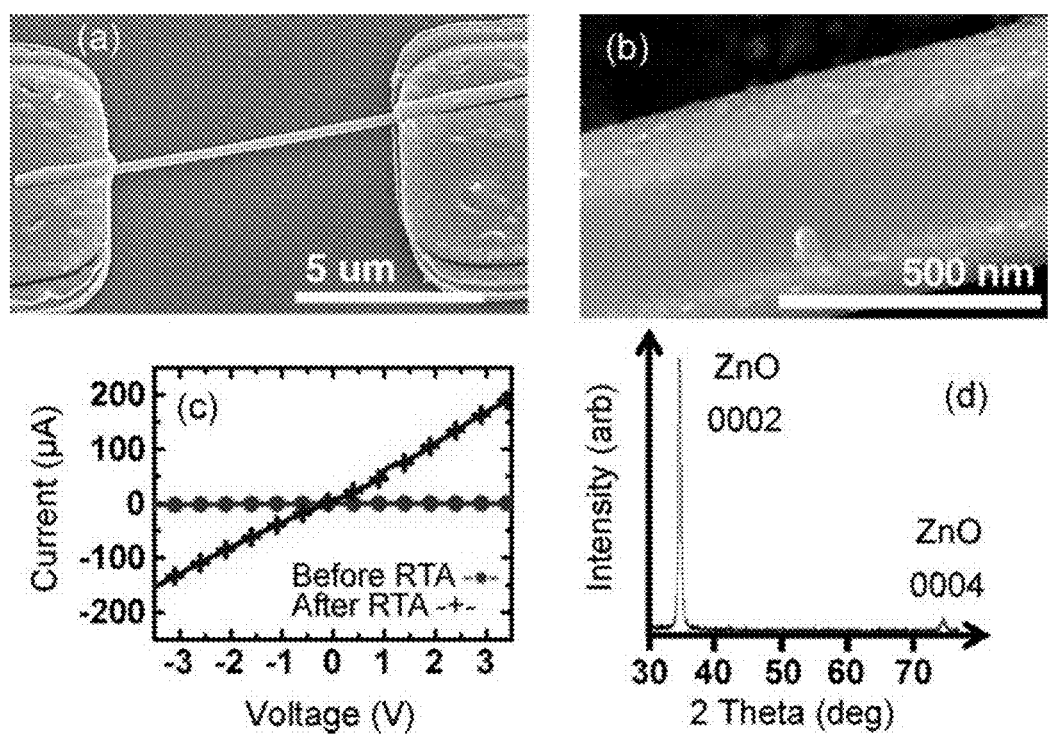
FIG. 6, plate (a) is a scanning electron microscope (SEM) image of the NW bridge structure according to the present invention.

As discussed above, the conductivity model of GaN nanostructure is comprised of a conducting channel surrounded by a surface depletion region, where modulation in the width of the depletion region induces a change in the conductivity of the NW. Similarly, ZnO nanoparticles have a surface depletion layer, which enhances upon exposure to air due to electron capture by surface-adsorbed oxygen. When UV light is turned on, the photogenerated holes in ZnO assist in removing the adsorbed oxygen, thus releasing the electrons captured by surface oxygen back into ZnO. The photoinduced excess of electrons in the ZnO nanoparticles promotes photogenerated charge separation in the GaN nanostructure, thereby resulting in increased conductivity. Conversely, there is a reduction in the number of free electrons in the ZnO nanoparticles when exposed to air, leading to a reduced conductivity. As seen in FIG. 6, this effect increases with increasing flow rate of air due to enhanced coverage of the device surface with adsorbed oxygen.

The device response to alcohols may be explained by the following generic reaction occurring on the surface of ZnO:

$$2CH_3OH+O^-_2(adsorbed) \rightarrow 2HCHO+2H_2O+e^- \quad \text{(Equation 6)}$$

Figure 7:
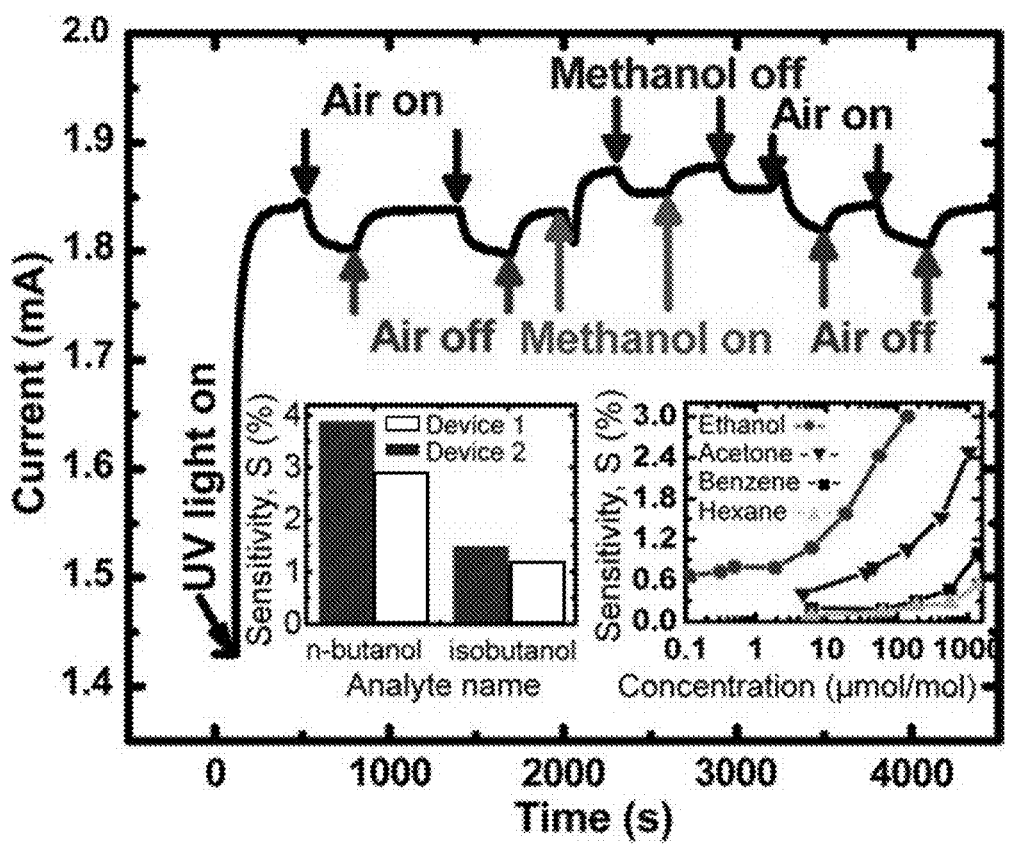
FIG. 7 illustrates graphically device response to 500-μmol/mol (ppm) of methanol. The inset graph at the bottom left shows the sensitivity of two devices toward 500 μmol/mol (ppm) of each isomer of butanol (with Device 1 shown as the right bar above each isomer, and Device 2 shown as the left bar above each isomer). The inset graph at the bottom right shows the response to ethanol, acetone, benzene, and hexane. Sensitivity (S) is given by $(I_g - I_a) \times 100/I_a$, where $I_g$ is the device current in the presence of an analyte in breathing air and $I_a$ is the current in pure breathing air, both measured 300 s after the flow is turned on. Percentage standard deviation of the device sensitivity is 3.2% based on the five data points collected over a period of 3 days in response to the breathing air.
Figure 8:
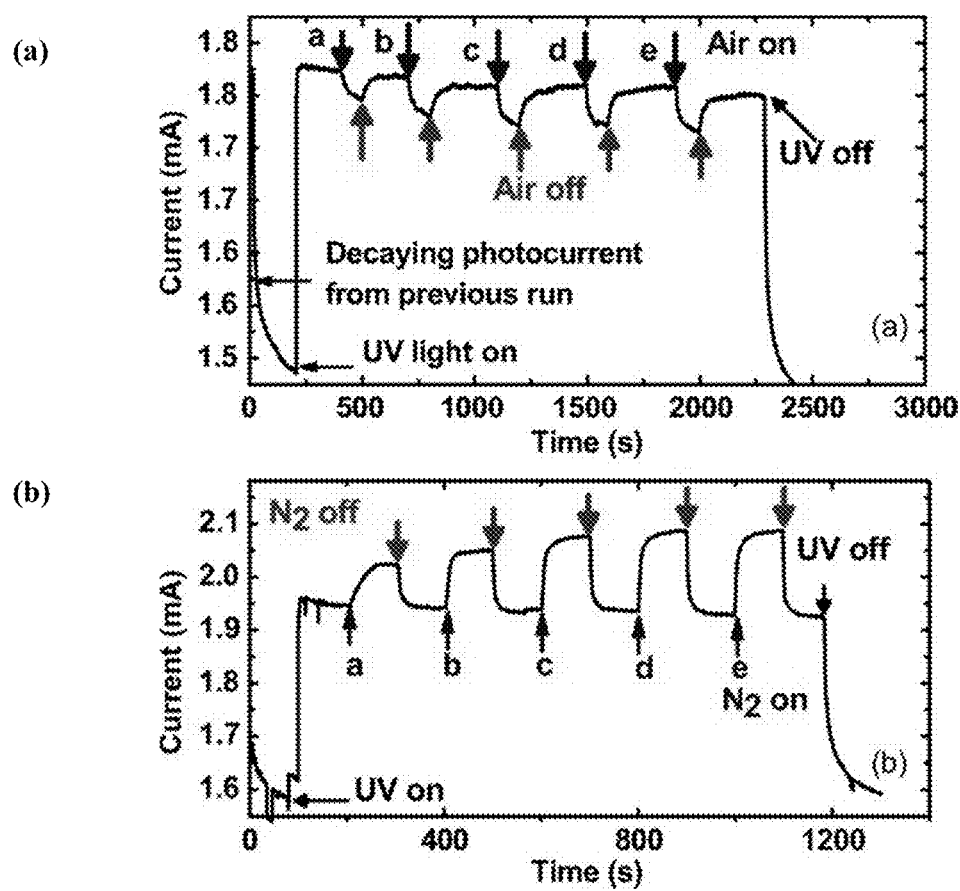
FIG. 8 illustrates graphically device response to different flow rates of breathing air (plate (a)) and nitrogen gas (plate (b)). The flow rates of the gas are denoted as a=20 sccm, b=40 sccm, c=60 sccm, d=80 sccm, and e=100 sccm.

As shown in FIG. 7, the exposure to alcohol vapors leads to increased device conductivity due to the removal of adsorbed oxygen. In the case of exposure to $N_2$, although there is no surface reaction, $N_2$ assists in desorption of the oxygen, thus restoring the conductivity, as shown in FIG. 8.

The disclosed hybrid GaN nanostructure/ZnO nanoparticle devices are suitable for UV-assisted alcohol sensing at room temperature. These devices are a suitable candidate for making nanosensor arrays because of their tunable selectivity, ability to detect the pbb level of analytes, and fast response and recovery time.

The disclosed hybrid chemiresistive architectures utilizing nanoengineered wide-bandgap semiconductor backbone functionalized with multicomponent photocatalytic nanoclusters of metal-oxides and/or metals are particularly suitable for larger scale manufacturing techniques, such as for commercial applications. The sensors operate at room-temperature via photoenabled sensing. A substantial benefit of the disclosed sensors is the utilization of all standard microfabrication techniques, thus resulting in economical, multianalyte single-chip sensor solution. By combining the "designer" adsorption properties of multicomponent nanoclusters together with sensitive transduction capability of nanostructured semiconductor backbones, photoenabled, room temperature, ultra-sensitive, and highly selective chemical sensors are achieved.

The sub-micron structures may be formed on an epitaxial thin-film grown on non-conductive/semi-insulating substrate using deep UV lithography and a combination of plasma etching and wet-etching. Such structures are functionalized with multicomponent nanoclusters of metal-oxides and metals using reactive-sputter deposition, as noted above.

Figure 9:
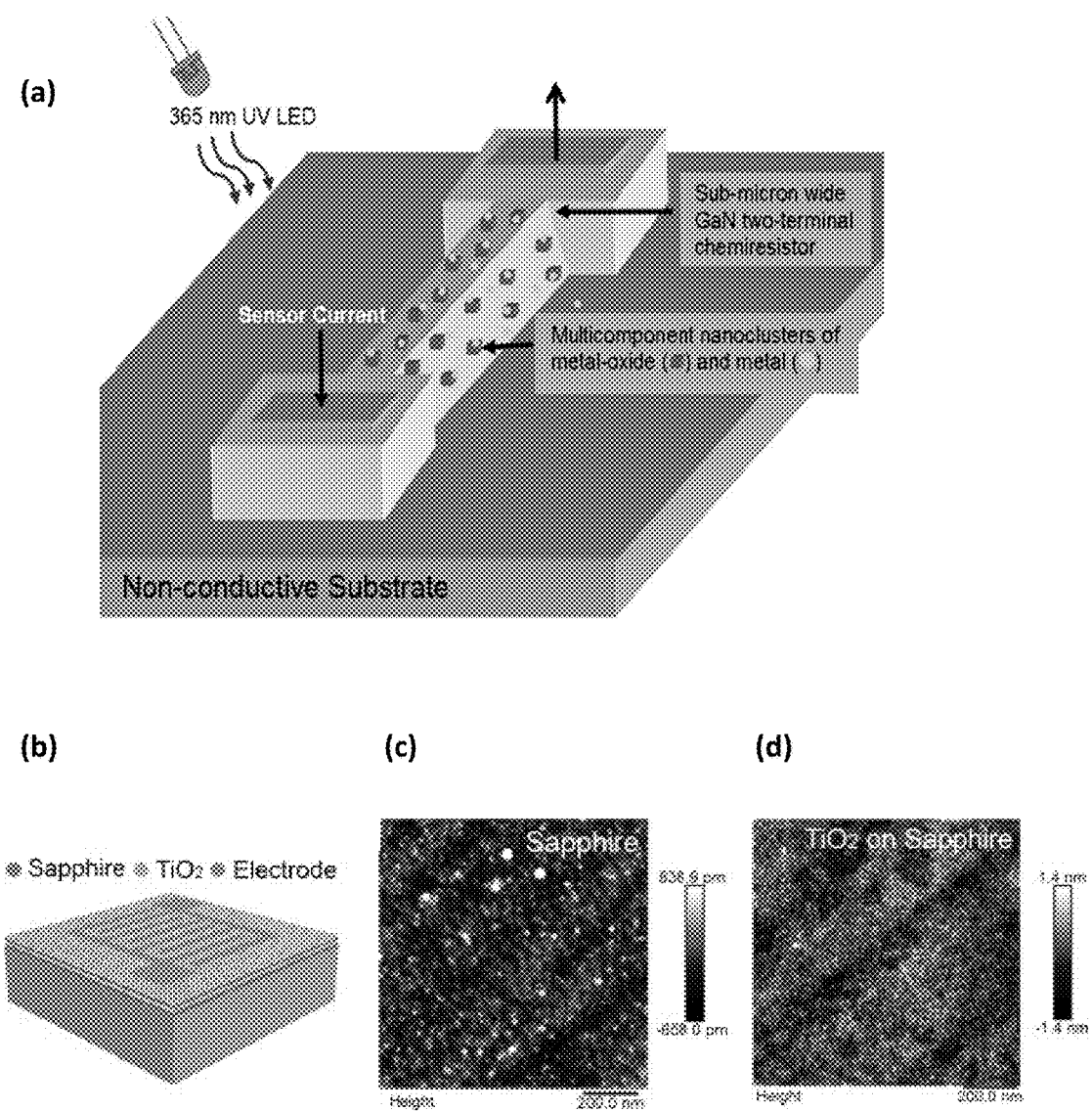
FIG. 9, plate (a) is a schematic illustration of a nanostructured semiconductor-nanocluster hybrid gas sensor according to an embodiment of the present invention. The sensor works with low-intensity light from an LED. The emission wavelength is determined by the semiconductor and metal-oxide bandgaps.

Referring to FIG. 9, an exemplary structure of a semiconductor-nanocluster hybrid sensor is illustrated. Referring to FIG. 9, plate (a), the sensor may comprise a two-terminal sub-micron wide semiconductor backbone, functionalized with nanoclusters of metal-oxides and/or metals. For example, the sensor may include a lightly-doped 0.8-0.25 µm wide semiconductor two-terminal structure on a non-conductive substrate (e.g. sapphire) formed using traditional deep UV photolithography and plasma etching. Functionalization is a discontinuous layer of multicomponent nanoclusters (e.g., each nanocluster comprising one or more photocatalytic metal-oxide nanoclusters (diameter 20 nm and smaller) and smaller metal nanoparticles (5 nm and smaller) deposited on top of it). The multicomponent design may include more than one oxide and metal types in the nanoclusters, and exhibits tailored adsorption properties by virtue of the multicomponent design. The functionalization layer is deposited using reactive sputtering technique followed by thermal treatment—all standard semiconductor microfabrication processes. The sensors work with low-intensity light, such as from an LED. The emission wavelength is determined by the semiconductor and metal-oxide bandgaps. FIG. 9, plate (b) illustrates schematically an exemplary thin-film device including a semiconductor backbone functionalized with $TiO_2$ on a sapphire substrate. The smoothness of the substrate and film after thermal processing is shown in FIG. 9, plates (c) and (d).

Surface defects of metal-oxides are the active sites for adsorption of various chemicals. However, at room-temperature the adsorbed oxygen and water are very stable. This necessitates heating in traditional metal-oxides sensors. Most metal-oxides are well-know photocatalysts, with photoexcitation wavelengths in the range of ultraviolet to visible, corresponding to the material bandgap. A disclosed approach uses dynamic surface-defects generation in the metal-oxide cluster through illumination, which allows for efficient photodesorption of adsorbed water and oxygen. This has at least two benefits: 1) low-power, room-temperature operation, which also increases the lifetime of the sensors, and 2) real-time dynamic range modulation by changing the intensity of light (for ppt level detection the intensity of the LED can be increased as compared to ppm level detection).

The sensor architecture provides for the combination of a crystalline top-down fabricated semiconductor backbone with a discontinuous nanocluster surface layer. In metal-oxide gas sensors, the resistance changes due to diffusion and adsorption of gases along the grain boundaries. As the present architecture uses a discontinuous, nano-island like metal-oxide layer, the bottleneck of gas diffusion through grain boundaries, as in traditional metal-oxide sensors, is not present. This makes the disclosed sensors respond relatively fast as compared to conventional sensors, and operable at room-temperature. Unlike traditional metal-oxide sensors, the disclosed design provides that the current is carried by the high-quality, high mobility semiconductor backbone, which makes the sensor fast. Also, the absence of conduction in the nanocluster layer makes the active layer inherently stable as compared to traditional metal-oxide thin film sensors (e.g., grain boundary motion, defect generation and propagation, and reduction of the metal-oxide layer is not possible due to the absence of a "closed-circuit").

Due to the nanocluster layer of the disclosed sensors, designed with a specific adsorption profile, they are extremely efficient in adsorbing target analytes. This enables the design of highly-selective sensors. Two component, three component, four component, or five or more component cluster designs are possible for unprecedented selectivity tailoring.

Figure 10:
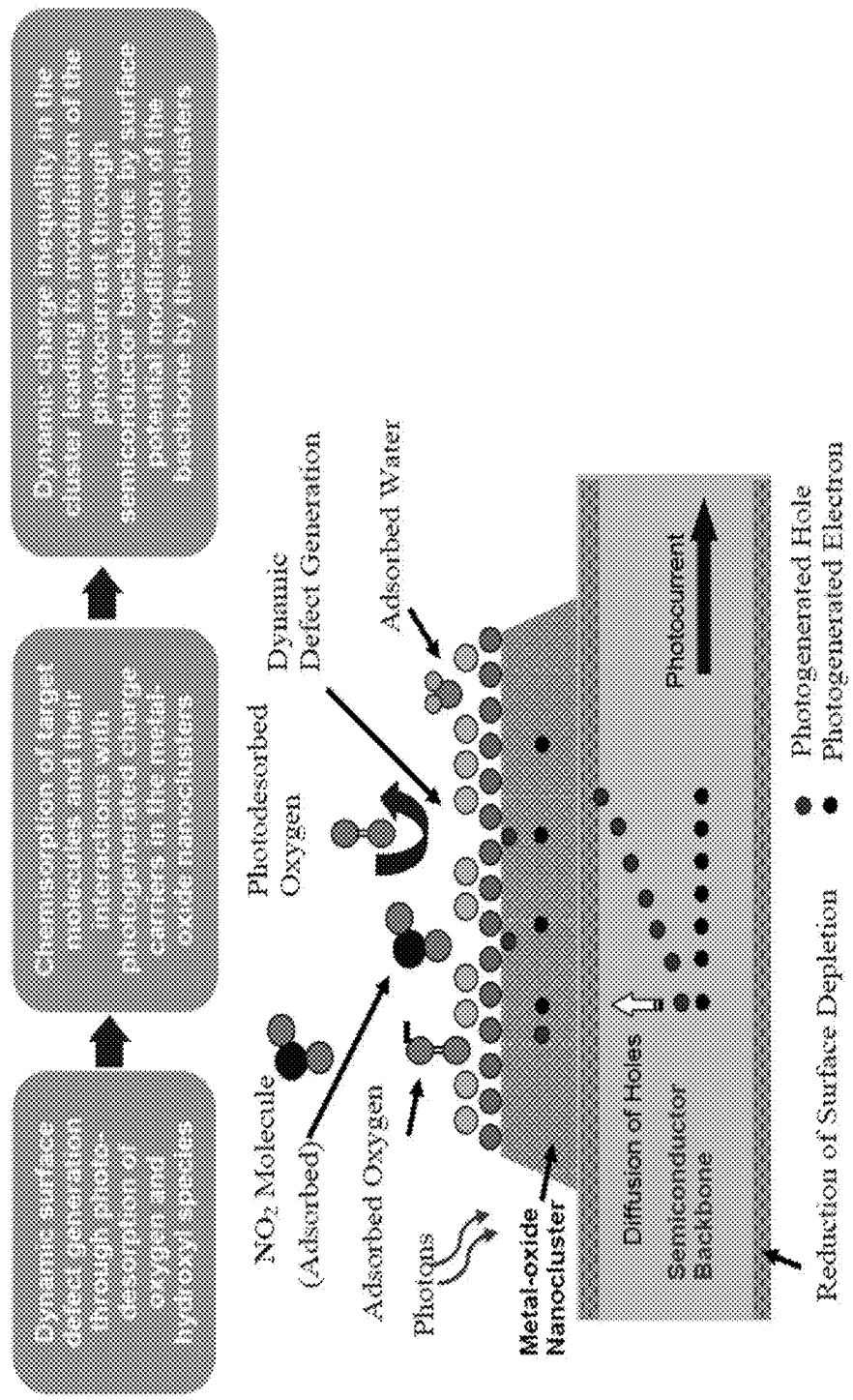
FIG. 10 is a schematic illustration of the mechanism of sensing using the disclosed nanocluster-functionalized semiconductor devices. The sensing is due to the effective separation of photogenerated charge carriers in the semiconductor backbone caused by surface potential modification of the backbone by the nanocluster upon adsorption of chemicals. The light produces electron-hole pairs in the semiconductor, and also surface defects on the cluster due to photo desorption of oxygen and water.

Most semiconductors have depletion regions associated with them. The surface band bending, which is a consequence of the surface depletion, facilitates the diffusion of the photogenerated holes to the surface. This separation of carriers effectively suppresses their recombination. The degree of separation is determined by the surface potential modification by the clusters. Such separation of photocarriers increases their lifetimes, leading to higher photocurrent and thus sensitivity towards such surface potential modifications. The processes that enable sensing of different adsorbed molecules with the disclosed multicomponent nanocluster functionalization is shown schematically in FIG. 10.

Assuming typical values of the response/recovery times for 500 ppt of $NO_2$, from the kinetic theory of gases the flux F of $NO_2$ arriving on a surface is given by the formula:

$$F = \frac{N_A P_{partial}}{\sqrt{2\pi MRT}} \qquad \text{(Equation 7)}$$

where $N_A$ is the Avagadros' number, M is the average molar weight of the molecule, P is the pressure, T is the temperature, and R is the gas constant.

For 500 ppt concentration of $NO_2$ in air, three molecules of $NO_2$ are impinging on a 20 nm diameter metal-oxide cluster per second. Now, the residence time r of an adsorbate at temperature T on a surface is given by the relation $\tau=\tau 0$ exp ($\Delta$Ha ds/RT), where $\Delta H_{ads}$ is the heat of adsorption, and $\tau 0$ is correlated with surface atom vibration (roughly $10^{-12}$ s). Thus, at 298 K the residence time for $NO_2$ molecule on $WO_3$ nanocluster is approximately 15 seconds (considering $\Delta H_{ads}$ for $NO_2$ on $WO_3$ to be 18 kcal/mol). Considering roughly $10^{21}$ $cm^{-3}$ of defect density for typical metal oxides, results in roughly 300 adsorption sites on a 20 nm diameter nanocluster. Assuming sticking coefficient of 1, by 110 seconds the surface defects are saturated. Thus, response time may be estimated to be in the order to 100 seconds, and recovery time in the order to 15-30 seconds. Although the design of the nanocluster is described from pure thermodynamic standpoint, other surface kinetics (such as diffusion, desorption) may also be considered.

Figure 11:
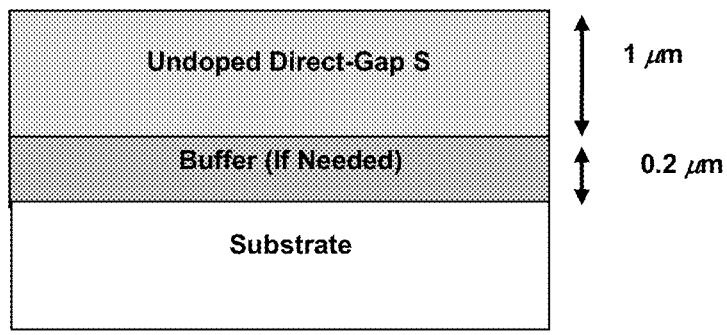
FIG. 11 illustrates schematically the epitaxial layer structure utilized in sensor device fabrication according to an embodiment of the invention.

For fabricating the sensor backbone, un-doped ($1\times10^{16}$ $cm^{-3}$) to lightly doped ($1\times10^{17}$ $cm^{-3}$) semiconductor epitaxial layer (1 µm thick) on sapphire/insulating/semi-insulating substrates may be utilized, as shown in FIG. 11. Lower doping is needed for the sensors to be photo enabled. The thickness of buffer layer controls the defects arising from lattice and thermal mismatch. Ideally suited layer structures require a relatively thin buffer layer (e.g., about 250 nm) to suppress the parasitic conduction in the buffer layer. Similar designs may also be provided with other direct gap semiconductors, such as ZnO, InN, AlGaN and virtually any other direct gap semiconductor material.

Figure 12:
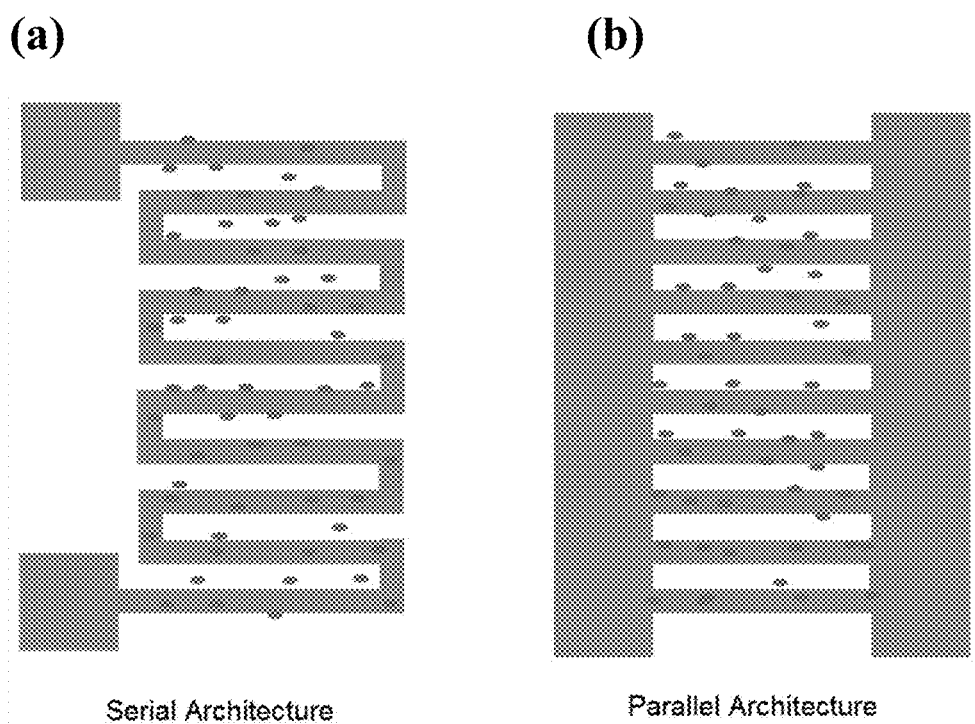
FIG. 12 illustrates schematically sensor designs according to the present invention, including a sensor having serial architecture (plate (a)), and a sensor having parallel architecture (plate (b)).

The design of submicron semiconductor backbone including physical layout and geometry is described with reference to FIG. 12. Both serial and parallel architectures for the semiconducting resistive backbone have unique advantages and disadvantages as the chemiresistor backbone. Serial architecture has higher resistance which results in lower-power operation, whereas parallel architecture produces more robust devices insensitive to material quality variation in the individual sections. However, the calculation will show that the response R is the same for both serial and parallel architecture:

$$R = \frac{R_{analyte} - R_{air}}{R_{air}} \quad \text{(Equation 8)}$$

wherein $R_{analyte}$ and $R_{air}$ are the resistances in presence of analyte and in air, respectively. However, the resolution of the sensor (i.e., smallest change in concentration it can measure as required for proposed large dynamic range sensors) is greater in a serial architecture.

Figure 13:
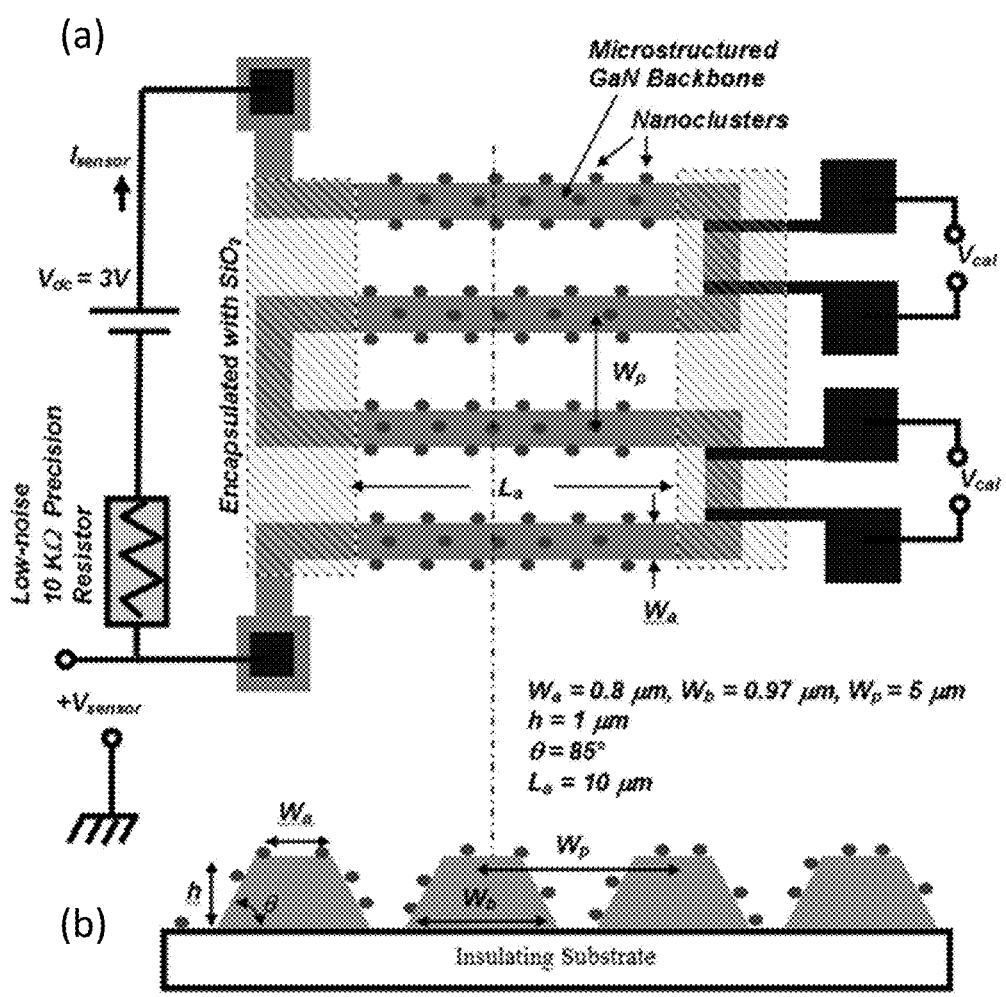
FIG. 13 are schematic illustrations of a series architecture design of a sensor with four segments, including a top view (plate (a)) and a cross-section view taken along the dashed line (plate (b)). The sensor output is the voltage between the +$V_{sensor}$ and ground pads. The $V_{cal}$ are the real-time calibration probes for baseline and temperature drift compensating.

The series sensor element provides for a meander shape, with integrated passive sections as real-time calibration elements. An exemplary design is shown in FIG. 13, plate (a). The surface area-volume ratio for this structure is roughly 3.1. The sidewalls of the backbone may be intentionally angled, such as at 85° as shown in FIG. 13, plate (b). This ensures uniform coverage of the nanoclusters on the sidewalls of the structure, and also ensures uniform photo-excitation of the semiconductor backbone. The device is biased by a standard three dc voltage source (two AA batteries in series) and the sensor output is the voltage measured between the pads $+V_{sensor}$ and ground. The design provides various benefits including: 1) high sensitivity and resolution; 2) low-power consumption; 3) simplified interface circuit; and 4) ability for real-time base-line drift calibration and temperature compensation even in presence of analytes.

Figure 14:
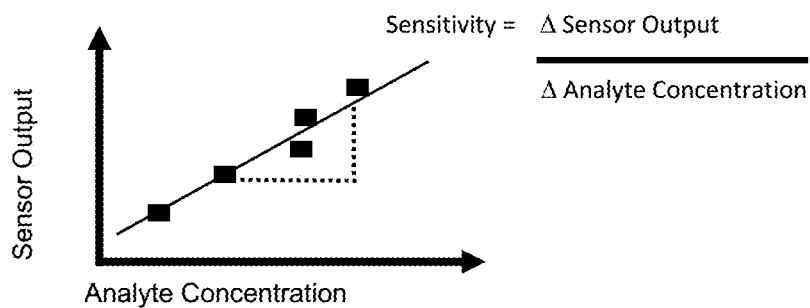
FIG. 14 illustrates graphically a generic sensor calibration curve. Sensitivity S is defined as the slope of the sensor output response vs. analyte concentration plot. The sensor output may be a change in current, voltage, or resistance.

Using circuit analysis, it can be shown that Sensitivity S (as defined in FIG. 14) may be simplified considering $R_L \ll R$ as:

$$S = \frac{R_L \times V_{dc}}{NR} \left[ \frac{1}{\frac{R}{\Delta R} + 1} \right] \quad \text{(Equation 9)}$$

wherein $R_L$ is the external low-noise precision load resistance (e.g., see FIG. 13, plate (a)), N is the number of segments, R is the resistance without analyte of single segment, and $\Delta R$ is the resistance change of the single segment in presence of the analyte, and $V_{dc}$ is the dc source voltage.

Thus for higher sensitivity, N should be small, and $R_L$ and $V_{dc}$ should be large. However, resolution of a sensor is the smallest change in concentration of the analyte it can measure (it is different from lowest detection limit), and is often limited by the noise. Considering only thermal noise current in the total sensor, the output sensor voltage noise can be expressed as:

$$V_{sensor}(\text{noise}) = R_L \sqrt{\frac{rk_B T \Delta f}{NR}} \quad \text{(Equation 10)}$$

wherein $k_B$ is the Boltzmann Constant, T is the temperature, and $\Delta f$ is the bandwidth. Considering both Equations 9 and 10, the tradeoff between high sensitivity and resolution is clear. The effect of N (i.e., number of segments) on the sensor performances such as sensitivity, detection limits, and resolution, may be investigated.

Referring again to FIG. 13, plate (a), the resistance of the active sensor area may be computed using the formula, neglecting the bends:

$$R \approx \frac{\rho \times (4 \times L)}{h \times (W_u + W_b)/2} \quad \text{(Equation 11)}$$

wherein $\rho = 1/(nq\mu)$, $\rho$ is the resistivity, n is the carrier concentration, and $\mu$ is the mobility (see also dimensions shown in FIG. 13, plate (b)).

For example, for the GaN backbone with dimensions shown in FIG. 13, the active-area photoresistance under 365 nm excitation from LED is ≈60 kΩ, assuming a mobility of 300 cm$^2$V$^{-1}$ s$^{-1}$ and electron concentration of $1 \times 10^{17}$ cm$^{-3}$. The device is considered to be excited by low-intensity (10 μW/cm$^2$) 365 nm LED. The GaN absorption coefficient $\alpha = 10^5$ cm$^{-1}$ for the 365 nm photon is assumed. If the sensor is biased with 3 V dc and with an external 10 KΩ resistor, the power dissipation is approximately only 40 μW. The sensor power dissipation when in offstate (LED turned off and the sensor has only dark current) is even lower. The total power requirement for the sensor must also include the power required for LED operation. There are several low-power UV (365 nm) LEDs (FOX GROUP) that could be run by LED drivers. Power dissipation for the LED could be low as 0.5 mW, if we drive the LED for very low intensity. Using a LED driver to control the intensity has an added benefit of the real-time dynamic range configuration.

The simplified chemiresistive architecture lends itself easily to integration with interface devices as compared to more complex devices such as metal-oxide-semiconductor field-effect transistors (MOSFETs). The nano-watt operation amplifier (OP-Amp) TS1001 from Touchstone Semiconductor is identified, which can provide a gain of 100 when operated in single-input voltage amplifier configuration. The Op-Amp operated from a single AA battery dissipated about 1 μW.

In one implementation, a feature of the present design is the inclusion of the voltage probes ($V_{cal}$) for calibration of base line drift of the photoresistance of the total structure. As the area under the calibration probes is encapsulated with thick SiO$_2$, the voltage drop ($V_{cal}$) for a fixed intensity of illumination through the entire structure will enable compensation for drift in the baseline photoresistance arising from persistence photoconductivity or temperature-induced drift.

Another feature of the present design is the "tailored" adsorption profile through the multicomponent nanocluster design, as described above. The design provides for suppressing the competitive adsorption of an interfering chemical on a surface with two different adsorption profiles, which is achieved using a primary and a secondary component.

Figure 16:
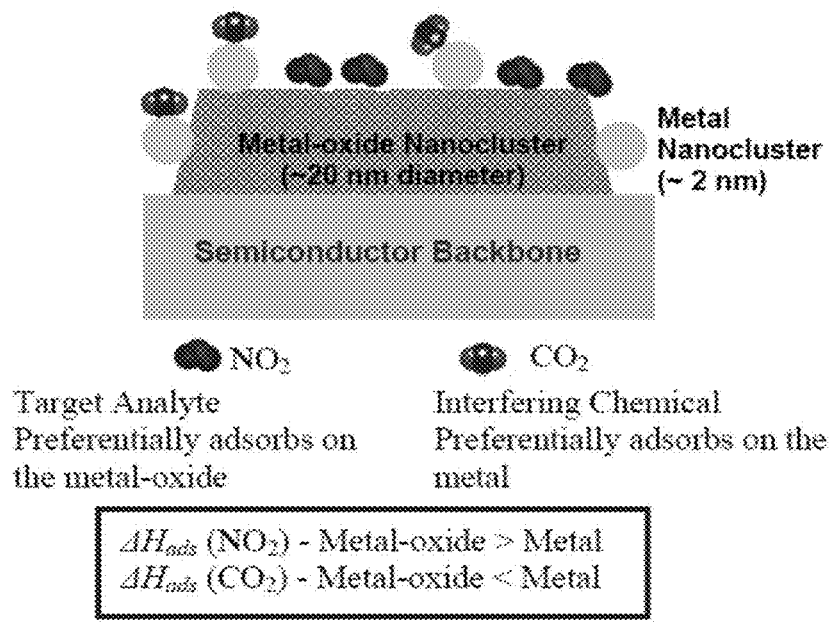
FIG. 16 is a schematic illustration showing selectivity tuning using a multicomponent design of nanoclusters. As shown, the target analyte is $NO_2$ and the interfering chemical is $CO_2$.

In this regard, FIG. 16 illustrates an exemplary multicomponent design for the target analyte of NO$_2$ and for the interfering chemical of $CO_2$. Adsorption profile for another target analyte or set of analytes along with a set of interfering chemicals may alternatively be provided utilizing a similar configuration. The primary metal-oxide component is chosen so that the heat of adsorption of $NO_2$ on its surface is large compared to $CO_2$. The secondary component (e.g., the metal) is chosen with the heat of adsorption for $CO_2$ larger than the metal-oxide. Thus $NO_2$ and $CO_2$ preferentially adsorb on the metal-oxide and the metal, respectively. When $NO_2$ is adsorbed on the metal-oxide, it interacts with the photogenerated charge carriers, producing modulation of the semiconductor backbone photocurrent, as explained above. However, when $CO_2$ is adsorbed on the metal, due to the large concentration of electrons, there is minor change in the cluster potential. Consideration of other effects, such as catalytic decomposition on the metal, spill-over from the metal to metal-oxide, and change of metal-work function due to adsorption of gases, may also be appropriate.

Due to the highly dispersed nature of the metal phase, even if there is a change in the physical properties of the metals, it has only marginal impact on the cluster properties. Although the general design principles are described, the specific designs of the appropriate clusters may be fine-tuned for optimal performance and selectivity. For example, Table V below demonstrates possible cluster designs for $NO_2$ and benzene sensing. Considering the heat of adsorption of $NO_2$ on $WO_3$ and Pt, bigger $WO_3$ clusters with much smaller and dispersed phase of Pt may be favorable. Although, adsorption energy for $NO_2$ is comparable on both $WO_3$ and Pt, due the higher surface area of metal-oxide clusters, most of $NO_2$ will adsorb on the $WO_3$, whereas $CO_2$ will mostly adsorb on the Pt. For BTEX sensing, the $TiO_2$/Fe is favorable.

TABLE V

Heat of adsorption on different candidates for the multicomponent cluster design.

Possible Cluster Designs for $NO_2$ sensing:

| Metal-Oxide/Metals | $NO_2$ (kcal/mol) | $CO_2$ (kcal/mol) |
|---|---|---|
| MgO | 9.0 | 3.5 |
| $TiO_2$ | 21.0 | 29 |
| $WO_3$ | 18.4 | negligible |
| Fe(111) | 64.5 | 69 |
| Pt(111) | 19 | 40.5 |

Possible Cluster Designs for Benzene sensing:

| Metal-Oxide/Metals | Benzene (kcal/mol) | $CO_2$ (kcal/mol) |
|---|---|---|
| $TiO_2$ | 15.2 | 29 |
| Fe (111) | 22 | 69 |

Note that the values in Table V are average adsorption energies at room temperature for low adsorbate coverage. The values are collected from experimental results (temperature programmed desorption and calorimetric studies) and theoretical calculations (such as density function theory). The values shown are for common and stable oxide surfaces. Experimental heat of adsorption values are dependent on various factors, including the morphology and crystal orientation of the surface.

Figure 15:
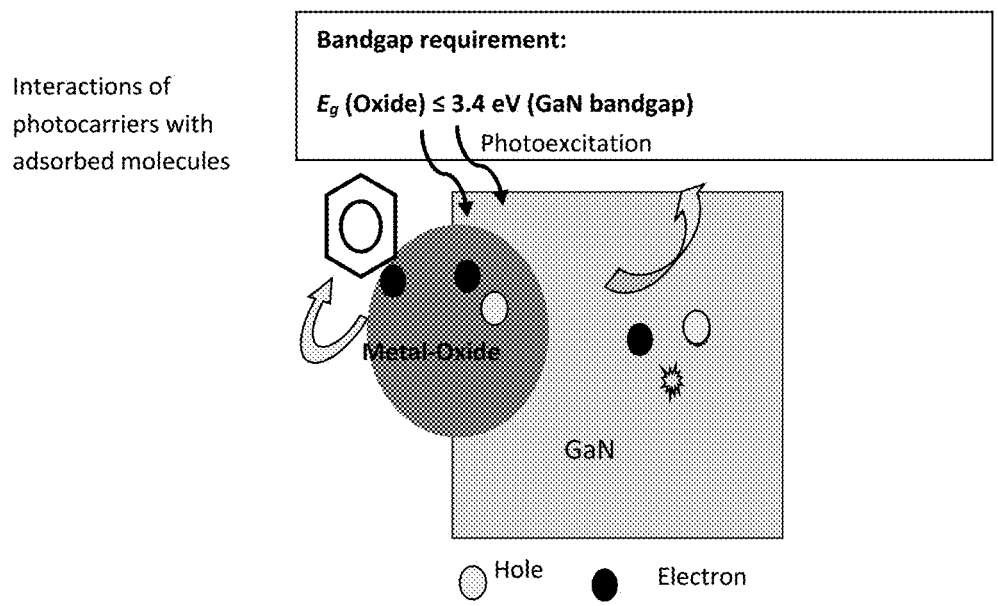
FIG. 15 is a schematic illustration of photoexcitation of both the metal-oxide cluster and the GaN backbone using 365 nm light.

Other design considerations for the nanoclusters include:

1) Bandgap of the oxide: as single wavelength excitation is used for both photodesorption of surface oxygen and hydroxyl species, and for creating photocarriers in the semiconductor (e.g. GaN), the bandgap of the oxide should be lower or equal to GaN bandgap (as shown in FIG. 15). Candidates are shown in Table VI below.

TABLE VI

Bandgaps of Common Metal Oxides

| Metal-Oxides | Bandgap (eV) |
|---|---|
| MgO | 7.1 |
| $TiO_2$ | 3.2 |
| $WO_3$ | 2.8 |
| $Fe_2O_3$ | 2.1 |
| $V_2O_5$ | 2.3 |
| NiO | 3.6 |
| $Al_2O_3$ | 7.0 |

Candidates are in bold and underlined, $E_g$ <3.4 eV.

2) Nature of surface defect types: surface defects (i.e. the active adsorption sites) of metal-oxides are of three types: bronstead, lewis-acid/base sites, and redox sties. Organic compounds such as benzene predominantly adsorb by dehydgrogenetion (i.e., removal of H+) requiring surface lewis sites. On the other hand, $NO_2$ predominantly adsorbs as surface nitrate ($NO_3^-$), requiring base sites. Most metal-oxide surfaces at room-temperature are hydroxylated, and thus photoexcitation will increase the concentration of one type of predominant defects.

3) Redox potentials of the oxide: redox potentials of oxides indicate the ability of photogenerated carriers to oxidize or reduce any adsorbed molecule. Depending on whether molecules will be oxidized or reduced on the surface, they interact with charge carriers differently in the clusters.

4) Stability of the adsorbates: Stability of the adsorbed species is an important consideration, as it determines the recovery time, and ultimately usability of the sensors. As can be seen for Fe, where the very high adsorption energy might produce very stable NO adsorbed species on the surface, rendering the nanoclusters inactive after exposure to high concentrations of $NO_2$.

5) Nature of the adsorbed species (molecular or dissociative): nature of the adsorbed species determines the photochemical reaction pathways and ultimately the sensitivity. Additional multicomponent nanocluster designs for $NO_2$ and BTEX sensing are shown in Table VII.

TABLE VII

Possible designs of nanoclusters

| Metal-Oxides/Metal | Target Analyte |
|---|---|
| $WO_3$/Pt | $NO_2$ |
| $TiO_2$/Fe | BTEX |

The use of heterogeneous metal-oxide supported metal catalysts in industrial production, abatement, and remediation for the past few decades has been extensive, and generated an exhaustive body of literature that may be readily utilized for nanocluster designs according to the present invention. Indeed, some of the systems are well-understood, so that a desired selectivity outcome may be readily predicted. The well-known strong metal/support interactions (SMSI) effects in heterocatalysts are different, as the metals are not reduced on the oxides in the disclosed devices.

Computing the size and coverage of the clusters is an important consideration, given the size and coverage of the NCs ultimately determines the overall sensitivity of the device. Thus, determination of the most effective size and coverage of the clusters is desirable. It is known that the surface area and relative particle size has a significant effect on the catalytic properties of metals and metal oxides. However, due to the presence of metals on the metal-oxide clusters, there will be significant depletion of the metal-oxide clusters. Thus, overly small metal-oxide clusters would be substantially depleted and hamper effectiveness, whereas overly large clusters would also result in lower sensitivity. Consideration of the nature of the depletion regions formed by such nano-sized metal clusters on a semiconductor is therefore prudent.

The classical Schottky model depletion theory cannot predict accurately the zero-bias depletion width produced by metallic nanoclusters on a semiconductor. According to Zhdanov's model, the depletion depth associated with such metal nanoclusters on a semiconductor can be estimated by the following relationship:

$$w_d = \left(\frac{3r_o V_{bi}}{2\pi q^2 N_d}\right)^{1/3} \quad \text{(Equation 12)}$$

wherein $w_d$ is the depletion width, $r_c$ is the radius of the nanocluster, $V_{bi}$ is the built-in voltage for the junction, q is the elementary charge, and $N_d$ is the dopant concentration in the semiconductor.

Figure 17:
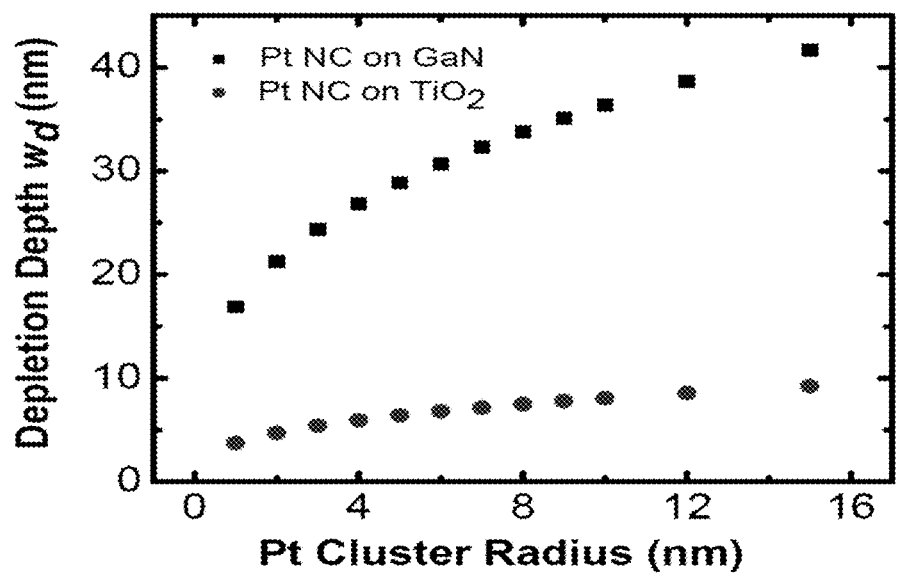
FIG. 17 illustrates graphically depletion depth induced by Pt nanoclusters on GaN and $TiO_2$ (as calculated by Equation (12) below).

The plot in FIG. 17 demonstrates the depletion width of $TiO_2$ clusters due to Pt particles. It is clear that 4 nm of Pt clusters on 20 nm diameter $TiO_2$ clusters would produce depletion of about 5 nm in the $TiO_2$.

Coverage of the metal-oxide nanocluster functionalization is determined by the limit of formation of continues metal-oxide film. The coverage is dependent on various parameters such as metal-oxide wetting of the semiconductor, morphology of phases formed after thermal treatment, etc., and may be verified by SEM imaging. The metal coverage should be sparse to ensure only partial depletion of the clusters.

With regard to fabrication, techniques such as wet chemical etching may not be suitable for etching nanoscale, high aspect-ratio nanostructures due to undercutting of the mask and sloped sidewalls. Hence, the development of a dry etching process with relatively less low damage and precise-depth control capability is preferred for the fabrication of nanostructures. Such etching of semiconductor nanostructures is described in further detail in Example 4 below.

Figure 18:
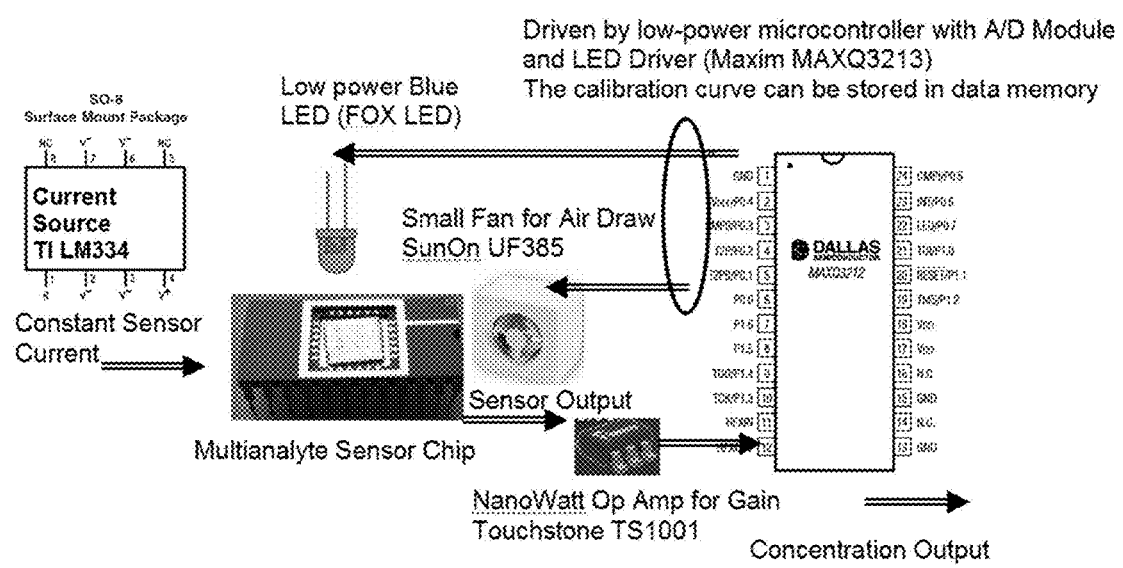
FIG. 18 is a schematic illustration of an integration scheme for standalone system, showing components at roughly their actual size.

Referring to FIG. 18, the components for an exemplar interface circuit is illustrated. The LED intensity may be controlled by the microcontroller (MAXQ3213, with a LED driver). By relatively simple design change of a selected multicomponent cluster, different applications are readily provided. In addition, using wide bandgap material as a backbone enables the sensor to work at elevated temperatures, and in presence of radiation and other harsh environmental conditions.

As shown in Table VIII below, the possible designs of the multi-component nanoclusters are virtually unlimited, resulting in the ability to provide sensors for numerous applications.

TABLE VIII

Exemplary Designs of Multicomponent Nanoclusters

| Nanocluster Components: | | |
|---|---|---|
| Semiconductor | Metal Oxide: | Metal: |
| GaN | Titanium Oxide | Titanium |
| InN | Tin Oxide | Nickel |
| AlGaN | Iron Oxide | Chromium |
|  | Magnesium Oxide | Cobalt |
|  | Vanadium Oxide | Ruthenium |
|  | Nickel Oxide | Rhodium |
| ZnO | Zirconium Oxide | Gold |
| InAs | Aluminum Oxide | Silver |
|  | Copper Oxide | Platinum |
|  | Zinc Oxide | Palladium |
|  | Strontium Oxide | Vandium |

Figure 53:
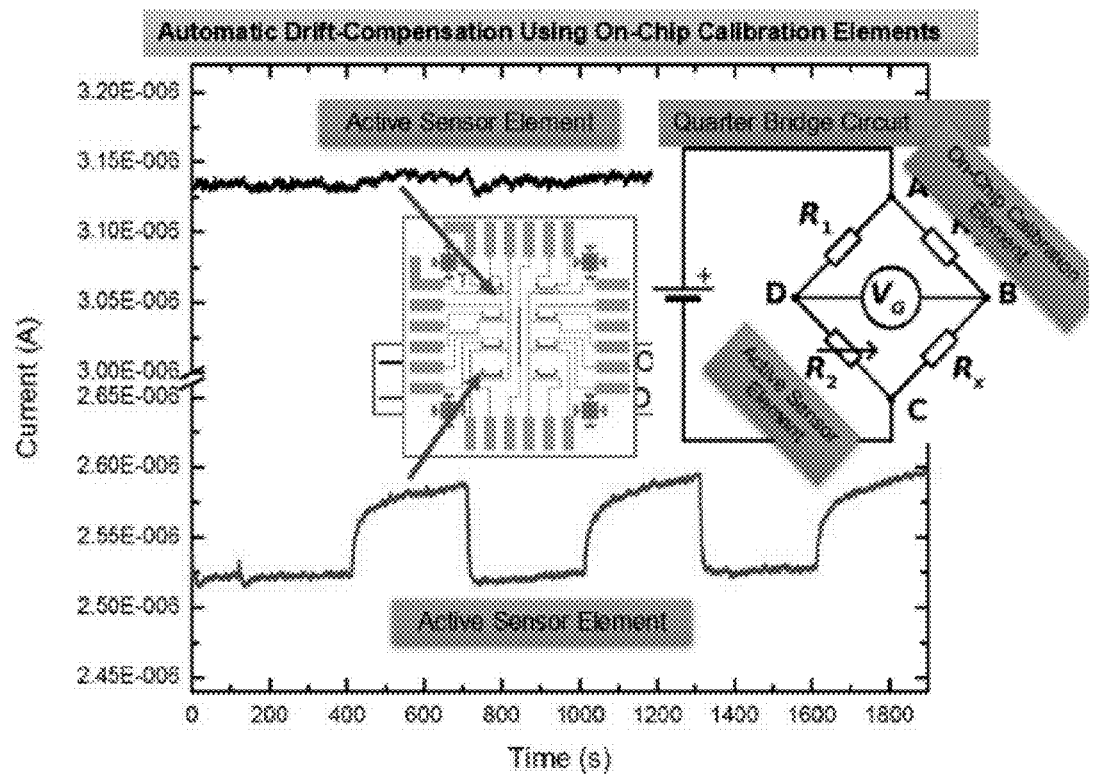
FIG. 53 illustrates schematically an exemplary layout of on chip elements of a sensor device in accordance with the present invention.
Figure 54:
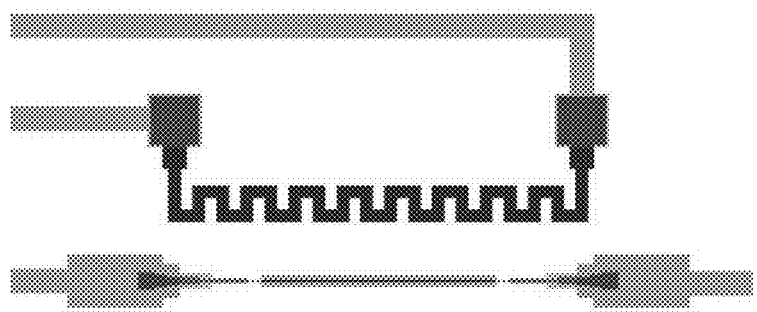
FIG. 54 illustrates schematically a micro-heater embedded into a sensor device in accordance with disclosed embodiments of the present invention.
Figure 55:
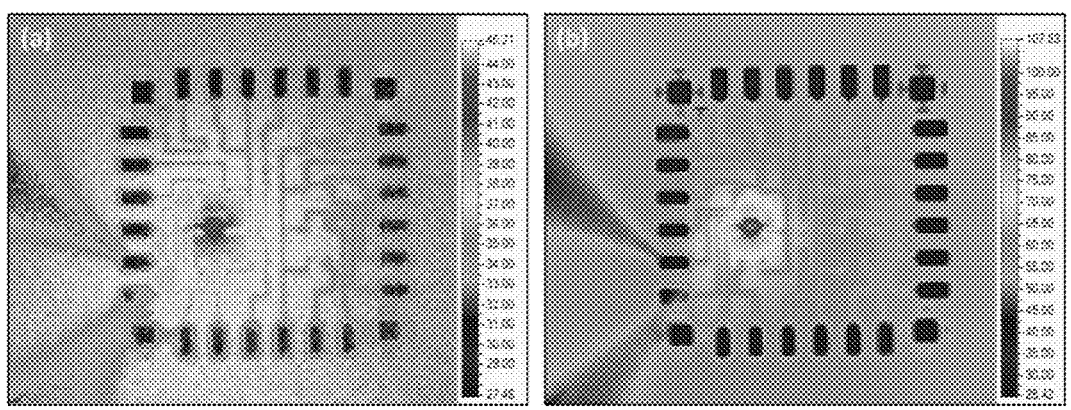
FIG. 55 illustrates the temperature profile of 50 μm microheater made from a Ti/Ni metal stack MH recorded at 5 V bias voltage (plate (a)) and 10 V bias voltage (plate (b)).

Thus, in accordance with the disclosed methodologies, sensor devices suitable for a wide range of applications are achieved. Further, the particular architecture of the sensor devices may be readily tailored for the desired application and associated conditions, as well as one or multiple active sensor elements configured for sensing particle targets. For example, an exemplary sensor device includes eight individually addressable active sensor elements, as shown in FIG. 53, which can each detect a different target analyte (e.g., various gases). The sensor device may include an on-chip calibration element for automatic drift compensation. The sensor device may also include an on-chip micro-heater, as shown in FIG. 54, for stabilizing temperature and/or humidity. The temperature profiles of a 50 μm microheater made from a Ti/Ni metal stack MH recorded at 5 V bias voltage and 10 V bias voltage are shown in FIG. 55, plates (a) and (b), respectively.

Thus, the disclosed sensor devices may comprise various active sensor elements and passive elements for formation of on-chip circuits. Multiple active elements may be provided with a combination of different functionalization to detect multiple gases in a single chip. The chip may include precise passive elements (elements which have the same semiconductor backbone but passivated from the environment), for calibration on the same chip, which has the same temperature coefficient for current as the active sensor element. Thus, any change due to the temperature or aging can be a calibrated out using the on-chip calibration element(s). Using such on-chip components (e.g., see FIG. 53), bridge circuits may be provided directly on the chip, allowing for sensor devices with high resolution.

Although the sensor devices may comprise a micro-heater element as noted above, such element is not required. The disclosed sensor devices do not need to be heated for sensing, and are capable of sensing a host of gases at room temperature. Total power consumption is extremely low (e.g., an exemplary 8 active sensor element device provided for a total power consumption about 10 microwatts. Further, the disclosed sensor devices are stable and recoverable even in the presence of corrosive gases (e.g, HCN, $CL_2$, HCl, etc), and capable of withstanding very high gas concentrations. The sensor devices are also capable of operating in oxygen rich or relatively lean conditions.

In accordance with disclosed embodiments, the active sensor(s) elements are designed by first selecting a nanoclusters and/or a layer of a base photocatalytic metal oxide (e.g., $TiO_2$, $V_2O_5$, $Cr_2O_3$, Fe2O3, CoO, NiO, CuO, ZnO, $ZrO_2$, $WO_3$, $MoO_3$, $SnO_2$). Nanoclusters of a catalytic metal (e.g., Ti, V, Cr, Fe, Co, Ni, Cu, Al, Zr, Nb, Mo, Ru, Rh, Pd, Ag, Hf, Ta, W, Re, Ir, Pt, Au) are then applied on top of the base photocatalytic metal oxide nanoclusters. Alternatively in other embodiments, nanoclusters of a second photocatalytic metal oxide different than the base metal oxide are applied on top of the base metal oxide, providing for dual metal oxide functionalizations. Thus, the sensor element comprises a base layer or nanoclusters of a first metal-oxide, and nanoclusters of a second metal oxide or metal. The selection of the particular metal oxide and metal provides for the desired selectively.

Figure 56:
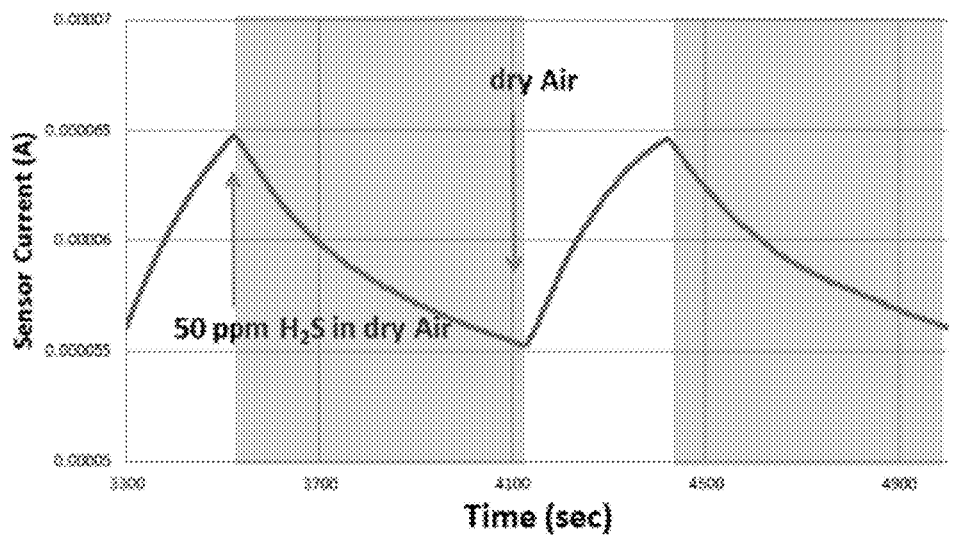
FIG. 56 illustrates graphically the dynamic response of a functionalized GaN sensor device for sensing H$_2$S (concentration 50 ppm) in dry air.
Figure 57:
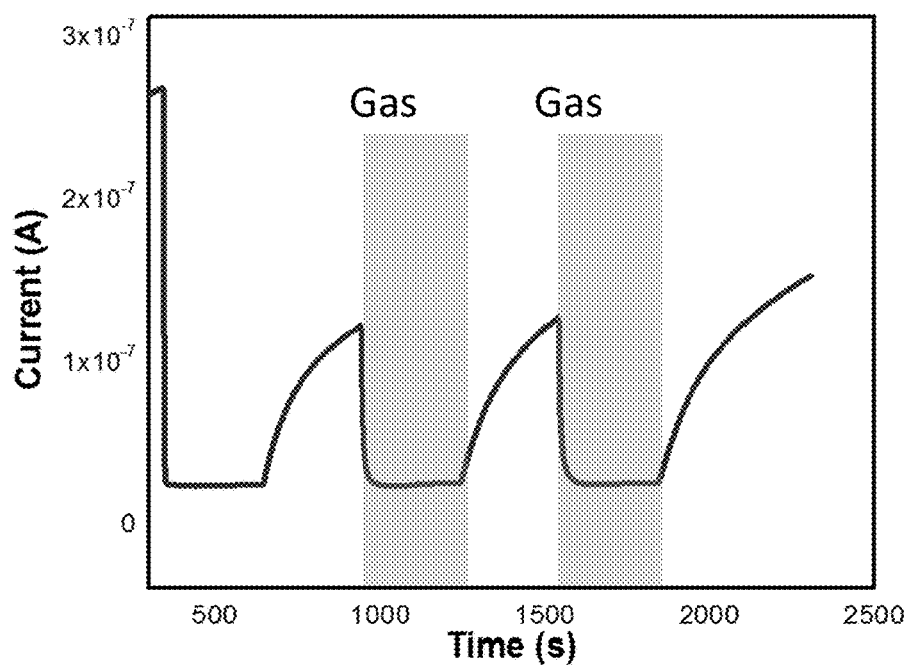
FIG. 57 illustrates graphically the dynamic response of a functionalized GaN sensor device for sensing NO$_2$ (concentration 500 ppm) in dry air (22° C., relative humidity 0-5%).
Figure 58:
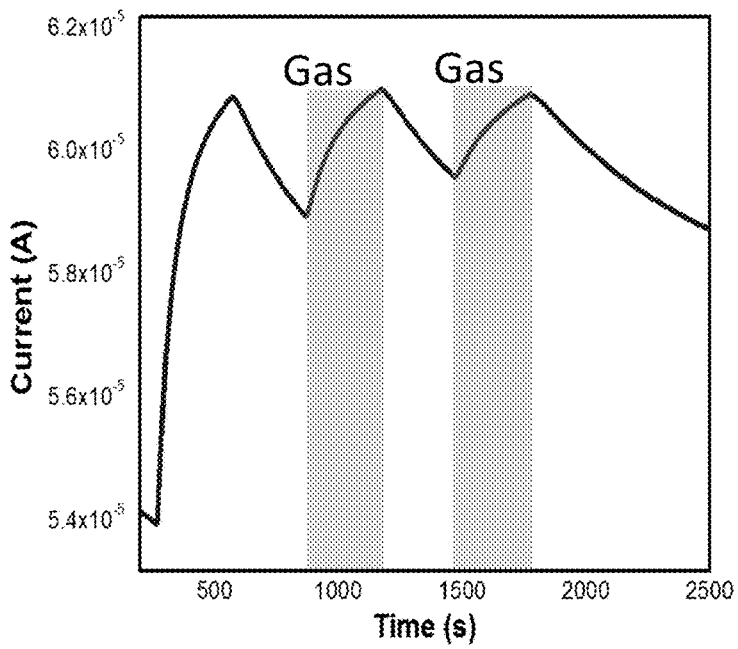
FIG. 58 illustrates graphically the dynamic response of a functionalized GaN sensor device for sensing SO$_2$ (concentration 10 ppm) in dry air (22° C., relative humidity 0-5%).
Figure 59:
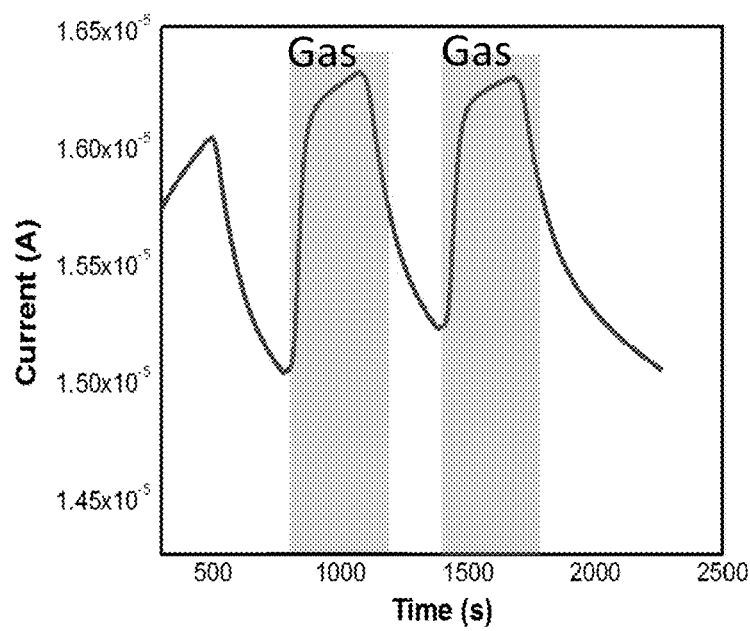
FIG. 59 illustrates graphically the dynamic response of a functionalized GaN sensor device for sensing CO$_2$ (concentration 5000 ppm) in dry air (22° C., relative humidity 0-5%).

For example, the dynamic response of functionalized GaN NW with selected metal oxide for selectively sensing hydrogen sulfide ($H_2S$) in dry air is shown in FIG. 56. The response of the functionalized GaN NW for sensing $NO_2$ in dry air is shown in FIG. 57. The response of the functionalized GaN NW for sensing $SO_2$ in dry air is shown in FIG. 58. The response of the functionalized GaN NW for sensing $CO_2$ in dry air using the metal oxide sensor devices of the present invention is shown in FIG. 59. Thus, a wide range of target gases, from reducing to oxidizing to inert gases, is achieved.

A summary of operational and performance specifications of sensing devices in accordance with disclosed embodiments is set forth in Table IX below:

| Analyte | Range of Detection | Response (%) = $(R_{gas} - R_{air}/R_{air})$ |
| --- | --- | --- |
| Ammonia | 1-100 ppm | 15 |
| Chlorine | 0.5-10 ppm | 212 |
| Hydrogen chloride | 1-100 ppm | 74 |
| Hydrogen cyanide | 1-100 ppm | 10 |
| Hydrogen sulphide | 10-1000 ppm | 20 |
| Hydrogen | 0.5-10% | 500 |
| Oxygen | 10-30% | 40 |
| Carbon dioxide | 01.-1% | 2 |
| Carbon monoxide | 10-300 ppm | 15 |
| Nitrogen dioxide | 100-500 ppm | 2 |
| Nitric oxide | 5-1000 ppm | 2.6 |
| Methane | 50-5000 ppm | 9 |

Figure 60:
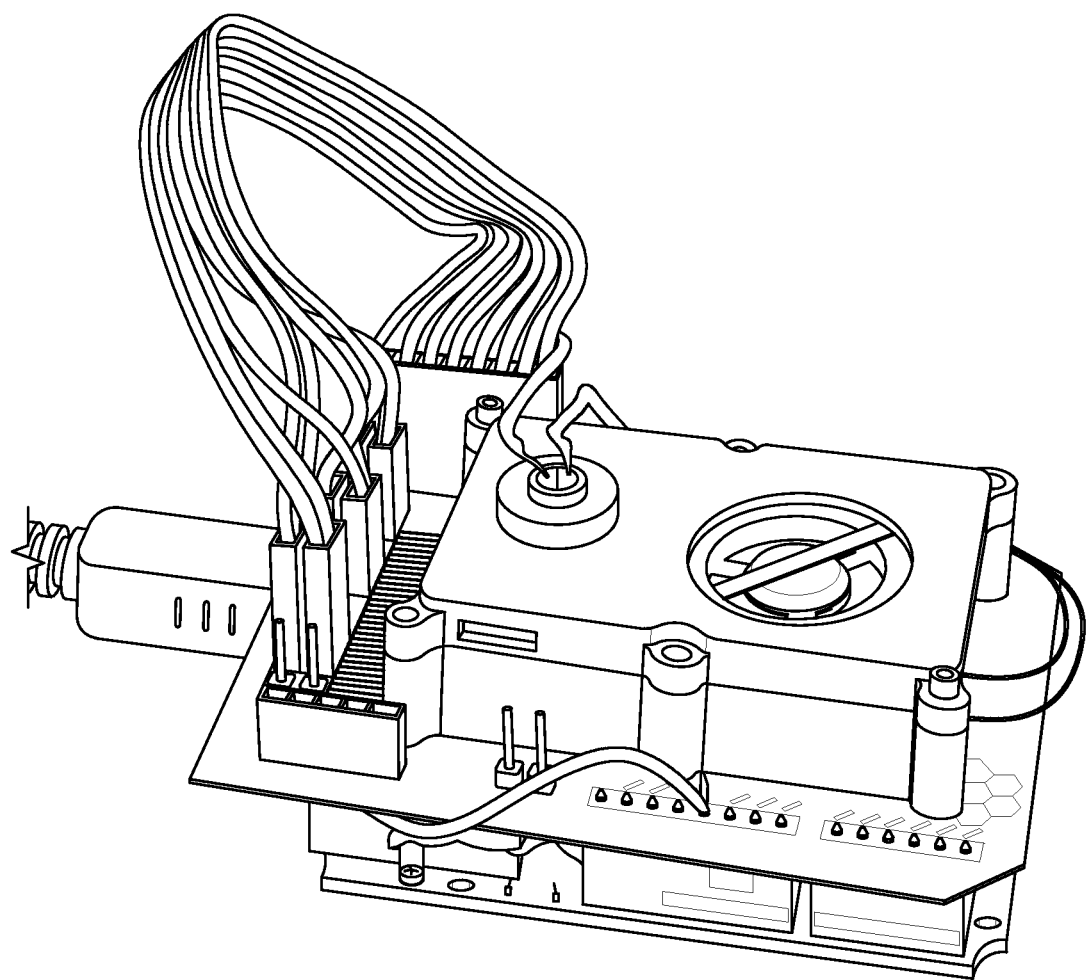
FIG. 60 illustrates an exemplary sensor module in accordance with the present invention.

The disclosed devices are suitable for environmental monitoring, hazmat, large-scale industrial monitoring and control, explosive threat detection, and other markets where rapid detection of gases and chemicals in air is desired. Compared to conventional sensors, the disclosed sensors of the present invention are extremely small (e.g., 4 mm×4 mm, or 2.5 mm×2.5 mm, or smaller) and inexpensive, exhibit low power consumption (e.g., less than 100 microwatts, and in some embodiments less than about 10 microwatts), but capable of sensing a large dynamic range (e.g., 100 parts per billion to >2%), detect a variety of chemicals under various conditions with no cross-sensitivity (thus minimizing false positives), and exhibit a long operating life. In addition, the disclosed sensors of the present invention may be manufactured using the same manufacturing methodologies utilized for producing conventional integrated circuits. An exemplary sensor module is shown in FIG. 60, which has dimensions of about 8 cm×6 cm×1 cm, a weight of 0.4 pounds, power consumption requirements for continuous operation of about 0.2 watts, eight active sensor elements or channels for simultaneous measurement of eight different target gases, and including a built-in air sampling element with microblower.

The disclosed sensor devices may be installed in residential and commercial buildings for on-demand ventilation control, resulting in a decrease in energy consumption. The sensors can detect the presence of harmful VOCs (Benzene, Xylene, and formaldehyde), which are often emitted by building materials, paints, and furniture, and are also associated with human metabolism. After detecting an increase in the levels of targeted harmful chemicals, the ventilation system may be adjusted for safety, comfort and health of the occupants. Alternatively or in addition, the sensors could monitor CO levels and gas leaks in buildings for safety. Thus, the disclosed sensor technology may be readily implemented in indoor monitoring systems, thereby generating large cost savings in terms of energy efficiency, health of the occupants, and low-maintenance costs.

In case of accidental release of chemicals, the disclosed sensors are suitable for use by first-responders to detect the presence of chemicals and associated hazards. Thus, the challenges of a disaster may be managed more safely and efficiently. The disclosed hybrid sensor technology may be implemented in ultra-small, handheld units, which identify multiple hazardous materials with low power consumption. Such devices would be ideal for first responders.

The disclosed sensors are also suitable for industrial monitoring applications. For example, the sensors may be used for monitoring different gases for process control in industrial facilities such as oil refineries, manufacturing plants, etc. They may be installed at various points throughout an industrial facility for point detection for leaks of toxic chemicals. The may also be implemented in personal monitoring devices for recording personal exposure levels for compliance purposes with state and federal maximum exposure level regulations. The disclosed technology therefore promises unlimited control over the sensor design, thus having the ability to produce sensors for various different industries and processes.

Implementations of the disclosed technology for law enforcement and safety applications are also provided. For example, the disclosed sensors may be utilized in breath analyzers for law-enforcement and individual use. The hybrid sensors may also be integrated into hand-held devices (e.g., cell phones) as plug-in modules to existing devices. For example, the disclosed sensor may be integrated into a hand-held device to enable a user to check his or her blood alcohol level.

Implementations of the disclosed sensor technology are also suitable for defense and security applications. The sensors may be used for safety monitoring in public places such as subway/rail stations, airports, public buildings, and in transit systems. For example, the sensors may be utilized to monitor and detect deliberate release of harmful chemicals and explosives, thus protecting civilians from attacks. They may also be integrated into equipment carried or worn by soldiers for detection of harmful chemicals, explosives, or other terrorist elements.

Having generally described the invention, the same will be further understood through reference to the following additional examples, which are provided by way of illustration and are not intended to be limiting of the present invention unless specified.

EXAMPLES

Example 1

Nanowire-nanocluster hybrid chemical sensors were realized by functionalizing gallium nitride (GaN) nanowires (NWs) with titanium dioxide ($TiO_2$) nanoclusters for selectively sensing benzene and other related aromatic compounds.

Materials and Methods

Figure 19:
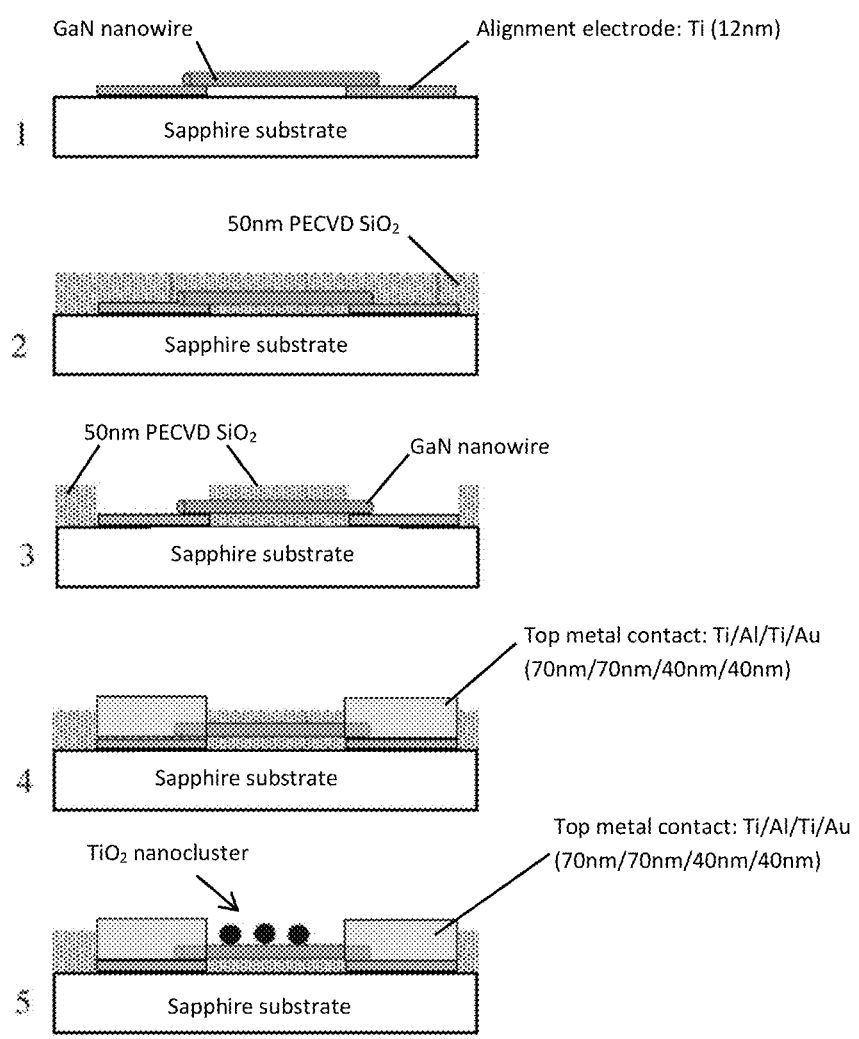
FIG. 19 is a schematic illustration of a hybrid sensor fabrication process according to the present invention.

C-axis, n-type, Si-doped GaN grown by catalyst-free molecular beam epitaxy on Si (111) substrates were utilized. For details of NW growth, see Bertness K A et al. (2008) "*Mechanism for spontaneous growth of GaN nanowires with molecular beam epitaxy*," J. Crystal Growth 310(13):3154-3158). An exemplary process of sensor fabrication is shown in FIG. 19. Post-growth device fabrication was done by dielectrophoretically aligning the nanowires on 9 mm×9 mm sapphire substrates (see Motayed A et al. (2006) "*Realization of reliable GaN nanowire transistors utilizing dielectrophoretic alignment technique*," J. Appl. Phy. 100: 114310). The device substrates had 12 nm thick Ti alignment electrodes of semi-circular geometry with gaps between them ranging from 4 µm to 8 µm. After the alignment of the nanowires, the samples were dried at 75° C. for 10 min on a hot plate for evaporation of the residual solvent. This was followed by a plasma enhanced chemical vapor deposition (PECVD) of 50 nm of $SiO_2$, at a deposition temperature of 300° C. This passivation layer was deposited to ensure higher yield for the fabrication process.

After the oxide deposition, photolithography was performed to define openings for the top contact. The oxide in the openings was etched using reactive ion etching (RIE) with $CF_4/CHF_3/O_2$ (50 sccm/25 sccm/5 sccm) gas chemistry. The top contact metallization was deposited in an electron-beam evaporator with base pressure of $10^{-5}$ Pa. The deposition sequence was Ti (70 nm)/Al (70 nm)/Ti (40 nm)/Au (40 nm). The oxide layer over the nanowires between the end contacts was then etched in buffered HF etching solution for 15 seconds. A negative resist was used to protect the end metal contacts from the etching solution.

The $TiO_2$ nanoclusters were deposited on the exposed GaN NWs using RF magnetron sputtering. The deposition was done at 325° C. with 50 sccm of Ar flow, and 300 W RF power. The deposition rate was about 0.2 Å/s. Thermal annealing of the complete sensor devices (GaN NW with $TiO_2$ nanoclusters) was done at 650° C. to 700° C. for 30 seconds in a rapid thermal processing system with 6 slpm (standard liter per min) flow of ultrahigh purity Ar. A relatively slow ramp rate of 100° C. per min was chosen to reduce the stress in the metal-nanowire contact area during heating. The anneal step was optimized to facilitate Ohmic contact formation to the GaN NWs and also to induce crystallization of the $TiO_2$ clusters. Additional lithography was performed to form thick metal bond pads with Ti (40 nm) and Au (160 nm).

The crystallinity and phase analysis of the sputtered $TiO_2$ films were assessed by X-ray diffraction (XRD). The XRD scans were collected on a Bruker-AXS D8 scanning X-ray micro-diffractometer equipped with a general area detector diffraction system (GADDS) using Cu-Kα radiation. The two-dimensional 2θ-X patterns were collected in the 2θ=23° to 51° range followed by integration into conventional Ω-θ scans. The microstructure and morphology of the sputtered $TiO_2$ films used for fabrication of sensors were characterized by high-resolution analytical transmission and scanning transmission electron microscopy (HRTEM/STEM) and cold field-emission scanning electron microscopy (FESEM). GaN nanowires with sputtered $TiO_2$ were deposited onto a lacey carbon films supported by Cu-mesh grids and analyzed in a 300 kV TEM/STEM microscope. The instrument was equipped with an X-ray energy dispersive spectrometer (XEDS) and an electron energy-loss spectrometer (EELS) as well as bright-field (BF) and annular dark-field (ADF) STEM detectors to perform spot and line profile analyses.

The device substrates, i.e., the sensor chips, were wire-bonded on a 24 pin ceramic package for the gas sensing measurements. The device characterization and the time dependent sensing measurements were done using an Agilent B1500A semiconductor parameter analyzer. Each sensor chip was placed in a custom-designed stainless steel test chamber of volume 0.73 $cm^3$ with separate gas inlet and outlet. The test chamber had a quartz window on top for UV excitation provided by a 25 W deuterium bulb (DH-2000-BAL, Ocean Optics) connected to a 600 µm diameter optical fiber cable with a collimating lens at the end for uniform illumination over the sample surface. The operating wavelength range of the bulb was 215 to 400 nm. The intensity at 365 nm measured using an optical power meter was 375 nW $cm^{-2}$. For all the sensing experiments regular breathing air (<9 ppm of water) was used as the carrier gas. A wide range of concentrations from 1% to as low as 50 parts per billion (ppb) of various organic compounds were achieved with a specific arrangement of bubbler and mass flow controllers (MFCs). During the sensor measurements, the net flow (air+VOC mix) into the test chamber was set to a constant value of 20 sccm. After the sensor devices were exposed to the organic compounds, they were allowed to regain their baseline current with the air-chemical mixture turned-off, without purging or evacuating the test-chamber.

Results

Figure 20:
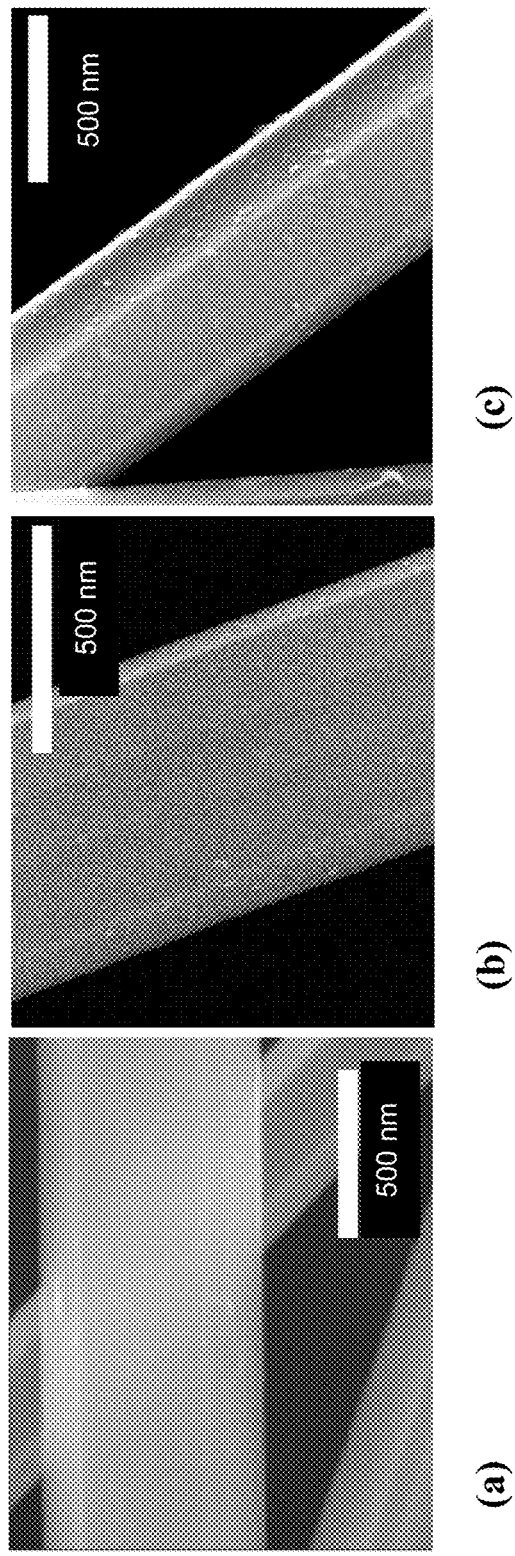
FIG. 20, plates (a-c), are field-emission scanning electron microscopy (FESEM) images of three different sputtered thickness of $TiO_2$ coatings: including 2 nm (plate (a)), 5 nm (plate (b)), and 8 nm (plate (c)) of $TiO_2$ sputtered on GaN nanowires.

FIG. 20 shows GaN nanowires with three different nominal thicknesses of $TiO_2$ coatings sputtered on them: 2 nm (FIG. 20, plate (a)); 5 nm (FIG. 20, plate (b)); and 8 nm (FIG. 20, plate (c)). Rather sparse, well-defined clusters can be seen for both the 5 nm and 8 nm area-averaged sputtered coatings of $TiO_2$. The average size of these large clusters was about 15 nm. For the 8 nm sputtered coating, the coverage of the $TiO_2$ clusters is much denser. However, TEM studies revealed the presence of clusters with much smaller diameter (less than about 4 nm) on the nanowire surface.

Figure 21:
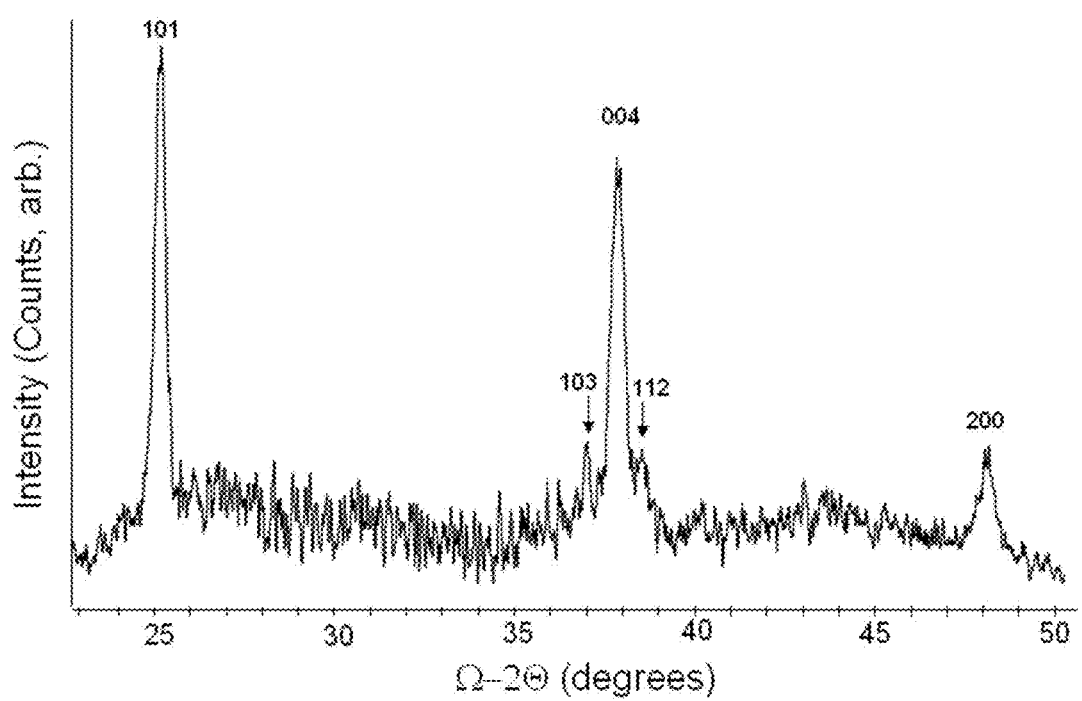
FIG. 21 illustrates graphically an XRD $\Omega$-2$\theta$ scan of 150 nm thick $TiO_2$ film deposited on $SiO_2$/Si substrate at 300° C. and annealed at 650° C. for 45 s in RTA. All indices correspond to the anatase phase [PDF#84-1285].

Detection of XRD signal from the $TiO_2$ decorated GaN NWs was difficult due to the minuscule size and total volume of $TiO_2$ nanoclusters. We therefore prepared a 150 nm thick $TiO_2$ film by sputtering it onto a $SiO_2$ coated Si substrate at 300° C. followed by anneal at 650° C. for 45 s in argon. The processing conditions produced an identical morphology as in the $TiO_2$ decorated NW case. Referring to FIG. 21, we identified from the XRD that $TiO_2$ is in the single-phase anatase form. As-deposited $TiO_2$ films were found to be amorphous.

The XRD results agree with the TEM analysis on $TiO_2$ decorated GaN NWs, which revealed that upon annealing at 700° C. for 30 s, the $TiO_2$ islands became partially crystalline, as shown in FIG. 22. Three most common phases of $TiO_2$ are anatase, rutile, and brookite. Thermodynamic calculations predict that rutile is the most stable $TiO_2$ phase in the bulk state at all temperatures and atmospheric pressure (see Norotsky A et al. (1967) "*Enthalpy of Transformation of a High-Pressure Polymorph of Titanium Dioxide to the Rutile Modification*," Science 158:338; Jamieson J C and Olinger B (1969) "*Pressure-temperature studies of anatase, brookite, rutile, and $TiO_2$ (II); A discussion*," Am. Min. 54:1477-1480). However, comparative experiments with particle size showed that the phase stability might reverse with decreasing particle size, possibly due to the influence of surface free energy and surface stress (Zhang H Z and Banfield J. F (2000) "*Understanding polymorphic phase transformation behavior during growth of nanocrystalline aggregates: insights from $TiO_2$*," J. Phys. Chem. B 104: 3481-3487). Anatase is the most stable phase when the particle size is less than about 11 nm, whereas rutile is most stable at sizes greater than about 35 nm. Although both rutile and anatase $TiO_2$ are commonly used as photocatalyst, anatase form shows greater photocatalytic activity for most reactions (Linsbigler A L et al. (1995) "*Photocatalysis on $TiO_2$ Surfaces: Principles, Mechanisms, and Selected Results*," Chem. Rev. 95:735-7; Tanaka K et al. (1991) "*Effect of crystallinity of $TiO_2$ on its photocatalytic action*," Chem. Phys. Lett. 187:73-76). This is one consideration for sputtering nominally 8 nm of $TiO_2$ for the sensor fabrication.

Although we have sputtered 8 nm of $TiO_2$ for fabricating the hybrid sensors, for the TEM studies 20 nm of $TiO_2$ coating was utilized. The thick GaN nanowires prevented acquisition of any TEM diffraction from thinner $TiO_2$ coatings. The TEM results presented for 20 nm thick $TiO_2$ was representative of the clusters formed for 8 nm deposited $TiO_2$ in actual sensors. Typical morphologies of a 20 nm thick $TiO_2$ film sputtered on n-GaN nanowires and annealed at 700° C. for 30 seconds are illustrated by TEM data in FIG. 22. The TEM image in FIG. 22, plate (a) shows 2 nm to 10 nm diameter individual $TiO_2$ particles non-uniformly distributed on the surface of a GaN nanowire. Some of the particles are identified by circles. Crystallinity of some nanoparticles observed is shown in the HRTEM image in FIG. 22, plate (b) with nanocrystallites on the edge of a GaN nanowire with the sputtered $TiO_2$. The FFT pattern from the boxed area is seen in exploded view in the upper left inset image, showing 0.35 nm lattice fringes which are consistent with a (101) reflecting plane of anatase but not available in hexagonal wurtzite-type GaN crystals.

Figure 23:
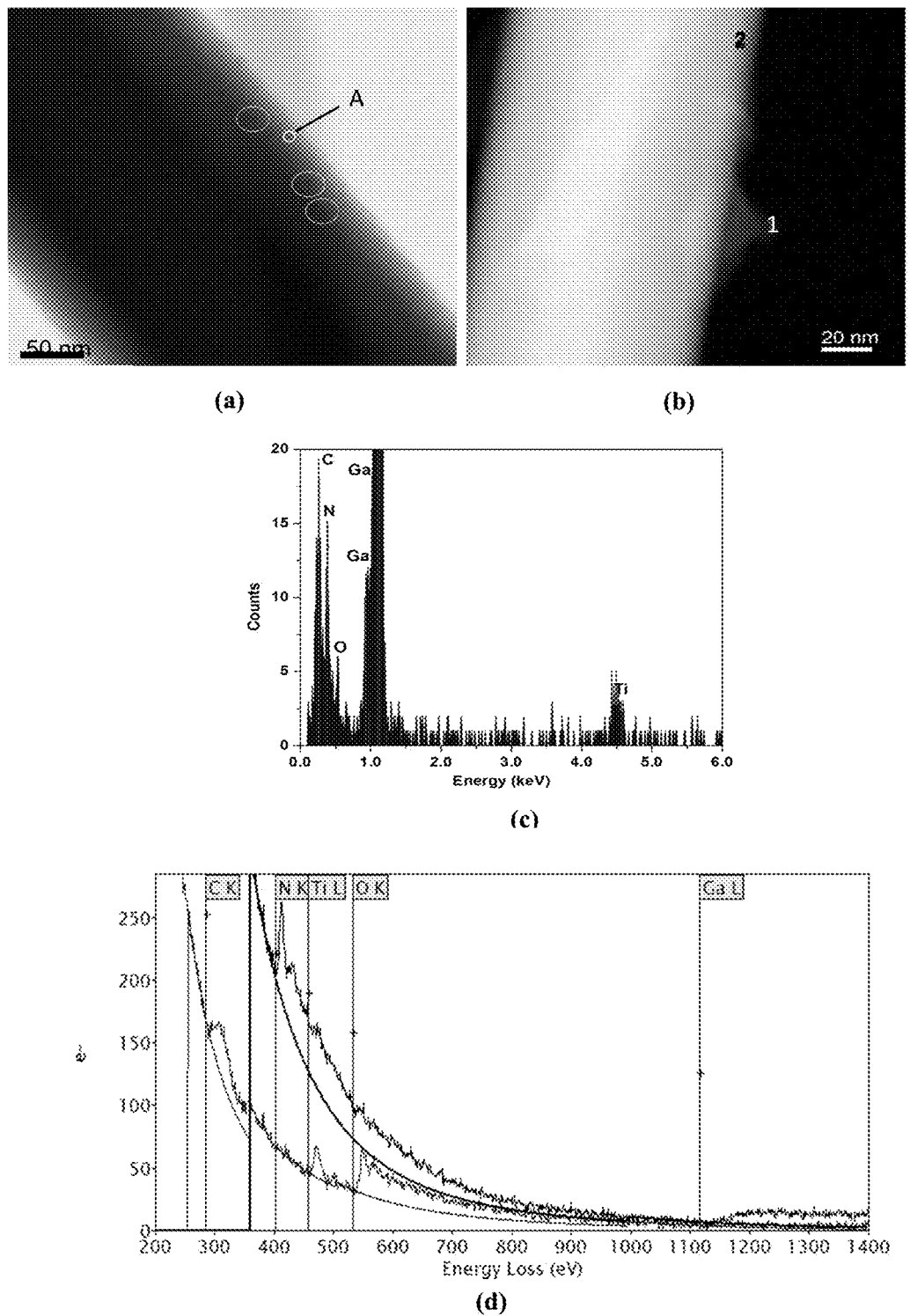
FIG. 23, plate (a) is a BF-STEM image with 5 nm to 10 nm $TiO_2$ nanoparticles barely visible near an edge of a GaN nanowire, with some of the nanoparticles marked by circles.

Referring to FIG. 23, plate (a), a BF-STEM image shows 5 to 10 nm $TiO_2$ nanoparticles barely visible against the GaN nanowire. An ADF-STEM image of a $TiO_2$ island on a GaN nanowire is shown in FIG. 23, plate (b). The presence of $TiO_2$ was confirmed by analysis of selected areas as well as of individual particles using XEDS and EELS and nanoprobe capabilities. Referring to FIG. 23, plate (c), the X-ray spectrum of an individual 5 nm $TiO_2$ particle (identified by the marked circle "A" in FIG. 23, plate (a)) exhibits the TiKα peak at 4.51 keV and the weak OKα peak at 0.523 keV. The NKα peak at 0.39 keV and gallium lines (the GaL series at 1.0 keV to 1.2 keV) and the CKα peak at 0.28 keV are also identified. EEL spectrum acquired at Position "1" marked in FIG. 23, plate (b) (the tip of a $TiO_2$-containing aggregate) exhibits the TiL edge at 456 eV and the OK edge at 532 eV and also the CK edge at 284 eV. A reference spectrum recorded at Position 2 marked in FIG. 23, plate (b) (an edge of the GaN nanowire) reveals traces of titanium and oxygen with the NK edge at 401 eV and the GaL edge at 1115 eV, respectively.

Figure 24:
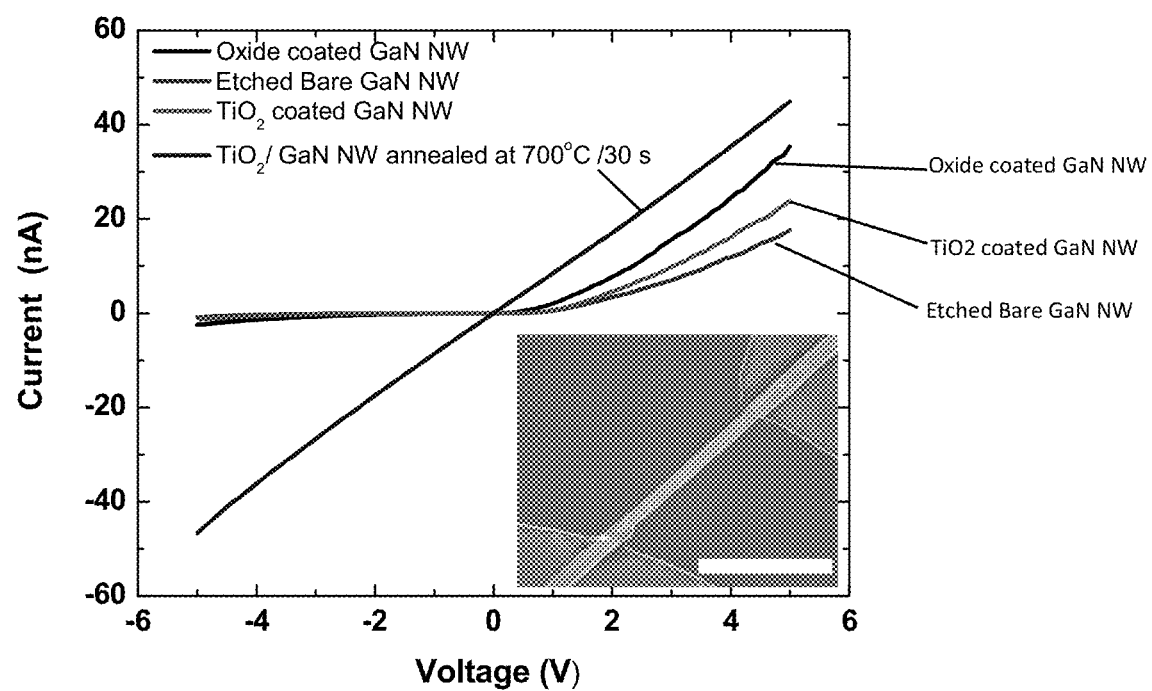
FIG. 24 illustrates I-V characteristics of a GaN NW two-terminal device in the dark at different stages of processing. The inset shows the nanowire device with length 5.35 µm and diameter 380 nm. The scale bar is 4 µm. The thickness of sputtered $TiO_2$ film was 8 nm.

FIG. 24 shows the current-voltage (I-V) characteristics of a GaN NW two-terminal device at different stages of processing. The I-V curves of the as-deposited devices were non-linear and asymmetric. The current decreased when the $SiO_2$ layer over the NW was etched. However, the current increased with the deposition of $TiO_2$ nanoclusters. Oxygen adsorption on the bare GaN nanowire surface can introduce surface states (Zywietz et al. (1999) "*The adsorption of oxygen at GaN surfaces*," Appl. Phys. Lett. 74:1695), resulting in the decrease of the nanowire conductivity. The devices annealed at 700° C. for 30 seconds showed significant changes in their I-V characteristics with a majority of the devices exhibiting linear I-V curves. This is consistent with the fact that low resistance ohmic contacts to the nitrides require annealing at 700° C. to 800° C. (see Motayed A et al. (2003) "*Electrical, thermal, and microstructural characteristics of Ti/Al/Ti/Au multilayer ohmic contacts to n-type GaN*," J. Appl. Phys. 93(2):1087-1094).

Figure 25:
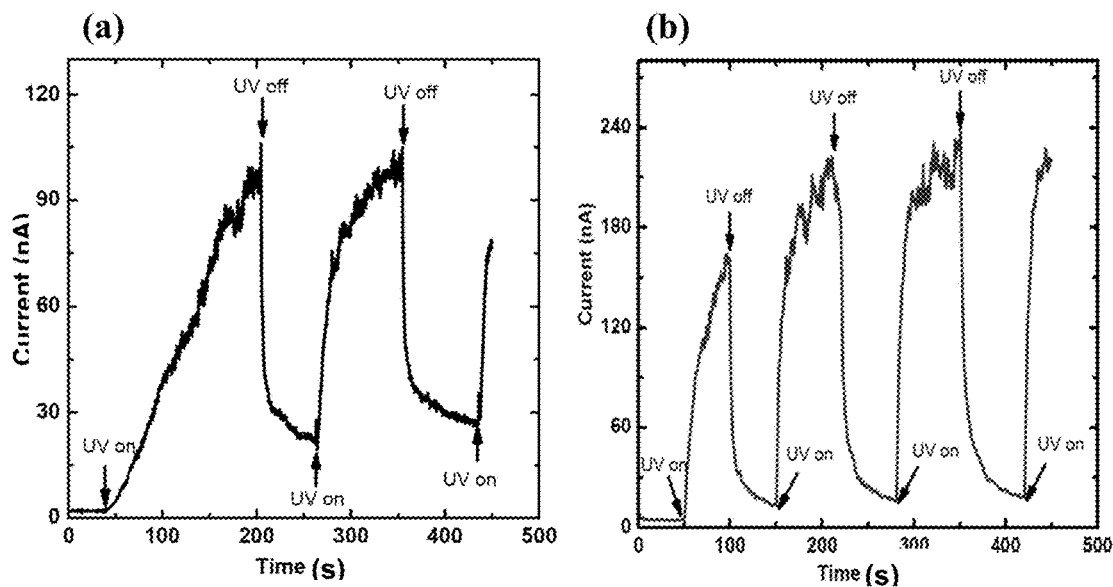
FIG. 25, plate (a) illustrates graphically the dynamic photocurrent of a bare GaN NW.

FIG. 25 shows the photoconductance of a bare GaN NW device and the $TiO_2$ coated GaN NW device. The NW devices with $TiO_2$ nanoclusters showed almost two orders of magnitude increase in the current when exposed to UV light as compared to the similar diameter bare NW devices. Increase of photoconductance due to surface functionalization has been observed in ZnO nanobelts coated with different polymers (Lao C S et al. (2007) "*Giant Enhancement in UV Response of ZnO Nanobelts by Polymer Surface-Functionalization*," J. Am. Chem. Soc. 129:12096-12097). This enhancement of photoconductance is often attributed to the separation of photogenerated charge carriers by a surface depletion field, thereby increasing the lifetime of the photogenerated carriers. After the light is turned off, the photo current decays rapidly, but not to the dark current value, which is likely due to the persistent photoconductivity of the NWs (see Sanford N A et al. (2010) "*Steady-state and transient photoconductivity in c-axis GaN nanowires grown by nitrogen-plasma-assisted molecular beam epitaxy*," J. Appl. Phy. 107:034318).

Figure 26:
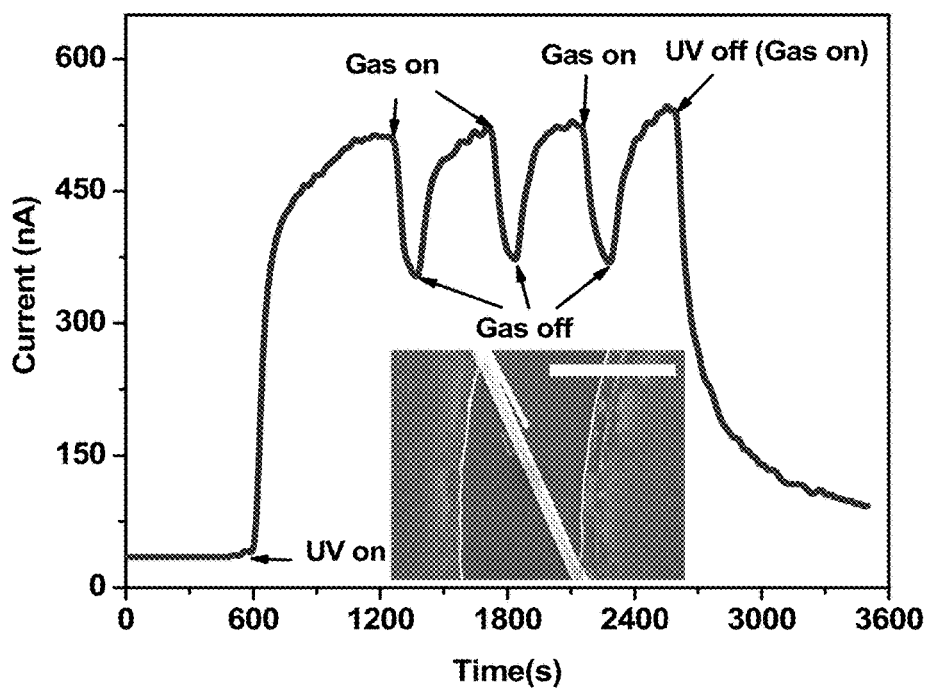
FIG. 26 illustrates graphically the dynamic response of a single GaN—$TiO_2$ hybrid device to 1000 ppm of toluene. For each cycle, the gas exposure time was 100 s. The inset shows the nanowire device with 8.0 µm length and diameter 500 nm. The scale bar is 5 µm.

The current through the bare GaN NW devices did not change when exposed to different VOCs mixed in air, even for concentrations as high as few percents. On the other hand, the $TiO_2$ coated hybrid devices responded even to the pulses of 20 sccm airflow. This is expected, considering that the conduction in most metal-oxides is affected by the presence of oxygen. The response of the $TiO_2$ nanocluster-GaN nanowire hybrid sensor to 1000 ppm of toluene in air is illustrated in FIG. 26. Exposure to the VOC in the dark had no effect on the hybrid device. However, in presence of UV excitation, when 1000 ppm of toluene (mixed in air) was introduced into the gas chamber, the sensor photocurrent decreased dramatically to approximately ⅔ of its base value. After 100 seconds of gas exposure, the gas flow is turned off and the sensor is allowed to recover at room temperature without any additional purging. The repeatability of the sensing action of these hybrid sensors is evident from FIG. 26.

Figure 27:
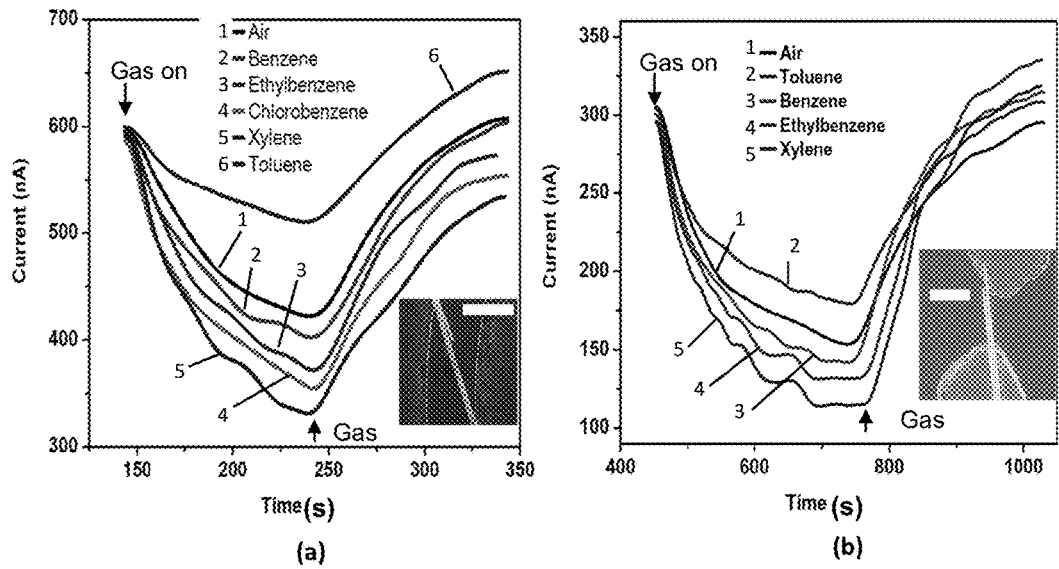
FIG. 27, plate (a) illustrates the response of a single nanowire-nanocluster hybrid sensor (inset shows nanowire with diameter 500 nm) to 1000 ppm benzene, toluene, ethylbenzene, chlorobenzene, and xylene in presence of UV excitation.

Interestingly, the hybrid sensors did not respond when exposed to methanol, ethanol, isopropanol, chloroform, acetone, and 1,3-hexadiene, even for concentrations as high as several percent. Also, the photocurrent for these sensors increased with respect to air when exposed to toluene vapors, whereas for every other aromatic compound, the photocurrent decreased relative to air, as shown in FIG. 27, plate (a). More than twenty sensor devices were tested, with all exhibiting the same trend. In addition, the use of toluene from different sources resulting in the same sensor behavior. FIG. 27, plate (b) shows the response of a different device for 200 ppb concentrations of the same chemicals. It is clear that even for toluene concentration as low as 200 ppb, the relative change in photocurrent is the reverse of that observed with other chemicals. If the photocurrent in the presence of air for these sensors is used as their baseline calibration, then we can distinctly identify toluene from other aromatic compounds present in air using our hybrid devices. The response time is defined as the time taken by the sensor current to reach 90% of the response ($I_f$-$I_0$) when exposed to the analyte. The $I_f$ is the steady sensor current level in the presence of the analyte, and $I_0$ is the current level without the analyte, which in our case is in the presence of air. The recovery time is the time required for the sensor current to recover to 30% of the response ($I_f$-$I_0$) after the gas flow is turned off (Garzella C et al. (2000) "*$TiO_2$ thin films by a novel sol-gel processing for gas sensor applications*,"

Sens. and Actuators B: Chemical 68:189-196). The response and recovery times for ppm levels of BTEX concentrations were ≈60 seconds and ≈75 seconds, respectively. The response and recovery times for ppb levels of concentrations were ≈180 seconds and ≈150 seconds, respectively. In contrast, conventional nanowire/nanotube sensors reported in the literature as working at room-temperatures had much longer response times in minutes (Leghrib R et al. (2010) "*Gas sensors based on multiwall carbon nanotubes decorated with tin oxide nanoclusters*," Sens. and Actuators B: Chemical 145:411-416; Balazsi C et al. (2008) "*Novel hexagonal $WO_3$ nanopowder with metal decorated carbon nanotubes as $NO_2$ gas sensor*," Sensors and Actuators B: Chemical 133:151-155; Kuang Q et al. (2008) "*Enhancing the photon-and gas-sensing properties of a single $SnO_2$ nanowire based nanodevice by nanoparticle surface functionalization*," J. Phys. Chem. C 112:11539-11544; Lim W et al. (2008) "*Room temperature hydrogen detection using Pd-coated GaN nanowires*," Appl. Phys. Lett. 93:072109). Fast response and recovery times indicate fast adsorption and desorption, which is attributed to the enhanced reactivity of the nanoscale $TiO_2$ clusters.

Figure 28:
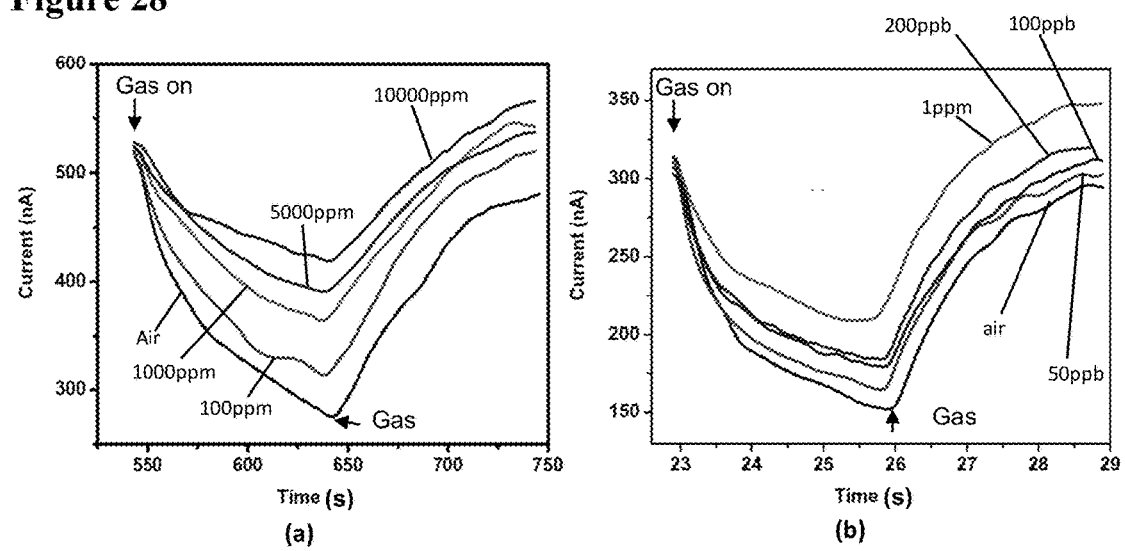
FIG. 28 illustrates graphically a hybrid sensor's photoresponse characteristics.

The responses of two hybrid devices to different concentrations of toluene in air are shown in FIG. 28. FIG. 28, plate (a) shows the change of photocurrent of a 234 nm diameter device when exposed to toluene concentrations from 10000 ppm down to 100 ppm. FIG. 28, plate (b) shows the photocurrent of a sensor device with 170 nm diameter wire for toluene concentrations from 1 ppm to 50 ppb.

Figure 29:
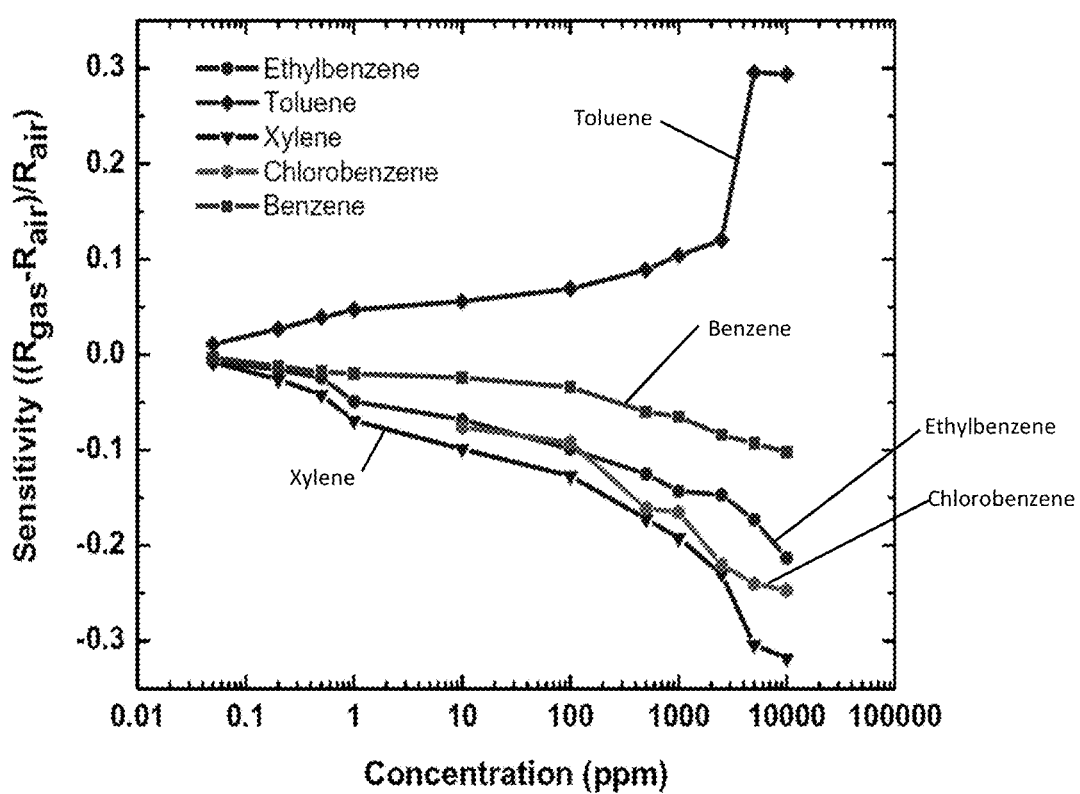
FIG. 29 illustrates sensitivity plots of a GaN—$TiO_2$ nanowire-nanocluster hybrid device (diameter 300 nm) for benzene, toluene, ethylbenzene, chlorobenzene, and xylene. The plot identifies the sensor's ability to measure wide range of concentration of the indicated chemicals.

Sensitivity is defined as $(R_{gas}-R_{air})/R_{air}$, where $R_{gas}$, $R_{air}$ are the resistances of the sensor in the presence of the chemical-air mixture and in the presence of air, respectively. The sensitivity plots of a hybrid device for different VOCs tested are shown in FIG. 29. The sensitivity plot emphasizes the ability of these hybrid sensors to reliably detect BTEX (benzene, toluene, ethylbenzene, chlorobenzene, and xylene), which are common indoor and outdoor pollutants with wide detection range (50 ppb to 1%).

Example 2

The sensing behavior of three NWNC based hybrid sensors was compared: 1) GaN NW coated with $TiO_2$ NCs (hereafter referred to as GaN/$TiO_2$ NWNC hybrids); 2) GaN NW coated with $TiO_2$ and Pt multicomponent NCs (i.e., GaN/($TiO_2$—Pt) NWNC hybrids); and 3) GaN NW coated with Pt NCs (i.e., GaN/Pt NWNC hybrids). It was found that sensors with $TiO_2$—Pt multicomponent NCs on GaN NW were only sensitive to methanol, ethanol, and hydrogen. Higher carbon-containing alcohols (such as n-propanol, iso-propanol, n-butanol) did not produce any sensor response. These sensors had the highest sensitivity towards hydrogen. Prior to the Pt deposition, the GaN/$TiO_2$ NWNC hybrids did not exhibit any response to alcohols, however they detected benzene and related aromatic compounds such as toluene, ethylbenzene, xylene, and chlorobenzene mixed with air. The GaN/Pt hybrids only showed sensitivity to hydrogen and not to methanol or ethanol. The sensitivity of GaN/Pt hybrids towards hydrogen was lower compared to the GaN/($TiO_2$—Pt) hybrids.

Materials and Methods

GaN NWs utilized for this study were c-axis, n-type (Si-doped), grown by catalyst-free molecular beam epitaxy as described by Bertness K A et al. (2008), supra, J. Crystal Growth 310(13):3154-3158. Post-growth device fabrication was done by dielectrophoretically aligning the nanowires on 9 mm×9 mm sapphire substrates. The details of the device fabrication are set forth in Example 1. After fabrication of two-terminal GaN NW devices, the $TiO_2$ NCs were deposited on the GaN NW surface using RF magnetron sputtering. The deposition was done at 325° C. with 50 standard cubic centimeters per minute (sccm) of Ar flow, and 300 W RF power. The nominal deposition rate was about 0.24 Å/s. Thermal annealing of the complete sensor devices (GaN NW with $TiO_2$ nanoclusters) was done at 700° C. for 30 seconds in a rapid thermal processing system. For $TiO_2$—Pt composite NCs, the Pt was sputtered using DC sputtering after annealing of the $TiO_2$ clusters on GaN NW. The Pt sputtering was done with an Ar flow of 35 sccm, at a pressure of 1.3 Pa and power of 40 W for 10 seconds. For the Pt/GaN devices Pt was sputtered on bare GaN NWs after annealing the ohmic contacts at 700° C. for 30 seconds. Additional lithography was performed to form thick metal bond pads with Ti (40 nm) and Au (200 nm). The device substrates, i.e., the sensor chips, were wire-bonded on a 24 pin ceramic package for the gas sensing measurements.

The microstructure and morphology of the sputtered $TiO_2$ films used for the fabrication of the sensors were characterized by high-resolution transmission and scanning transmission electron microscopy (HRTEM/STEM), selected-area electron diffraction (SAED), and field-emission scanning electron microscopy (FESEM). For the TEM characterization, the GaN NWs were dispersed on 10 nm thick carbon films supported by Mo-mesh grids, followed by the deposition of $TiO_2$ NCs and annealing, and subsequent Pt deposition. The samples were analyzed in a FEI Titan 80-300 TEM/STEM microscope operating at 300 kV accelerating voltage and equipped with S-TWIN objective lenses, which provided 0.13 nm (STEM) and 0.19 nm (TEM) resolution by points. The instrument also had a Gatan CCD image acquisition camera, bright-field (BF), ADF and high-angle annular dark-field (HAADF) STEM detectors to perform spot, line profile, and areal compositional analyses using an EDAX 300 kV high-performance Si/Li X-ray energy dispersive spectrometer (XEDS).

The as-fabricated sensors were placed in a custom designed gas chamber for gas exposure measurements. The device characterization and the time dependent sensing measurements were done using an Agilent B1500A semiconductor parameter analyzer. The gas sensing experiments have been performed by measuring the electrical conductance of the devices upon exposure to controlled flow of air/chemical mixture in presence of UV excitation (25 W deuterium bulb operating in the 215 nm to 400 nm range). For all the sensing experiments with chemicals, breathing air (<9 µmol/mol of water) was used as the carrier gas. For the hydrogen sensing we used high-purity nitrogen as the carrier gas. After the sensor devices were exposed to the organic compounds and hydrogen, they were allowed to regain their baseline current with the air-chemical mixture turned-off, without purging or evacuating the test-chamber.

Results

Morphological and Structural Characterization of NWNC Hybrids

It was challenging to measure the sizes and shapes of small $TiO_2$ and Pt particles on the surfaces GaN NWs from greyscale TEM images due to: a) 270 nm to 300 nm thickness of the NWs used in the devices and variations of thickness and curvature across the structure; b) diffraction contrast induced particularly by bending of the wires—even similar particles could appear as having different intensities, while local thickness variations of the carbon support film could result in variable contrast affecting the mean intensity values of the particles; c) overwhelming domination of electron diffraction in SAED from the GaN NW over the diffraction from $TiO_2$ and Pt nanoparticles. To overcome these problems, TEM imaging was conducted under minimal beam intensity conditions close to the Scherzer defocus at highest available accelerating voltage of 300 kV using both stationary beam (bright-field TEM/SAED, phase-contrast high-resolution TEM) and scanning beam (STEM/XEDS) modes. Areas for analyses were selected near the wire's edges and on the amorphous carbon support film in the vicinity of the NWs.

FIG. 30 shows HRTEM micrographs of a GaN NW on a thin amorphous carbon support films with $TiO_2$ coating, before and after the Pt deposition. The deposited $TiO_2$ layer formed an island-like film, where 10 nm to 50 nm partially aggregated particles (see FIG. 30, plate (a)) were often interconnected into extended two-dimensional networks. This was consistent with SAED and compositional analyses of deposited $TiO_2$ films indicating a mixture of polycrystalline anatase and rutile and of the same mixture plus fcc Pt nanoparticles (FIG. 30, plate (b)), respectively. Pt crystalline particles with 1 to 5 nm size were randomly distributed on the surfaces of $TiO_2$ islands and sometimes were partially coalesced forming elongated aggregates. In the latter case, significant thickness of the GaN NWs made it difficult to visualize $TiO_2$ deposits due to the limited contrast difference between $TiO_2$ and GaN and presence of multiple heavy Pt particles. In spite of these limitations, detailed HRTEM and HR-STEM observations revealed 0.35 nm (101) hcp lattice fringes belonging to anatase (see FIG. 30, plate (b), upper left inset) and 0.23 nm to 0.25 nm (111) and 0.20 nm to 0.22 nm (200) fcc lattice fringes belonging to Pt nanocrystallites, respectively, as well as amorphous-like Pt clusters with diameters around 1 nm or less (see FIG. 31, plates (a) and (b)).

In the FIG. 31, HAADF-STEM image shows 1 nm to 5 nm diameter bright Pt nanoparticles and barely visible $TiO_2$ islands (medium grey) randomly distributed near the edge of the nanowire. The presence of both $TiO_2$ and Pt nanocrystallites was confirmed by the analysis of selected areas using XEDS nanoprobe capabilities.

Current-Voltage (I-V) Characteristics of NWNC Hybrids in Dark

Figure 32:
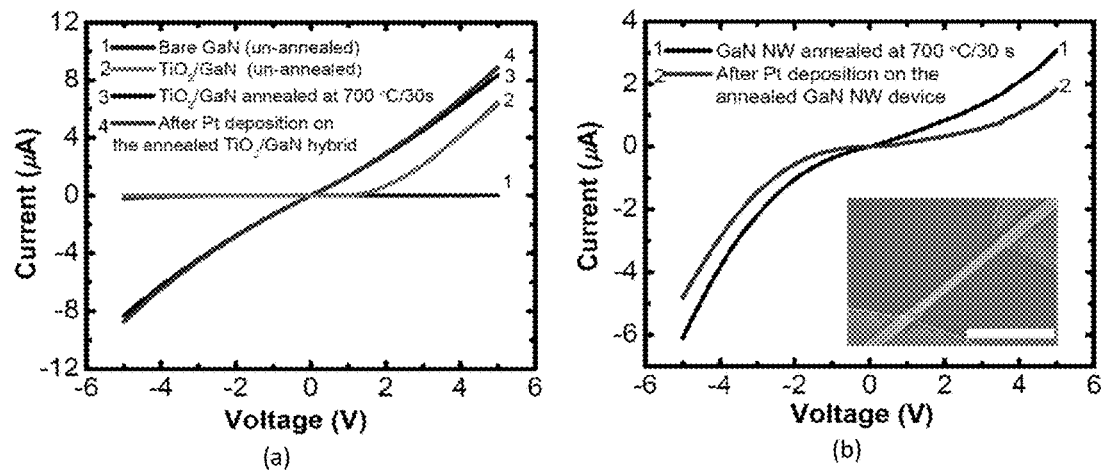
FIG. 32 illustrates I-V characteristics of the hybrid sensor device at different stages of processing.

FIG. 32 shows the I-V characteristics of the GaN/($TiO_2$—Pt) and GaN/Pt hybrid sensor devices at different stages of processing. A plan-view SEM image of an exemplary sensor device is shown in the inset of FIG. 32, plate (b) for representation purposes. The I-V curves of the as-fabricated GaN NW two-terminal devices were non-linear and asymmetric. A small increase in the positive current after the deposition of $TiO_2$ nanoclusters (curve 2) can be attributed to decreased surface depletion of the GaN NW due to passivation of surface states, and/or the high temperature deposition (325° C.) of the nanoclusters initiating ohmic contact formation. The devices annealed at 700° C. for 30 s after the deposition of $TiO_2$ NCs showed significant change in their I-V characteristics with a majority of the devices exhibiting linear I-V curves. Interestingly, Pt NC deposition on $TiO_2$ coated GaN NWs further increased the conductivity of the nanowire. This is due to the fact that the Pt clusters depleted the $TiO_2$ clusters by removing free electrons. Increased depletion in the $TiO_2$ clusters due to Pt would decrease $TiO_2$ induced depletion in the GaN NW, leading to an increase in the NW current. With the Pt/GaN hybrids, the current decreases followed by the deposition of Pt (see FIG. 32, plate (b)) as expected due to the depletion region formed in the NW under the metal clusters.

Figure 33:
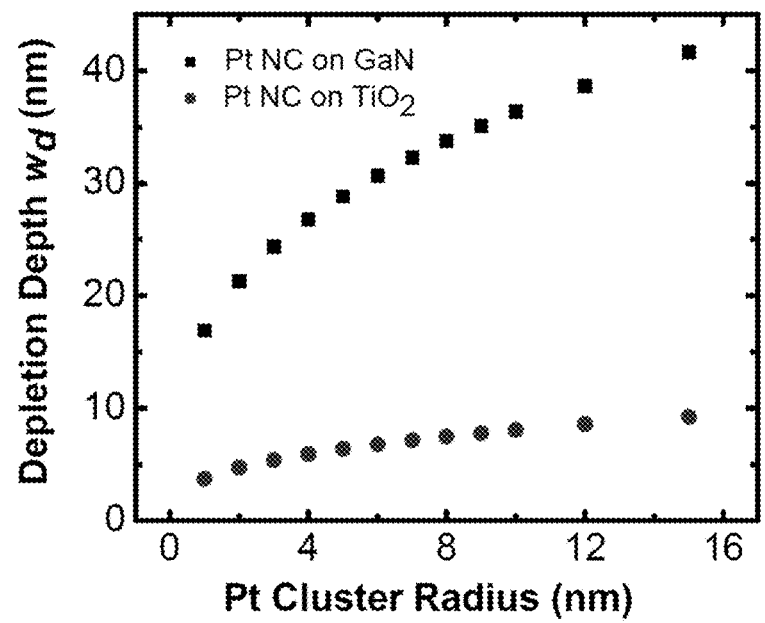
FIG. 33 illustrates graphically depletion depth induced by Pt NCs on GaN and $TiO_2$ as calculated by equation 12.

The nature of the depletion region formed by the nano-sized metal clusters on a semiconductor may be determined by Zhdanov's model. FIG. 33 shows the calculated zero-bias depletion depth produced in GaN and $TiO_2$ respectively, as a function of the Pt cluster radius according to Equation (1). For calculating the depletion depth we assumed the effective conduction band density of states in $TiO_2$ as $3.0 \times 10^{21}$ cm$^{-3}$ and point-defect related donor concentration as $1.0 \times 10^{18}$ cm$^{-3}$ [43,44]. The electron concentration in the GaN NWs was measured to be $1 \times 10^{17}$ cm$^{-3}$ in a separate experiment.

FIG. 33 indicates that even a single Pt NC of 2 nm radius can significantly deplete a 10 nm (average size) $TiO_2$ cluster. The effect of $TiO_2$ depletion on GaN NW is difficult to determine as it could be influenced by numerous factors including interface states and particle geometry. Given the very high density of $TiO_2$ clusters on the NW surface (see FIG. 31, plate (b)), it is clear that the Pt particles mostly reside on the surfaces of $TiO_2$ NCs. However, from FIG. 33 we can see that when Pt NCs are directly on GaN, they deplete the carriers in an even larger region in the GaN NW. This qualitatively explains the relatively larger change in current observed when Pt NCs were deposited on bare GaN NWs as compared to the change in current when Pt NC were deposit on the $TiO_2$-coated NWs.

Comparative Sensing Behavior of GaN/($TiO_2$—Pt), GaN/Pt and GaN/$TiO_2$ NWNC Hybrid Sensors The photocurrent through the bare GaN NW devices did not change when exposed to different chemicals mixed in air, even for concentrations as high as 3%. In contrast, the $TiO_2$-coated hybrid devices responded even to the pulses of 20 sccm airflow in the presence of UV excitation. The response of the $TiO_2$ NC-coated GaN nanowire hybrid sensors to different concentrations of benzene, toluene, ethylbenzene, chlorobenzene, and xylene in air is discussed above. The GaN/$TiO_2$ hybrids showed no response when exposed to other chemicals such as alcohols, ketones, amides, alkanes, nitro/halo-alkanes, and esters.

Remarkably, after the deposition of Pt nanoclusters on the GaN/$TiO_2$ hybrids, the sensors were no longer sensitive to benzene and other aromatic compounds, but responded only to hydrogen, methanol, and ethanol. In addition, the GaN/($TiO_2$—Pt) hybrids showed no response when exposed to higher carbon-containing (C>2) alcohols such as n-propanol, iso-propanol, and n-butanol. FIG. 5 shows the change of photocurrent of a GaN/($TiO_2$—Pt) sensor in the presence of 20 sccm air flow of air mixed with 1000 µmol/mol (ppm) of methanol, ethanol, and water, respectively, and 20 sccm of nitrogen flow mixed with 1000 µmol/mol (ppm) hydrogen. The change in the photocurrent of the sensor when 20 sccm of breathing air is flowing through the test chamber serves as a reference for calculating the sensitivity of the sensors. The sensitivity is defined as $(R_{gas}-R_{air})/R_{air}$, where $R_{gas}$ and $R_{air}$ are the resistances of the sensor in the presence of the analyte-air mixture and in the presence of air only, respectively ($R_{air}$ is replaced with $R_{nitrogen}$ for hydrogen sensing experiments).

Figure 34:
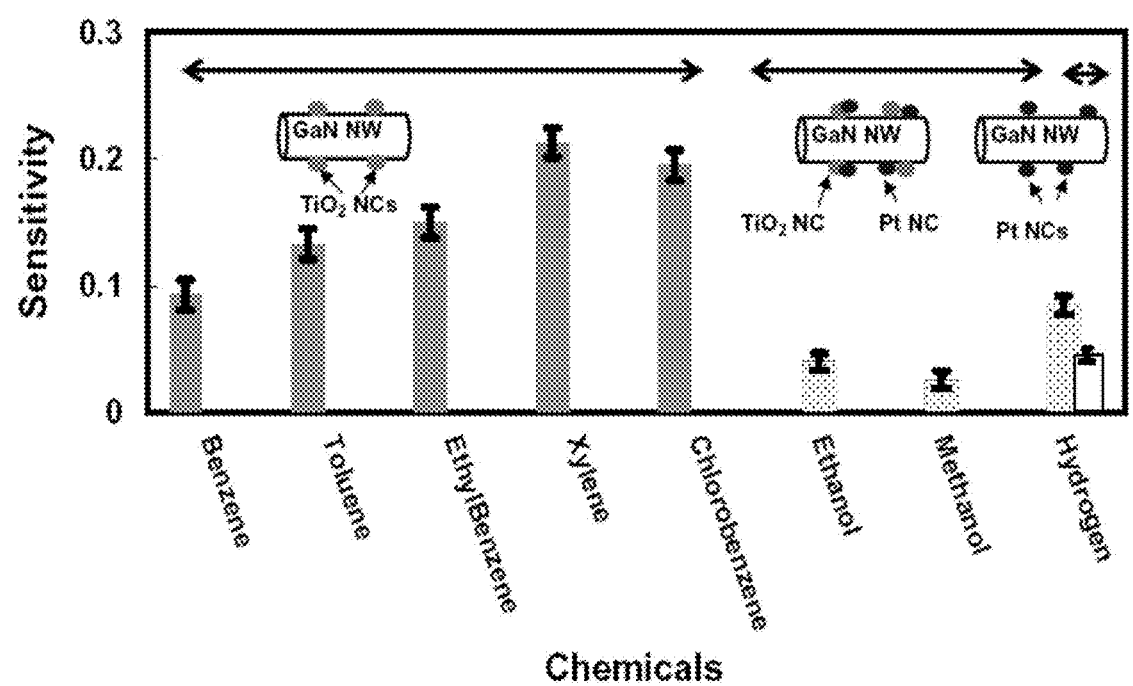
FIG. 34 illustrates comparative sensing behavior of the three hybrids for 1000 µmol/mol (ppm) of analyte in air: light gray bar graphs (benzene, toluene, ethylbenzene, xylene, chlorobenzene) represent GaN/$TiO_2$ hybrids, patterned bar graphs (ethanol, methanol, and hydrogen) represent GaN/($TiO_2$—Pt) hybrids, and white bar graph (hydrogen) represents GaN/Pt hybrids. Other chemicals which did not produce any response in any one of the hybrids are not included in the plot. The zero line is the baseline response to 20 sccm of air and $N_2$. For this plot the magnitude of the sensitivity is used. The error bars represent the standard deviation of the mean sensitivity values for every chemical computed for 5 devices with diameters in the range of 200 nm-300 nm.

The GaN/$TiO_2$ hybrids without Pt showed no response to hydrogen and the alcohols. Interestingly, when Pt NC-coated GaN NW hybrids (GaN/Pt) with the same nominal thickness were tested, they showed very limited sensitivity only to hydrogen and not to any alcohols. The comparative summary of the sensing behavior of the three different hybrids are presented in FIG. 34.

The response of the GaN/($TiO_2$—Pt) NWNC sensor to different concentrations of methanol in air is shown in FIG. 35, plate (a). FIG. 35, plate (b) shows the response to different concentrations of hydrogen in nitrogen for the same GaN/(TiO$_2$—Pt) NWNC sensor device. The sensor response is much higher for hydrogen compared to methanol and ethanol. The response time is also much shorter for hydrogen as compared to methanol, and the sensor photocurrent saturates after initial 20 s exposure.

The response time was defined as the time taken by the sensor current to reach 90% of the response (I$_f$-I$_0$) when exposed to the analyte. The I$_f$ is the steady sensor current level in the presence of the analyte, and I$_0$ is the current level without the analyte, which in our case is in the presence of 20 sccm of air flow. The recovery time is the time required for the sensor current to recover to 30% of the response (I$_f$-I$_0$) after the gas flow is turned off (see Garzella C et al. (2000) Sensors and Actuators B: Chemical 68:189-196). The response time for hydrogen was ≈60 seconds, whereas the response time for ethanol and methanol was ≈80 seconds. The sensor recovery time for hydrogen was ≈45 seconds and the recovery times for ethanol, methanol was ≈60 seconds and ≈80 seconds, respectively. For comparison, Wang et al. demonstrated a conventional ZnO NW-based hydrogen sensor with a response time of 10 minutes for 4.2% sensitivity (Wang H T et al. (2005) "Hydrogen-selective sensing at room temperature with ZnO nanorods," Appl. Phys. Lett. 86:243503).

The sensitivity plot of a GaN/(TiO$_2$—Pt) hybrid device for the various analytes tested is shown in FIG. 36, plate (a). Note that the lowest concentration detected for methanol and hydrogen (1 ppm or μmol/mol) is not the sensor's detection limit, but a system limitation. It can be seen that the sensor is more sensitive to methanol than ethanol for concentrations ≥1000 μmol/mol (ppm), and the relative sensitivity switches for concentrations of 500 μmol/mol (ppm) and below. Similar behavior is observed with twenty unique devices, possibly due to difference in surface coverage of the different alcohols over the concentration range. FIG. 36, plate (b) is a comparative plot showing the sensitivity of GaN/(TiO$_2$—Pt) and GaN/Pt hybrid sensors to hydrogen in nitrogen. The GaN/Pt hybrid devices showed relatively low sensitivity with detection limit of 50 μmol/mol (ppm), below which the devices stopped responding. The gas exposure time was also increased to 200 seconds for the GaN/Pt devices to obtain increased response compared to 100 seconds for the GaN/(TiO$_2$—Pt) GaN devices. The sensitivity of the GaN/(TiO$_2$—Pt) sensors was greater for alcohols and hydrogen when compared with the same concentrations of water in air, which thus enables their use in high-humidity conditions.

Table X and Table XI compare the performance of the sensor devices of the present invention with sensors disclosed in the most recent literature in terms of operation temperature, carrier gas, lower detection limit, and response/recovery times. The comparison indicates that the sensors devices of the present invention exhibit an excellent response to very low concentrations of analytes (100 ppb for ethanol and 1 ppm for hydrogen) at room temperature, with air as the carrier gas. The testing conditions closely resembled real-life conditions, which underlines the significance of the disclosed sensors. The response and recovery times were also lower for the disclosed sensors compared to the other conventional sensors, as shown in Tables X and XI.

TABLE X

Performance of GaN/(TiO$_2$—Pt) NWNC hybrid sensors to ethanol in comparison with conventional sensors

|  | Response/Recovery Time | Lower Detection Limit | Carrier Gas | Testing Temperature |
|---|---|---|---|---|
| Sensor of Present Invention | 80 s/75 s | 100 ppb with 1% sensitivity[4] | air | Room temperature (RT) |
| CNT[1]/SnO$_2$ core shell nanostructures | 1 s/10 s | 10 ppm | air | 300° C. |
| MWCNTs[2]/NaClO$_4$/polypyrrole | 20 s/20 s | 18,000 ppm | air | RT |
| Metal-CNT hybrids | ~2 min/ (recovery time not reported) | 500 ppb with sensitivity <1% | N$_2$ in a vacuum test chamber | RT |
| V$_2$O$_5$ nanobelts | 50 s/50 s | 5 ppm | air | 150° C.-400° C. |
| ZnO nanorods | 3.95 min/5.3 min | 10 ppm | Synthetic air | 125° C.-300° C. |
| ZnO nanowires | 10 s/55 s | 1 ppm | air | 220° C. |
| ITO[3] nanowires | 2 s/2 s | 10 ppm | air | 400° C. |
| SnO$_2$ nanowires | 2 s/2 s | 10 ppm | air | 300° C. |

[1]Carbon nanotubes
[2]Multiwall carbon nanotubes
[3]Indium tin oxide
[4]Sensitivity values for sensors with lowest limit similar to disclosed results were compared.

TABLE XI

Performance of GaN/(TiO$_2$—Pt) NWNC hybrid sensors to hydrogen in comparison with conventional sensors

|  | Response/recovery times | Lower detection limit | Testing Temperature |
|---|---|---|---|
| Sensor of Present Invention | 60 s/45 s | 1 ppm with sensitivity of 4% | RT |
| CNT films | 5 min/30 s | 10 ppm | RT |
| SWCNT/SnO$_2$ | 2 s/2 s | 300 ppm | 250° C. |
| Pd/CNTs | 5 min/5 min | 30 ppm with sensitivity of 3% | RT |

TABLE XI-continued

Performance of GaN/(TiO$_2$—Pt) NWNC hybrid sensors to hydrogen in comparison with conventional sensors

| | Response/recovery times | Lower detection limit | Testing Temperature |
|---|---|---|---|
| Pd/Si NWs | 1 hr/50 min | 3 ppm | RT |
| Pt doped SnO$_2$ NWs | 2 min/10 min | 100 ppm | 100° C. |

The present results indicate the unique ability to tailor the selectivity of NWNC chemical sensors. With infinite combinations of metal and metal-oxide composite clusters available, there is a huge potential for sensor designs targeted for a multitude of applications.

Example 3

Alcohol sensors using gallium nitride (GaN) nanowires (NWs) functionalized with zinc oxide (ZnO) nanoparticles are demonstrated. These sensors operate at room temperature, are fully recoverable, and demonstrate a response and recovery time on the order of 100 seconds. The sensing is assisted by UV light within the 215-400-nm band and with the intensity of 375 nW/cm$^2$ measured at 365 nm. The ability to functionalize an inactive NW surface, with analyte-specific active metal-oxide nanoparticles, makes this sensor suitable for fabricating multianalyte sensor arrays.

Methods and Materials

Si-doped c-axis n-type GaN NWs were grown using catalyst-free molecular beam epitaxy on Si (III) substrate as described in Bertness K A et al. (2008), supra, *J. Cryst. Growth* 310(13):3154-3158. The NW diameter and length were in the ranges of 250-350 nm and 21-23 μm, respectively. The GaN NWs were detached from the substrate by sonication in isopropanol and dielectrophoretically aligned across the pre-patterned electrodes. The electrodes were fabricated using photolithography followed by deposition of a metal stack of Ti (40 nm)/Al (420 nm)/Ti (40 nm). Thick bottom electrodes ensure the free suspension of the NWs. For the formation of ohmic contacts to the NW ends, the top metal contacts were fabricated using a metal stack of Ti (70 nm)/Al (70 nm)/Ti (40 nm)/Au (40 nm), as described in A. Motayed et al. (2003), supra, *J. Appl. Phys.* 93(2):1087-1094. Rapid thermal anneal (RTA) was performed at 700° C. for 30 seconds in argon atmosphere to promote the formation of ohmic contacts and to reduce the stress in the thick bottom electrodes. Finally, ZnO nanoparticles were sputter deposited on the NW device with an RF power of 300 W in 60 standard cubic centimeters per minute (sccm) of oxygen and 40 sccm of argon gas flow at room temperature. Deposition time of 160 seconds was found to be optimal for the formation of uncoalesced oxide nanoparticles.

The microstructure of the devices was characterized using a scanning electron microscope (SEM) and X-ray diffraction (XRD). Due to the small size of the nanoparticles, the XRD signal from ZnO was not detected. Thus, the analysis was performed on a 300-nm-thick ZnO film sputter deposited on Si (111) substrate with the assumption that the ZnO crystallinity is similar for nanoparticles and for thin films deposited at the identical conditions. Current-voltage characteristics of the devices were also measured to determine the nature of the NW-metal contacts.

For the gas sensing measurements, a device was placed inside the stainless steel chamber with an inlet and an outlet for the analyte vapors. The chamber, with a volume of 0.73 cm$^3$, has a quartz window on the top to facilitate exposure of the device to UV light. The wavelength of the light bulb was confined to the range of 215-400 nm; the intensity recorded at 365 nm was 3.75 nW/cm$^2$. The sensor baseline was established at a constant flow of 40 sccm of breathing air under illumination. For sensing experiments, 40 sccm of the mixture of the breathing air and analyte vapor was passed through the chamber. All sensing measurements were performed in the presence of UV light and 5-V dc voltage bias applied across the device terminals. Negligible or no chemiresistive response was observed for all the chemicals in the absence of the illumination.

Results and Properties

FIG. 6, plate (a) shows a SEM image of a device with a single GaN NW suspended across the metal electrodes. FIG. 6, plate (b) shows the ZnO nanoparticles on the facets of a GaN NW. The current-voltage characteristics of the device measured before and after RTA are shown in FIG. 6, plate (c). As shown in FIG. 6, plate (d), XRD reveals that the sputter-deposited ZnO is crystalline and highly (0002) textured.

Referring to FIG. 8 sensor response to air and nitrogen was evaluated. FIG. 8, plate (a) shows the device response to the different flow rates of breathing air. As seen therein, device conductance decreases upon exposure to the breathing air, and the decrease is proportional to the flow rate. Opposite behavior (i.e., an increase in conductivity) is observed when the device is exposed to nitrogen gas as seen in FIG. 8, plate (b).

Referring to FIG. 7, sensor response to alcohols and other analytes was evaluated. When exposed to alcohol vapors (methanol, ethanol, n-propanol, isopropanol, n-butanol, and isobutanol), the devices showed an increase in conductivity with maximum sensitivity toward methanol. FIG. 7 shows the device response to 500-μmol/mol (ppm) methanol vapor in breathing air.

For the isomers of an alcohol, the sensitivity decreases with branching in the carbon chain. Hence, as shown in FIG. 7 (inset, bottom left), the sensitivity toward isobutanol is less than that toward n-butanol. As shown in FIG. 7 (inset, bottom right), the devices show a negligible response to possible interfering chemicals such as benzene and hexane, whereas the sensitivity toward 100 μmol/mol (ppm) of ethanol is similar to the sensitivity toward 1000 μmol/mol (ppm) of acetone. Ethanol vapor concentration down to 100 nmol/mol (ppb) was successfully detected, and the detection of even lower concentrations is possible with alternative measurement setup.

Example 4

A hybrid chemiresistive architecture, utilizing nanoengineered wide-bandgap semiconductor backbone functionalized with multicomponent photocatalytic nanoclusters of metal-oxides and metals was demonstrated. These sensors operated at room-temperature via photoenabled sensing.

Etching of Semiconductor Nanostructures

For real-time nanosensors, successful etching of semiconducting nanostructures, which is characterized by smooth surfaces with minimal sub-surface damage and appropriate side-wall profiles, is desired. This requires overcoming the strong chemical bond energy in widegap semiconductors, and also adjusting the process conditions to overcome inherent defects in epitaxially grown films on non-native substrates using heteroepitaxy. Otherwise, an un-optimized etching process may result in surface morphologies that include pits and/or pillars.

An Inductively Coupled Plasma-Reactive Ion Etching (ICP-RIE) process with $Cl_2/Ar/N_2$ chemistry is provided, with an etch rate of about 100 nm/min for GaN. The dry etching process may be optimized using X-ray photoelectron spectroscopy (XPS), scanning electron microscopy (SEM), photoconductivity measurements, and photoluminescence (PL) measurements.

Fabrication Detail

Prior to dry etching, semiconductor wafer surfaces are treated with standard RCA cleaning procedures. As a mask for selective etching, a 500-nm-thick $SiO_2$ film is deposited by standard plasma-enhanced chemical vapor deposition (PECVD). Etching patterns are defined by deep UV lithography using a proximity aligner capable of generating 300 nm feature sizes. Electron beam deposition of Ni (~20 nm) followed by lift-off is carried out to complete the formation of mask for the $SiO_2$ etch.

Direct metal-masking of the semiconductor is not done in order to avoid un-intentional doping of the metal during the etch process. The ICP-RIE etching is performed using the following procedure. GaN etch is accomplished using ICP etching with a $Cl_2/N_2/Ar$ (25:5:2) gas mixture under a pressure of 5 mTorr with varying ICP etching power and radio frequency (RF) power. For nitrides, Chlorine-based etches are used because it has been shown to produce vertical sidewalls due to the ion assisted etching mechanism with smooth profiles. Temperature of the etch is a parameter that provides control of the sidewall angle. With low-temperature etch, the sub-surface damage may also be controlled.

Each sample is treated with a standard RCA clean before the activation annealing, the etching, and the measurements. Etching profile and surface morphology may be investigated by SEM. The surface chemical properties of semiconductor after the etch is characterized using an XPS system and PL measurements performed at room temperature. The electrical properties of etched semiconductor backbone are characterized photocurrent measurements. Photocurrent intensity is a direct measure of the surface recombination, i.e., higher photocurrent intensity will indicate less surface defect non-radiative recombination, hence less sub-surface damage. For GaN, Ti/Al/Ti/Au (70 nm/70 nm/50 nm/50 nm) ohmic electrodes are formed at both ends of the backbone nanostructures and then annealed at temperatures from 500 C to 800 C for ~1 min. The nanodevices are then functionalized with different metal and metal-oxide nanoclusters using reactive sputtering.

A schematic representation of an exemplary fabrication flow for semiconductor-nanocluster based gas sensors according to the present invention is shown in FIG. 37. As shown, the fabrication flow provides for parallel architecture, with multiple parallel sections. The multi-analyte arrays can be created on one single chip (10 mm×10 mm) by depositing clusters of different components on different micro-scale devices. This is possible due to low-temperature sputtering process used for the cluster deposition. An array of multiple sensors (e.g. for detecting $NO_x$, $SO_x$, $CO_x$, $NH_3$, and $H_2O$) may be fabricated all on one single chip. FIG. 38 shows exemplary inter-digitated GaN devices on Si and sapphire substrates formed using top-down processes (e.g., such as shown in FIG. 37).

Example 5

Protection against explosive-based terrorism may be achieved by large-scale production of nano-sensor arrays that are inexpensive, highly sensitive and selective with low response and recovery times. In this study, the selective response of GaN nanowire/$TiO_2$ nanocluster hybrids to nitroaromatic explosives, including trinitrotoluene (TNT), dinitrotoluene (DNT), nitrotoluene (NT), dinitrobenzene (DNB) and nitrobenzene (NB) at room temperature is demonstrated. The sensors detected between 0.5 ppb and 8 ppm TNT with good selectivity against interfering compounds such as toluene. The sensitivity of 1 ppm of TNT is ≅10% with response and recovery times of ≅30 seconds.

N-type (Si doped) GaN nanowires functionalized with $TiO_2$ nanoclusters were utilized for selectively sensing nitroaromatic explosive compounds. GaN is a wide-bandgap semiconductor (3.4 eV) with unique properties. Its chemical inertness and capability of operating in extreme environments (high-temperatures, presence of radiation, extreme pH levels) is highly desirable for sensor design. $TiO_2$ is a photocatalytic semiconductor with bandgap energy of 3.2 eV (anatase phase). The $TiO_2$ nanoclusters were selected to act as nanocatalysts to increase the sensitivity, lower the detection time, and enable the selectivity of the structures to be tailored to a target analyte (e.g., the most common explosives, trinitrotoluene (TNT) and other nitro-aromatics).

Materials and Methods

GaN nanowires were grown by Molecular Beam Epitaxy method as described in Bertness K A et al. (2008), supra, J. Crystal Growth 310(13):3154-3158. The nanowires are aligned on a pre-patterned substrate using dielectrophoresis. Details of the device fabrication are reported in Aluri G S et al. (2011) "*Highly selective GaN-nanowire/$TiO_2$-nanocluster hybrid sensors for detection of benzene and related environment pollutants,*" Nanotechnology 22(29):295503. After fabrication of two-terminal GaN NW devices, the $TiO_2$ NCs were deposited on the GaN NW surface using RF magnetron sputtering. The deposition was done at 325° C. with 50 standard cubic centimeters per minute (sccm) of Ar flow, and 300 W RF power. The nominal deposition rate was about 0.24 Å/s. Thermal annealing of the complete sensor devices (GaN NW with $TiO_2$ nanoclusters) was done at 700° C. for 30 seconds in a rapid thermal processing system. The device substrates, i.e., the sensor chips, were wire-bonded on a 24 pin ceramic package for the gas sensing measurements.

The microstructure and morphology of the sputtered $TiO_2$ films used for the fabrication of the sensors were characterized by high-resolution transmission and scanning transmission electron microscopy (HRTEM/STEM), selected-area electron diffraction (SAED), and field-emission scanning electron microscopy (FESEM). For the TEM characterization, the GaN NWs were dispersed on 10 nm thick carbon films supported by Mo-mesh grids, followed by the deposition of $TiO_2$ NCs and annealing and subsequent Pt deposition. The samples were analyzed in a FEI Titan 80-300 TEM/STEM microscope operating at 300 kV accelerating voltage and equipped with S-TWIN objective lenses, which provided 0.13 nm (STEM) and 0.19 nm (TEM) resolution by points. The instrument also had a Gatan CCD image acquisition camera, bright-field (BF), ADF and high-angle annular dark-field (HAADF) STEM detectors to perform spot, line profile, and areal compositional analyses using an EDAX 300 kV high-performance Si/Li X-ray energy dispersive spectrometer (XEDS).

The as-fabricated sensors were placed in a custom designed gas chamber for gas exposure measurements. Detailed description of the experimental setup and experimental conditions is provided in Aluri G S et al. (2011), supra, Nanotechnology 22(29):295503. The device characterization and the time dependent sensing measurements were done using an Agilent B1500A semiconductor parameter analyzer. The gas sensing experiments were performed by measuring the electrical conductance of the devices upon exposure to controlled flow of air/chemical mixture in presence of UV excitation (25 W deuterium bulb operating in the 215 nm to 400 nm range). For all the sensing experiments with chemicals, breathing air (<9 µmol/mol of water) was used as the carrier gas. After the sensor devices were exposed to the aromatic compounds, they were allowed to regain their baseline current with the air-chemical mixture turned-off, without purging or evacuating the test-chamber.

Results

Morphological and Structural Characterization of NWNC Hybrids

TEM imaging was conducted under minimal beam intensity conditions close to the Scherzer defocus at highest available accelerating voltage of 300 kV using both stationary beam (bright-field TEM/SAED, phase-contrast high-resolution TEM) and scanning beam (STEM/XEDS) modes. Areas for analyses were selected near the wire's edges and on the amorphous carbon support film in the vicinity of the NWs. FIG. 39 shows HRTEM micrographs of a GaN NW on a thin amorphous carbon support films with $TiO_2$ coating. The deposited $TiO_2$ layer formed an island-like film, where 10 nm to 50 nm partially aggregated particles (circled areas in FIG. 39) were often interconnected into extended two-dimensional networks. This was consistent with SAED and compositional analyses of deposited $TiO_2$ films indicating a mixture of polycrystalline anatase and rutile phases. Despite the limited contrast difference between $TiO_2$ and GaN, detailed HRTEM and HR-STEM observations revealed 0.35 nm (101) hcp lattice fringes belonging to anatase.

Current-Voltage (I-V) Characteristics of NWNC Hybrids

Figure 40:
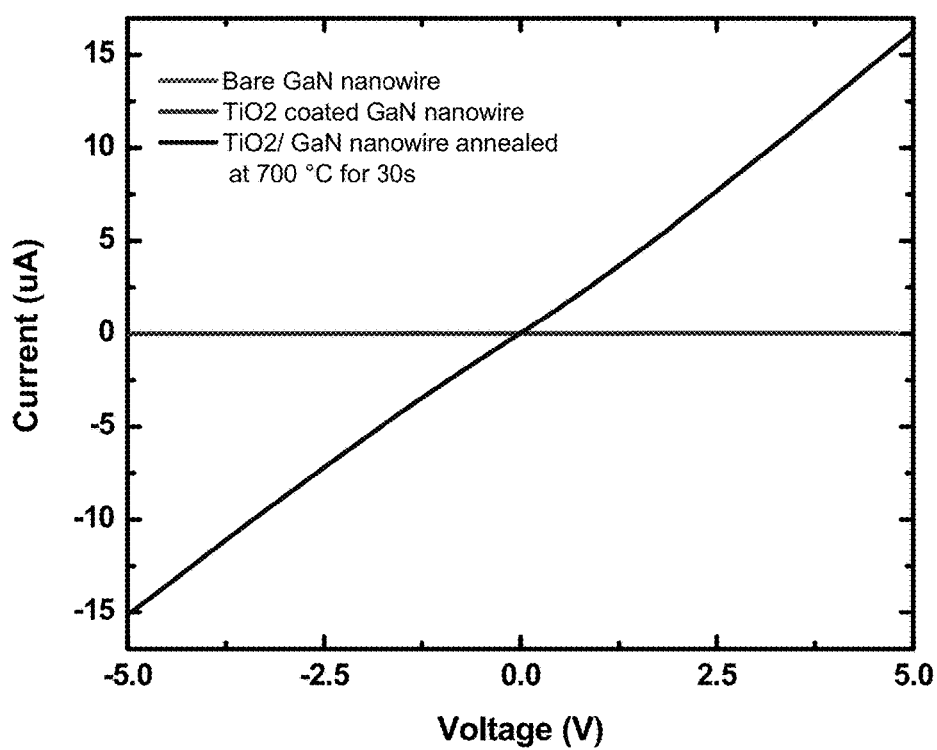
FIG. 40 illustrates graphically I-V characteristics of a GaN NW two-terminal device at different stages of processing.

Referring to FIG. 40, I-V characteristics of a GaN NW two-terminal device at different stages of processing are shown. The I-V curves of the as-deposited devices were non-linear and asymmetric (with a low current of 35 nA). However, the current increased (to a 100 nA) with the deposition of $TiO_2$ nanoclusters. This may be attributed to decreased surface depletion of the GaN NW due to passivation of surface states, and/or the high temperature deposition (325° C.) of the nanoclusters initiating ohmic contact formation. The devices annealed at 700° C. for 30 seconds showed significant changes in their I-V characteristics with a majority of the devices exhibiting linear I-V curves. This is consistent given low resistance ohmic contacts to the nitrides require annealing at 700° C.-800° C.

Sensing Behavior of GaN/$TiO_2$ NWNC Hybrid Sensors

The photocurrent through the bare GaN NW devices did not change when exposed to different chemicals mixed in air, even for concentrations as high as 3%. In contrast, the $TiO_2$-coated hybrid devices responded even to the pulses of 20 sccm airflow in the presence of UV excitation. The response of the $TiO_2$ NC-coated GaN nanowire hybrid sensors to different concentrations of benzene, toluene, ethylbenzene, chlorobenzene, and xylene in air is discussed above. The GaN/$TiO_2$ hybrids showed no response when exposed to other chemicals such as alcohols, ketones, amides, alkanes, nitro/halo-alkanes, and esters.

The response of the $TiO_2$ coated hybrid devices when exposed to a concentration of 100 ppb of the aromatics and nitro-aromatics in air can is shown in FIG. 41, plate (a). The photocurrent for these sensors increased with respect to air when exposed to toluene vapors, whereas for every other aromatic compound the photocurrent decreased relative to air. The response is observed to increase with the increase in the number of nitro groups attached to the aromatic compound. The response of the hybrid device to different concentrations of TNT in air from 8 ppm down to as low as 500 ppt is shown in FIG. 41, plate (b). The response time is defined as the time taken by the sensor current to reach 90% of the response ($I_f$-$I_0$) when exposed to the analyte. The $I_f$ is the steady sensor current level in the presence of the analyte, and $I_0$ is the current level without the analyte, which in this case is in the presence of air. The recovery time is the time required for the sensor current to recover to 30% of the response ($I_f$-$I_0$) after the gas flow is turned off. The response and recovery times of the nano-devices to different concentrations of TNT are ≅30 seconds. The response and recovery times of the rest of the compounds varied from ≅60 seconds to ≅75 seconds.

Figure 42:
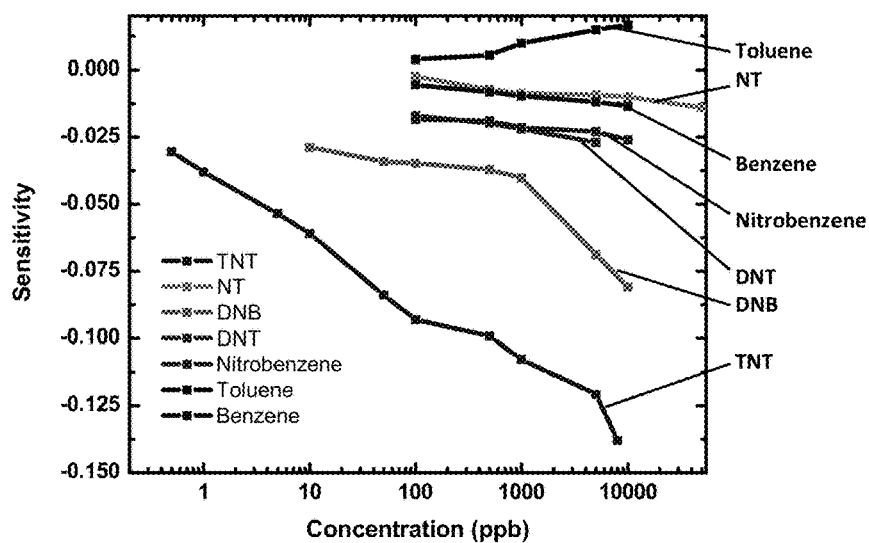
FIG. 42 is a sensitivity plot of a GaN—TiO$_2$ nanowire-nanocluster hybrid device for benzene, toluene, nitrotoluene, nitrobenzene, DNT, DNB and TNT.
Figure 43:
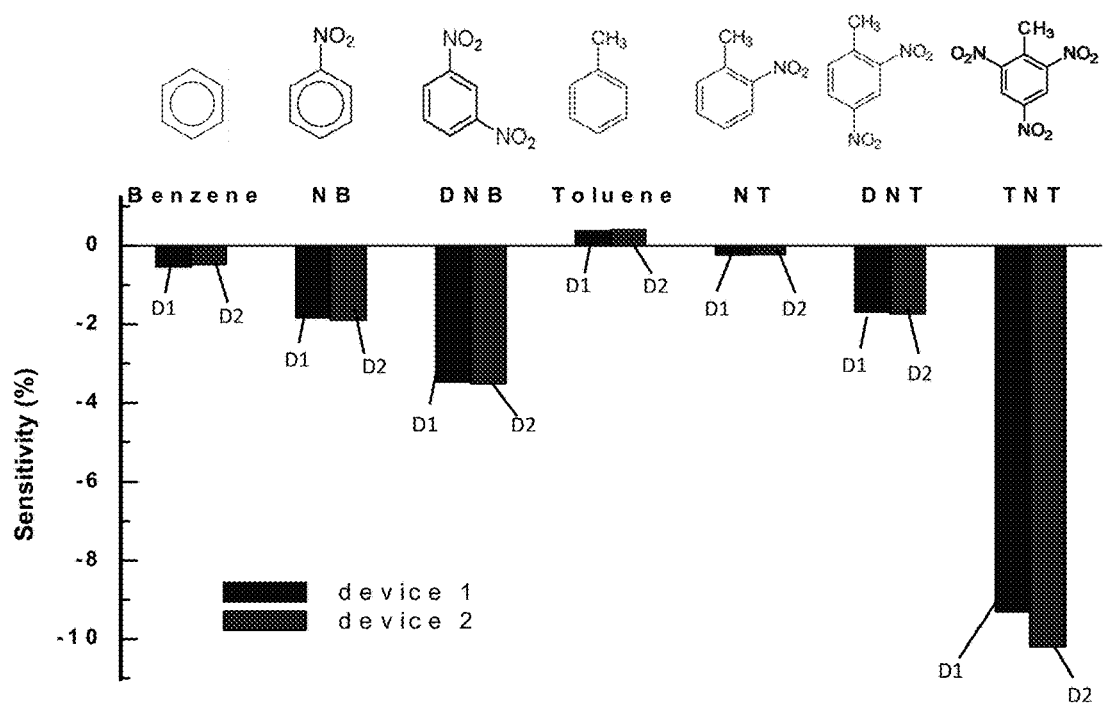
FIG. 43 illustrates sensitivity of two different nanowire-nanocluster hybrid sensors to 100 ppb of the different aromatic compounds.

The sensitivity is defined as ($R_{gas}$-$R_{air}$)/$R_{air}$, where $R_{gas}$ and $R_{air}$ are the resistances of the sensor in the presence of the chemical-air mixture and in presence of air, respectively. The sensitivity plot of a hybrid device for the different aromatics and nitro-aromatics tested is shown in FIG. 42. The sensitivity (($R_{gas}$-$R_{air}$)/$R_{air}$) for 1 ppm of TNT is ≅10%. The devices exhibit a very highly sensitive and selective response to TNT when compared to interfering compounds like toluene. Toluene shows an increase in response with respect to air, whereas TNT shows a decrease when compared to air. The plot identifies the sensor's ability to sense wide concentration ranges of the indicated chemicals. The sensitivity of two different devices (device 1—D1; device 2—D2) to the different aromatic compounds can be seen in FIG. 43.

As discussed above, oxygen vacancy defects ($Ti^{3+}$ sites) on the surface of $TiO_2$ are the "active sites" for the adsorption of species like oxygen, water, and organic molecules. In the presence of UV excitation with an energy above the bandgap energy of anatase $TiO_2$ (3.2 eV) and GaN (3.4 eV), electron-hole pairs are generated both in the GaN NW and in the $TiO_2$ cluster. Photogenerated holes in the nanowire tend to diffuse towards the surface due to surface band bending. This effect of separation of photogenerated charge carriers results in a longer lifetime of photogenerated electrons, which in turn enhances the photoresponse of the nanowire devices in general. Since the nitro-aromatic compounds are highly electronegative, they tend to attract electrons from other molecules through charge transfer. This charge transfer between the adsorbed species on the $TiO_2$ nanocluster, and the nitro groups in the nitro-aromatic compounds increases the width of the depletion region in the nanowire device, reducing the current.

The potential of the disclosed nanostructure-nanocluster hybrids for next-generation nano-sensors having the capability to detect explosive compounds quickly and reliably is clearly demonstrated. The GaN/$TiO_2$ nanowire nanocluster hybrid devices tested detected trace amounts of aromatic and nitro-aromatic compounds in air at room temperature with very low response and recovery times (≅30 seconds). The nitro-aromatic explosives like TNT are selectively detectable even for concentrations as low as 500 ppt.

Example 6

Nitrogen dioxide ($NO_2$) sensors using gallium nitride (GaN) nanowires (NWs) functionalized with titanium dioxide ($TiO_2$) nanoclusters are demonstrated. Exemplary sensor fabrication methodologies are described above (e.g., see Example 1 & FIG. 19).

Figure 44:
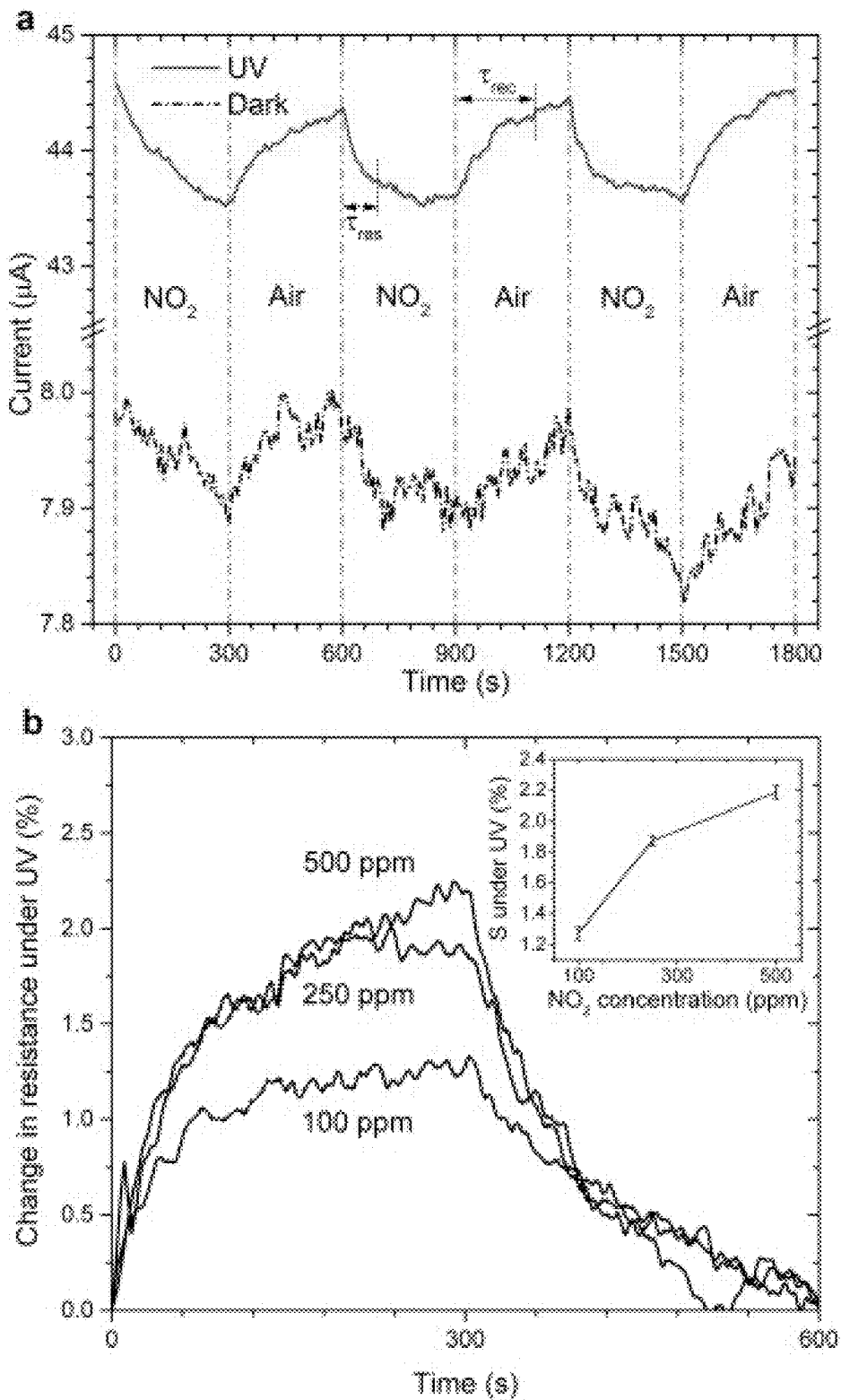

FIG. 44, plate (a) illustrates the dynamic responses of the $TiO_2$ based sensor exposed to 250 ppm $NO_2$ mixed with breathing air under UV illumination and dark, and at room temperature. For each cycle, the gas exposure time was 300 s. FIG. 44, plate (b) illustrates change in resistance under UV at mixtures of 100 ppm, 250 ppm, and 500 ppm with breathing air, with the inset showing the measured responses under UV as a function of $NO_2$ concentrations with uncertainty. Sensitivity S is presented by $(I_g-I_\alpha) \times 100/I_\alpha$, wherein $I_g$ is the device current in the presence of an analyte in breathing air and $I\alpha$ is the current in pure breathing air, both measured 300 s after the flow is turned on. FIG. 45 illustrates schematically an $NO_2$ gas sensing mechanism of the $TiO_2$ sensor under UV illumination and at room temperature. FIG. 45, plate (a) shows the mechanism in a dark environment with breathing air in. FIG. 45, plate (b) shows the mechanism under UV illumination in breathing air. FIG. 45, plate (c) shows the mechanism under UV illumination with a mixture of $NO_2$ and breathing air.

The response of the $TiO_2$ based sensor exposed to 500 ppm $NO_2$ under UV illumination and under dark at room temperature is shown in FIG. 46. As described, the UV illumination allows for efficient photodesorption of adsorbed oxygen and hydroxyl species, thus introducing additional oxide surface sites or receptors for adsorption of target molecules. Photocatalytic reactions then occur between the adsorbed target molecules and the photo carriers in the oxide sites, leading to a modification of the surface potential and semiconductor backbone current change (transduction). The photodesorption of the adsorbed target molecules and reaction species leads to a reversal of photocurrent to baseline (recovery).

Figure 47:
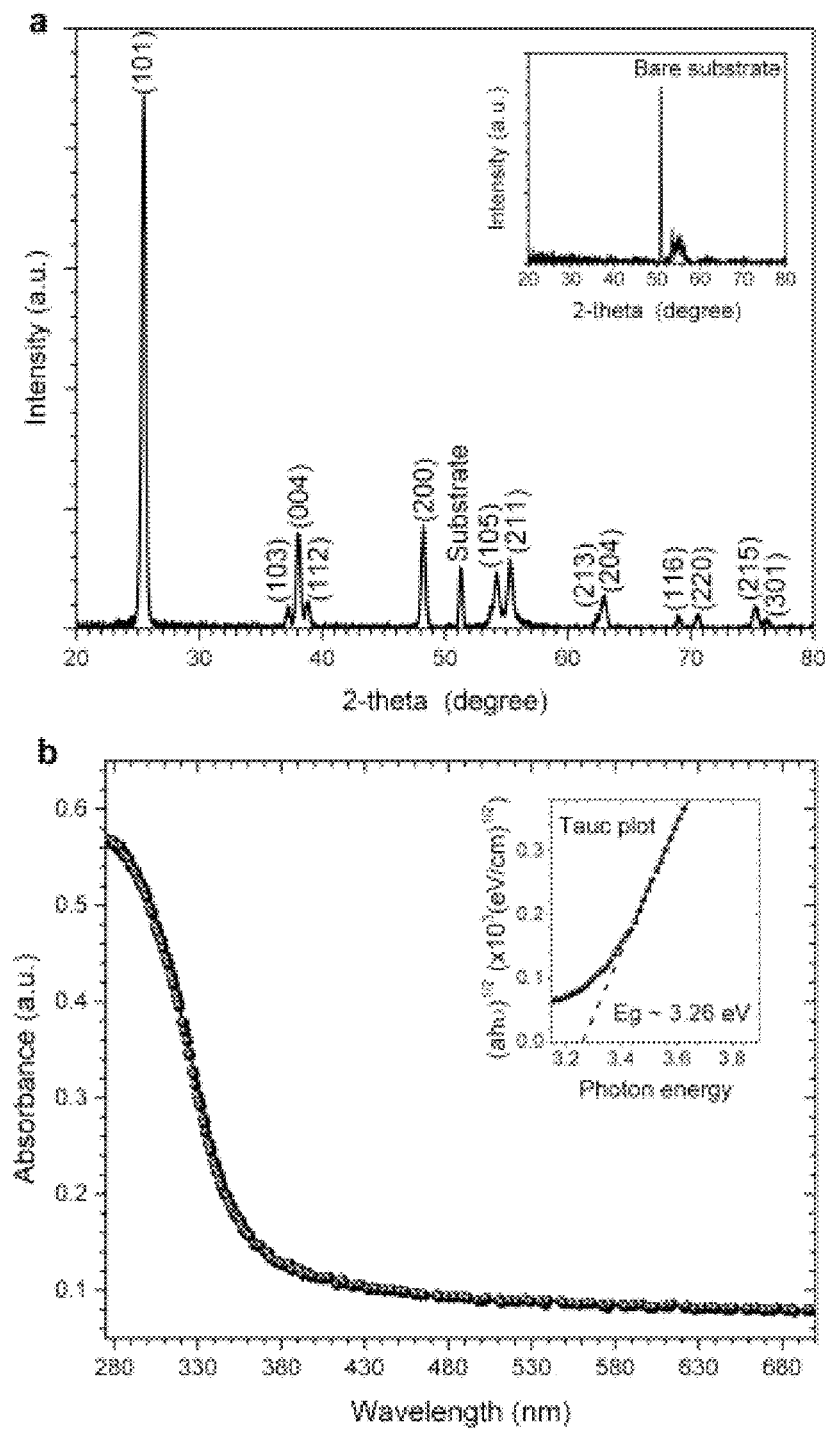
FIG. 47, plate (a) illustrates a GIXRD scan of thermally processed ultrathin TiO$_2$ film, and plate (b) illustrates optical properties (bandgap).

A GIXRD scan of thermally processed ultrathin $TiO_2$ film is shown in FIG. 47, plate (a). Optical properties (bandgap) are illustrated in FIG. 47, plate (b).

Example 7

Carbon dioxide ($CO_2$) sensors using gallium nitride (GaN) nanowires (NWs) functionalized with tin oxide and copper oxide ($SnO_2$—CuO) nanoclusters are demonstrated. Exemplary sensor fabrication methodologies are described above.

Figure 48:
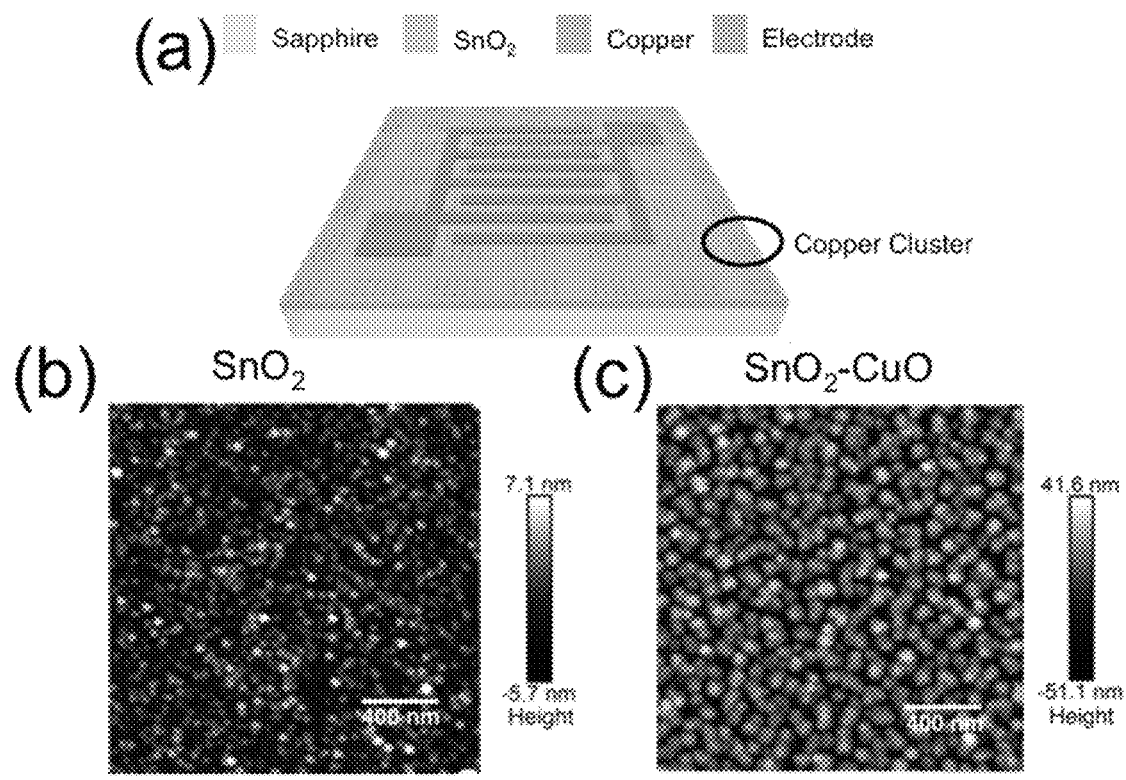
FIG. 48, plate (a) illustrates schematically a SnO$_2$—Cu nanocluster CO$_2$ sensor. Plates (b) and (c) are AFM images of the SnO$_2$—Cu nanocluster CO$_2$ sensor.
Figure 49:
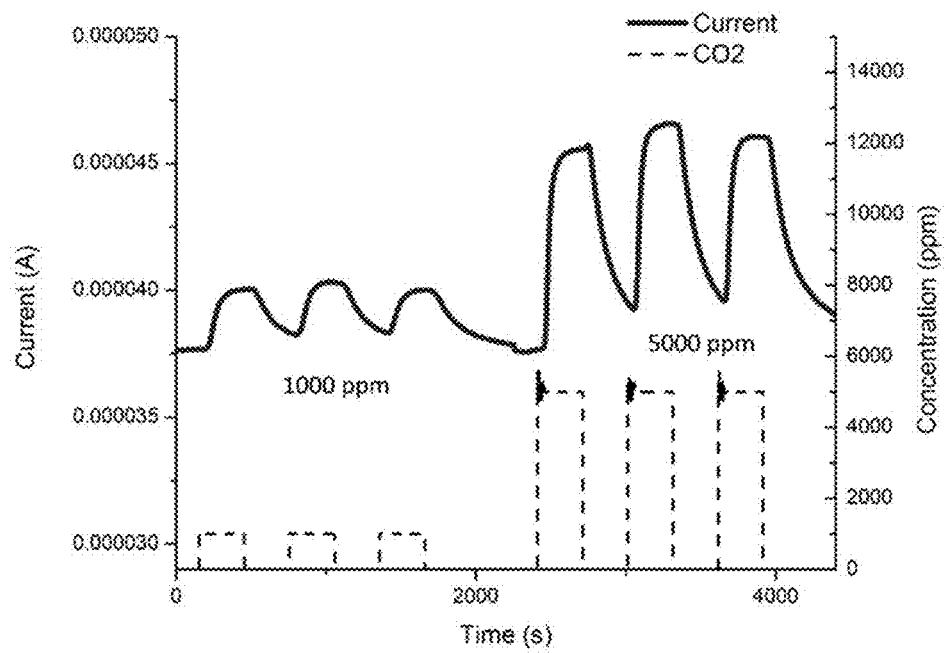
FIG. 49 illustrates the dynamic responses of the SnO$_2$—Cu based sensor exposed to CO$_2$ at room temperature at concentrations of 1000 ppm and 5000 ppm. For each cycle, the gas exposure time was 300 s.
Figure 50:
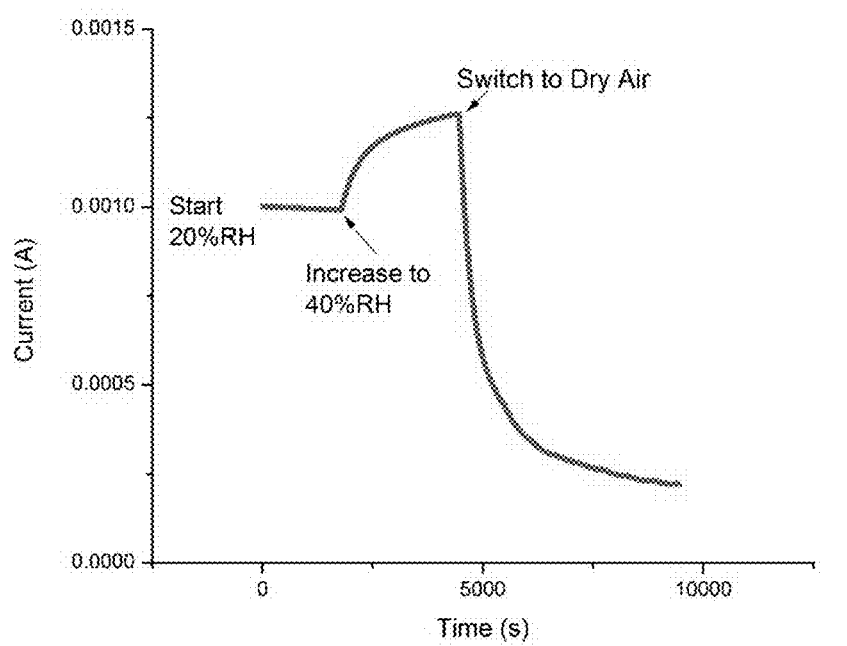
FIG. 50 illustrates graphically the response of the SnO$_2$ based sensor at different relative humidity (RH) concentrations at room temperature.

FIG. 48, plate (a) illustrates schematically a $SnO_2$—Cu nanocluster $CO_2$ sensor, including an electrode disposed on a sapphire substrate, and GaN NWs functionalized with $SnO_2$ nanoclusters and $SnO_2$—CuO nanoclusters. AFM images of the $SnO_2$—Cu nanocluster $CO_2$ sensor are shown in FIG. 48, plates (b) and (c). FIG. 49 illustrates the dynamic response of the $SnO_2$—Cu based sensor exposed to $CO_2$ at room temperature for various concentrations. FIG. 50 illustrates graphically the response of the $SnO_2$ based sensor at different relative humidity (RH) concentrations at room temperature.

All publications and patents mentioned in this specification are herein incorporated by reference to the same extent as if each individual publication or patent application was specifically and individually indicated to be incorporated by reference in its entirety. While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth.

What is claimed is:

1. One or more nanoparticle gas sensors on a single chip, which sensors are configured to detect at least one type of gas, the device comprising:
   a single chip having a first semiconductor layer on top of a substrate layer;
   a plurality of semiconductor electrodes etched from the first semiconductor layer; and
   an adsorption layer for at least some of the one or more nanoparticle gas sensors which adsorbs a first type of gas and a first interfering compound, which adsorption layer includes deposits of either (a) first metal oxide nanoparticles and second metal oxide nanoparticles on a first subset of the plurality of semiconductor electrodes or (b) third metal oxide nanoparticles and first metal nanoparticles on the first subset of semiconductor electrodes.

2. The device of claim 1, wherein the one or more nanoparticle gas sensors on the single chip are a same type of gas sensor configured to detect a single type of gas.

3. The device of claim 1, wherein the first semiconductor layer is made from GaN.

4. The device of claim 1, wherein the one or more nanoparticle sensors on the single chip detect one or more of $NO_x$, $SO_x$, $CO_x$, $NH_3$ and $H_2O$, where x is an integer value.

5. The device of claim 1, wherein the etching of the first semiconductor layer is performed using at least one of reactive ion etching (RIE) or wet chemical etching.

6. The device of claim 1, wherein a buffer layer is provided between the first semiconductor layer and the substrate layer.

7. The device of claim 1, wherein all of the nanoparticles have a diameter of less than 200 nm.

8. The device of claim 1, wherein the substrate layer is made from one of Si and Sapphire.

9. The device of claim 1, wherein the at least one type of gas is at least two types of gases, the device further comprising:
   another adsorption layer for at least some of the one or more nanoparticle gas sensors which adsorbs a second type of gas and a second interfering compound, which adsorption layer includes deposits of either (c) fourth metal oxide nanoparticles and fifth metal oxide nanoparticles on a second subset of the plurality of semiconductor electrodes or (d) sixth metal oxide nanoparticles and second metal nanoparticles on the second subset of semiconductor electrodes.

10. The device of claim 9, wherein the one or more nanoparticle sensors on the single chip detect two of $NO_x$, $SO_x$, $CO_x$, $NH_3$ and $H_2O$ where x is an integer value.

11. The device of claim 1, wherein said one or more nanoparticle sensors exhibit a change in output upon detection of said at least one type of gas, said output selected from the group consisting of current, voltage and resistance.

12. The device of claim 1, wherein said one or more nanoparticle sensors enable detection of said at least one type of gas within a carrier gas of air, nitrogen or argon.

13. The device of claim 1, wherein said one or more nanoparticle sensors exhibit increased conductivity upon exposure to said at least one type of gas in the presence of UV excitation.

14. One or more particle gas sensors on a single chip, which sensors are configured to detect at least one type of gas, the device comprising:

a single chip having a first semiconductor layer on top of a substrate layer;

a plurality of semiconductor electrodes etched from the first semiconductor layer; and an adsorption layer for at least some of the one or more particle gas sensors which adsorbs a first type of gas and a first interfering compound, which adsorption layer includes deposits of either (a) first metal oxide particles and second metal oxide particles on a first subset of the plurality of semiconductor electrodes or (b) third metal oxide particles and first metal particles on the first subset of semiconductor electrodes, wherein all of the particles have a diameter of less than 200nm.

15. The device of claim 14, wherein the one or more gas sensors on the single chip are a same type of gas sensor configured to detect a single type of gas.

16. The device of claim 14, wherein the first semiconductor layer is made from GaN.

17. The device of claim 14, wherein the one or more sensors on the single chip detect one or more of $NO_x$, $SO_x$, $CO_x$, $NH_3$ and $H_2O$ where x is an integer value.

18. The device of claim 14, wherein the etching of the first semiconductor layer is performed using at least one of reactive ion etching (RIE) or wet chemical etching.

19. The device of claim 14, wherein a buffer layer is provided between the first semiconductor layer and the substrate layer.

20. The device of claim 14, wherein the substrate layer is made from one of Si and Sapphire.

21. The device of claim 14, wherein the at least one type of gas is at least two types of gases, the device further comprising:

another adsorption layer for at least some of the one or more particle gas sensors which adsorbs a second type of gas and a second interfering compound, which adsorption layer includes deposits of either (c) fourth metal oxide particle and fifth metal oxide particle on a second subset of the plurality of semiconductor electrodes or (d) sixth metal oxide particle and second metal nanoparticles on the second subset of semiconductor electrodes.

22. The device of claim 21, wherein the one or more particle sensors on the single chip detect two of $NO_x$, $SO_x$, $CO_x$, $NH_3$ and $H_2O$ where x is an integer value.

23. The device of claim 14, wherein said one or more particle sensors exhibit a change in output upon detection of said at least one type of gas, said output selected from the group consisting of current, voltage and resistance.

24. The device of claim 14, wherein said one or more particle sensors enable detection of said at least one type of gas within a carrier gas of air, nitrogen or argon.

25. The device of claim 14, wherein said one or more particle sensors exhibit increased conductivity upon exposure to said at least one type of gas in the presence of UV excitation.

* * * * *